(12) United States Patent
Chou et al.

(10) Patent No.: US 11,940,382 B2
(45) Date of Patent: *Mar. 26, 2024

(54) ASSAY WITH AMPLIFICATION

(71) Applicant: Essenlix Corporation, Monmouth Junction, NJ (US)

(72) Inventors: Stephen Y. Chou, Princeton, NJ (US); Wei Ding, East Windsor, NJ (US); Yufan Zhang, Monmouth Junction, NJ (US); Ji Qi, Hillsborough, NJ (US); Ji Li, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 211 days.

This patent is subject to a terminal disclaimer.

(21) Appl. No.: 16/484,803

(22) PCT Filed: Feb. 8, 2018

(86) PCT No.: PCT/US2018/017492
§ 371 (c)(1),
(2) Date: Aug. 8, 2019

(87) PCT Pub. No.: WO2018/148461
PCT Pub. Date: Aug. 16, 2018

(65) Prior Publication Data
US 2020/0225161 A1     Jul. 16, 2020

Related U.S. Application Data

(60) Provisional application No. 62/459,303, filed on Feb. 15, 2017, provisional application No. 62/459,267, filed on Feb. 15, 2017, provisional application No. 62/460,083, filed on Feb. 16, 2017, provisional application No. 62/460,052, filed on Feb. 16, 2017, provisional application No. 62/456,904, filed on Feb. 9, 2017, provisional application No. 62/457,075, filed on Feb. 9, 2017, provisional application No. 62/457,084, filed on Feb. 9, 2017.

(51) Int. Cl.
*G01N 21/65* (2006.01)
*G01N 21/64* (2006.01)
*G01N 21/66* (2006.01)
*G01N 33/543* (2006.01)
*G01N 33/58* (2006.01)

(52) U.S. Cl.
CPC .............. *G01N 21/65* (2013.01); *G01N 21/64* (2013.01); *G01N 21/66* (2013.01); *G01N 33/54366* (2013.01); *G01N 33/582* (2013.01); *G01N 2201/06113* (2013.01)

(58) Field of Classification Search
CPC ........ G01N 21/65; G01N 21/64; G01N 21/66; G01N 33/54366; G01N 33/582; G01N 21/658; G01N 21/648; G01N 21/6452; G01N 21/6428; G01N 2201/06113; C12Q 1/68

See application file for complete search history.

(56) References Cited

U.S. PATENT DOCUMENTS

| | | |
|---|---|---|
| 3,368,872 A | 2/1968 | Natelson |
| 3,447,863 A | 6/1969 | Patterson |
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |

(Continued)

FOREIGN PATENT DOCUMENTS

| | | |
|---|---|---|
| AU | 198813789 A | 9/1988 |
| AU | 619459 B | 1/1992 |

(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.

(Continued)

*Primary Examiner* — Narayan K Bhat

(57) ABSTRACT

A homogeneous assay method that employs a device is provided. In some embodiments, the device contains a pair of plates that can be opened and closed. The sample is placed between two plates. In some embodiments, the thickness of the sample in a closed configuration, the concentration of labels, and amplification factor of the amplification surface are configured to make the label(s) bound on the amplification surface visible without washing away of the unbound labels.

89 Claims, 28 Drawing Sheets

(56) References Cited

U.S. PATENT DOCUMENTS

| | | |
|---|---|---|
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,405,054 B1 | 7/2008 | Hasenback et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,110,025 B2 | 8/2015 | Rissin et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 10,324,009 B2 * | 6/2019 | Chou ............... G01N 35/00029 |
| 2001/0055882 A1 | 12/2001 | Ostuni |
| 2002/0164820 A1 | 11/2002 | Brown |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |

(56) References Cited

U.S. PATENT DOCUMENTS

| | | |
|---|---|---|
| 2006/0160134 A1 | 7/2006 | Melker et al. |
| 2007/0087442 A1 | 4/2007 | Wardlaw |
| 2007/0231796 A1* | 10/2007 | Majda ................. C12Q 1/6825 |
| | | 435/6.16 |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0071038 A1 | 3/2011 | Ermantraut et al. |
| 2011/0206557 A1 | 8/2011 | Phan et al. |
| 2011/0212462 A1 | 9/2011 | Duffy et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2012/0321518 A1 | 12/2012 | Ermantraut et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0154668 A1 | 6/2014 | Chou et al. |
| 2014/0315242 A1 | 10/2014 | Rodriguez et al. |
| 2014/0368631 A1 | 12/2014 | Wardlaw et al. |
| 2014/0378320 A1 | 12/2014 | Hoffmann et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1* | 2/2016 | Chou ............... G01N 33/57473 |
| | | 436/501 |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |
| 2020/0095629 A1* | 3/2020 | Chou ........................ B01L 7/52 |
| 2021/0140957 A1* | 5/2021 | Chou ............... B01L 3/502715 |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| CN | 105209884 A | 12/2015 |
| CN | 105358979 A2 | 2/2016 |
| EP | 261667 A2 | 3/1988 |
| EP | 291153 A1 | 11/1988 |
| EP | 261667 A3 | 5/1989 |
| EP | 291153 | 6/1992 |
| EP | 261667 B1 | 2/1993 |
| EP | 0961110 | 12/1999 |
| EP | 1949310 | 7/2008 |
| EP | 2290100 | 3/2011 |
| EP | 1949310 | 11/2011 |
| EP | 2439515 | 4/2012 |
| EP | 2554987 | 2/2013 |
| EP | 3026433 | 6/2016 |
| EP | 1949310 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2008128352 | 10/2008 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014144133 | 9/2014 |
| WO | 2014183049 | 11/2014 |
| WO | 2014205576 | 12/2014 |
| WO | 2017048871 | 3/2017 |

OTHER PUBLICATIONS

Written Opinion for PCT/US2018/017713 established by ISA/KR, dated Jun. 20, 2018.

\* cited by examiner

A
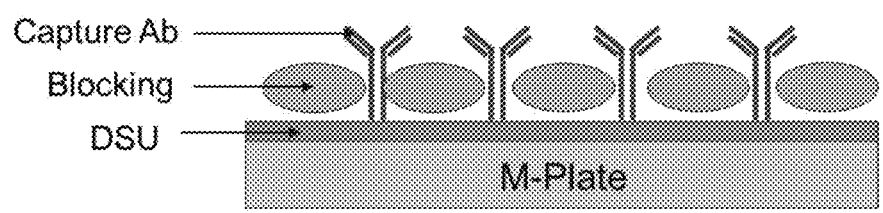
Capture Ab
Blocking
DSU
B
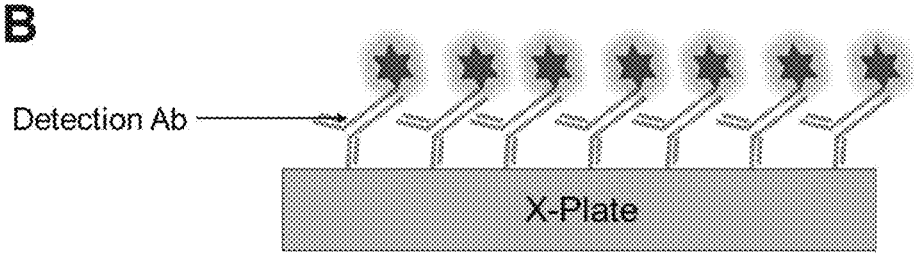
Detection Ab
FIG. 6

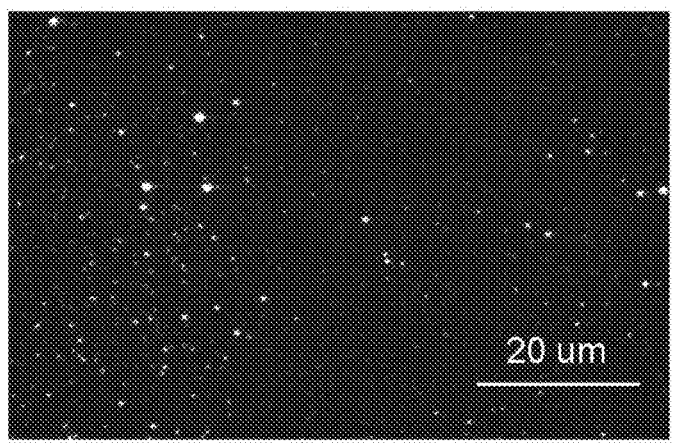
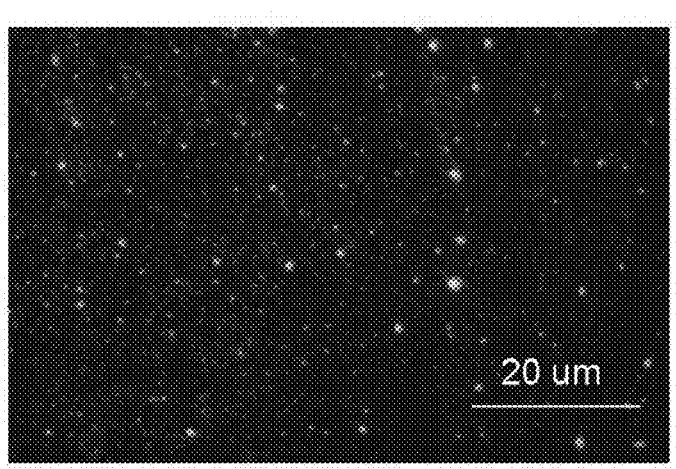
FIG. 8

A
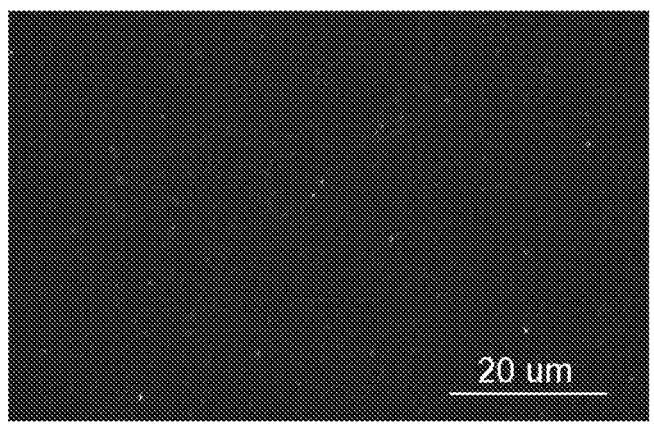
B
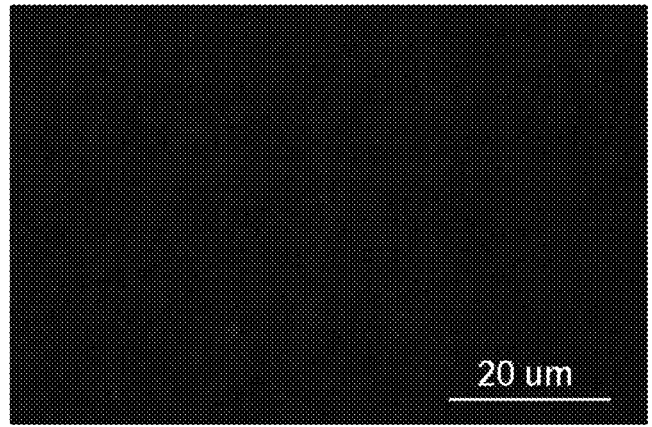
FIG. 9

A
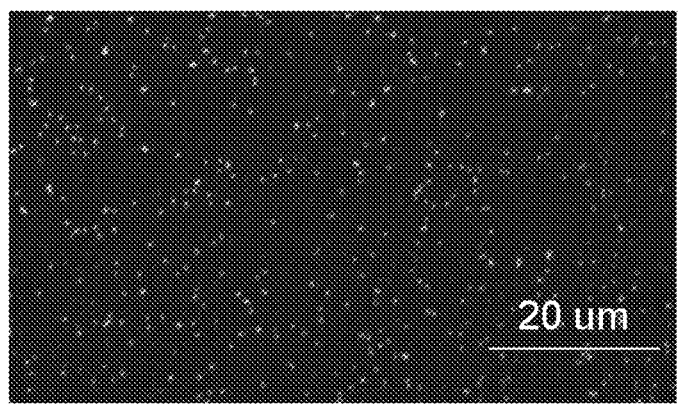
B
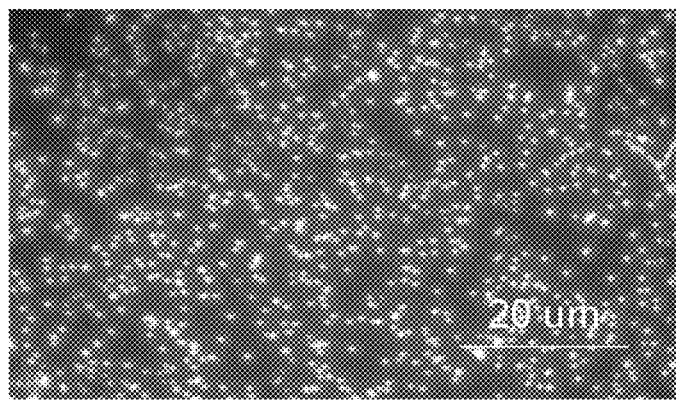
FIG. 10

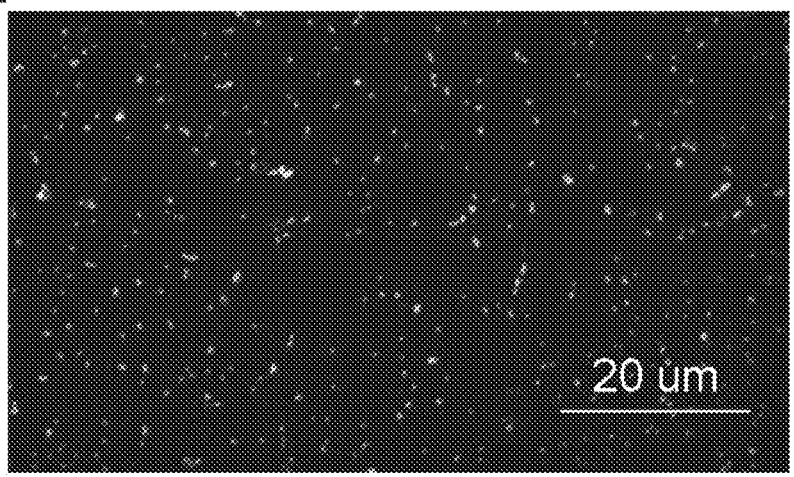
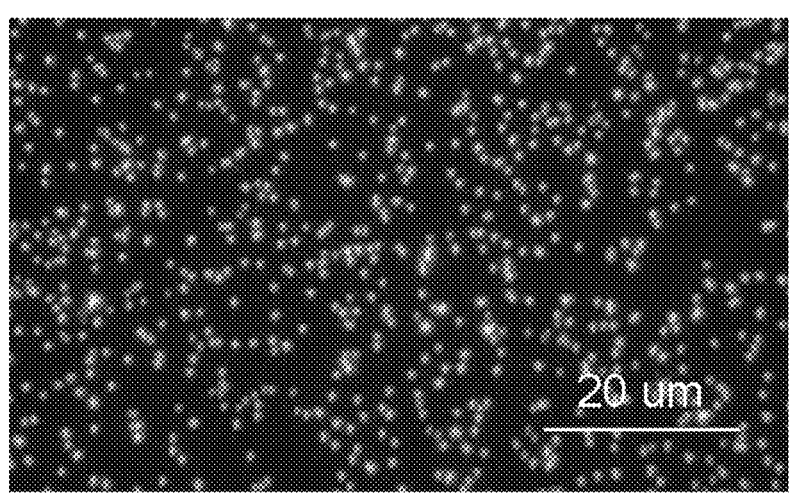
FIG. 11 a M-Plate
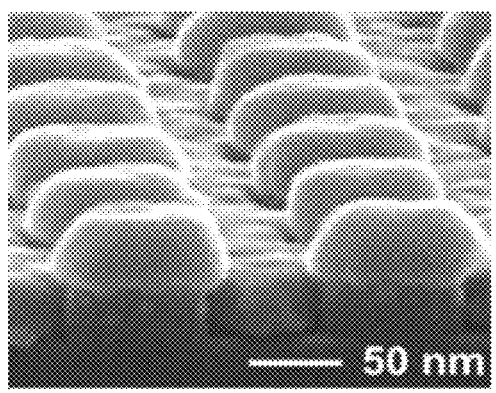
b X-Plate
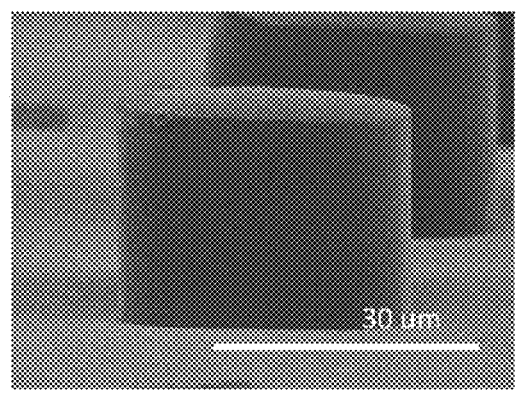
FIG. 14

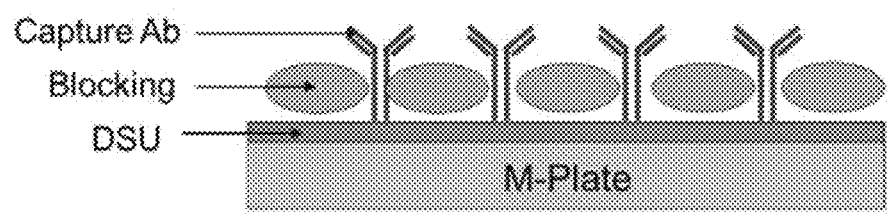
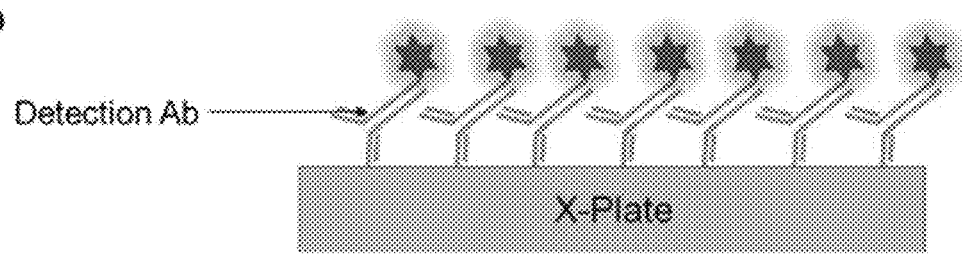
FIG. 17 a) On top surface of one layer device
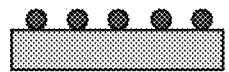
b) On metal surface of two layer device
c) On glass/plastic surface of two layer device
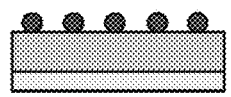
FIG. 23

| No. | First Layer | Thickness (um) | Second Layer | Thickness (um) | Label Side | E.F. |
|---|---|---|---|---|---|---|
| 1 | Glass | 1000 | N/A | | --- | 1 |
| 2 | Glass | 1000 | Aluminum | 0.1 | Metal Side | 5 |
| 3 | Glass | 1000 | Gold | 0.05 | Metal Side | 6 |
| 4 | Plastic | 50 | Gold | 0.005 | Metal Side | 4 |
| 5 | Aluminum | 0.1 | Plastic | 50 | P/G Side | 8 |
| 6 | Gold | 0.05 | Plastic | 50 | P/G Side | 4 |
| 7 | Gold | 0.005 | Plastic | 50 | P/G Side | 3 |
| 8 | Aluminum | 0.1 | Glass | 1000 | P/G Side | 2 |
| 9 | Gold | 0.05 | Glass | 1000 | P/G Side | 2 |

Excitation: 633 nm, Emission: 650 nm

Fluorescence beads enhancement

| No. | First Layer | Thickness (um) | Second Layer | Thickness (um) | Label Side | E.F. |
|---|---|---|---|---|---|---|
| 1 | Glass | 1000 | N/A | | | 1 |
| 2 | Glass | 1000 | Aluminum | 0.1 | Metal Side | 9 |
| 3 | Glass | 1000 | Gold | 0.05 | Metal Side | 12 |
| 4 | Aluminum | 0.1 | Plastic | 25 | P/G Side | 11 |
| 5 | Gold | 0.05 | Plastic | 25 | P/G Side | 6 |
| 6 | Aluminum | 0.1 | Plastic | 50 | P/G Side | 8 |
| 7 | Gold | 0.05 | Plastic | 50 | P/G Side | 6 |
| 8 | Aluminum | 0.1 | Plastic | 175 | P/G Side | 2 |
| 9 | Gold | 0.05 | Plastic | 175 | P/G Side | 1 |
| 10 | Aluminum | 0.1 | Glass | 1000 | P/G Side | 1.4 |
| 11 | Gold | 0.05 | Glass | 1000 | P/G Side | 1.4 |

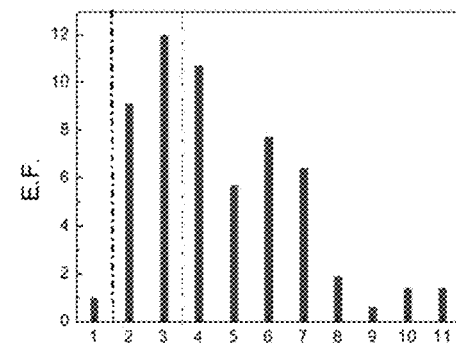

Excitation: 532 nm, Emission: 600 nm

FIG. 25

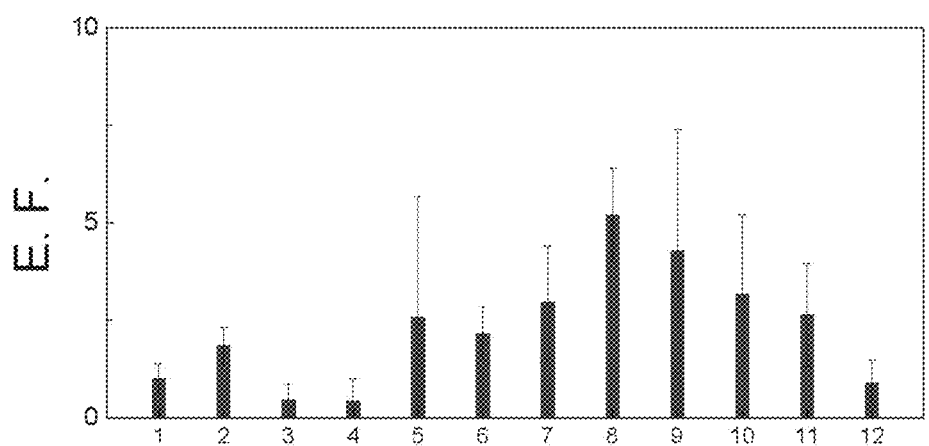

| 1. Slide, Front Detect | 1 | 5. Slide (Au contact), Back Detect | 2.6 | 9. Slide (Al non-contact 125 um PET), Back Detect | 4.2 |
| --- | --- | --- | --- | --- | --- |
| 2. Slide, Back Detect | 1.8 | 6. Slide (Au non-contact), Back Detect | 2.1 | 10. Slide (Al back-contact), Front Detect | 3.2 |
| 3. Slide (Au contact), Front Detect | 0.45 | 7. Slide (Al contact), Back Detect | 3.0 | 11. Slide (Al back-contact, blank-front), Front Detect | 2.6 |
| 4. Slide (Au non-contact), Front Detect | 0.4 | 8. Slide (Al non-contact 50 um PET), Back Detect | 5.1 | 12. Slide (Al back-contact, Au front), Front Detect | 0.9 |

FIG. 28

ASSAY WITH AMPLIFICATION

CROSS-REFERENCE TO RELATED APPLICATIONS

This application is a § 371 national stage application of International Application PCT/US2018/017492 filed on Feb. 8, 2018, which claims the benefit of priority to U.S. provisional application Ser. No. 62/457,084 filed on Feb. 9, 2017 (ESX-017PRV), 62/459,267 filed on Feb. 15, 2017 (ESX-017PRV2), 62/456,904 filed on Feb. 9, 2017 (ESX-027PRV), 62/459,303 filed on Feb. 15, 2017 (ESX-027PRV2), 62/457,075 filed on Feb. 9, 2017 (ESX-035PRV), 62/460,052 filed on Feb. 16, 2017 (ESX-035PRV2) and 62/460,083 filed on Feb. 16, 2017 (ESX-035PRV3), the contents of which are relied upon and incorporated herein by reference in their entirety. The entire disclosure of any publication or patent document mentioned herein is entirely incorporated by reference.

FIELD

Among other things, the present invention is related to devices and methods of performing biological and chemical assays.

BACKGROUND

In biological and chemical assays (e.g. diagnostic testing), often it needs to measure the volume, change the shape, and/or detect analytes of a sample or a part of the sample, quickly and simply. Multiple steps of incubation and wash cycles are inevitably required in a typical assay (e.g. immunoassay, nucleic assay and colorimetric assay, etc.) method. Therefore, the entire assay usually takes several hours to days to obtain the assay results, and is difficult to adapt to high throughput and automation.

SUMMARY OF INVENTION

The following brief summary is not intended to include all features and aspects of the present invention.

In one aspect, the current invention is related to the methods and systems that can improve the detection of an analyte in a sample. The analyte includes, among many others, proteins, peptides, DNA, RNA, nucleic acid, oligonucleotide, small molecules, cells, nanoparticle with different sizes and shapes. The detection includes the detection of the existence, quantification of the concentration, and determination of the states of the targeted analyte.

In another aspect, the invention is related to the combination of a QMAX device which a surface amplification layer on the QMAX surface, where the surface amplification layer amplifies an optical signal of a label depending upon the label's distance from the surface amplification: high amplification when the label is on the amplification surface, but weak or no amplification at all when the label is a few microns away from the amplification surface. The combination of the QMAX with amplification surface offer several advantage, either alone or together, including not limited to: (1) allowing signal molecule detection leading to pixelated reading (e.g. digital reading), (2) high detection sensitivity with lumpsum reading or digital reading, and (3) homogeneous assay that does not require any wash or open up QMAX card (e.g. single drop of the sample and then reading the results). Furthermore, the QMAX card make the sample thickness very thin uniform, leading to fast total assay time (less than 60 second) and small testing variation. For example, the present invention has experimentally demonstrated one touch homogenous assay in less than 60 sec. In another aspect, the invention is related to the combination of this method with QMAX device, which can improve the performance (limit of detection) of QMAX. In another aspect, the invention is related to wash-free homogeneous assay method without requirements of any separation steps or washing steps, other than the performances to accelerate the process and quantify the parameters (e.g. analyte concentration, the sample volume, etc.), simplify the sample collection and measurement processes, handle samples with small volumes, perform entire assays in a short amount of time (e.g. less than a minute), allow results to be analyzed automatically (e.g. by a mobile phone), and allow non-professionals to perform the assay her/himself.

For example, a liquid biological sample, e.g., blood, saliva or urine, which in many cases may be of an unknown volume in the range of 0.5 ul to 100 ul, may be analyzed using the present device and method in a homogenous assay, where the term "homogenous assay" is intended to refer to an assay that is done on the "neat" sample in the absence of any washing steps or purification steps that separate some constituents of the sample from other constituents. The assay can be done extremely rapidly and, in some embodiments, a reading can be taken in as little as 30 seconds (e.g., 1 minute) of placing the plates in the closed configuration. As such, the entire method, from placing the sample on one of the plates of the device, closing the plates together, reading the plates and determining the amount of an analyte in the sample can be done can be done in minutes. Moreover, as will be described in greater detail below, the assay is also very sensitive and has a sensitivity of 500 fM (using the bulk signal method) and 50 fM (using pixelated counting method).

BRIEF DESCRIPTION OF THE DRAWINGS

The skilled artisan will understand that the drawings, described below, are for illustration purposes only. The drawings are not intended to limit the scope of the present teachings in any way. The drawings not are not entirely in scale. In the figures that present experimental data points, the lines that connect the data points are for guiding a viewing of the data only and have no other means.

FIG. 6 shows schematics of preparation of binding site plate (first plate—M-Plate) and storage plate (second plate—X-Plate) of an exemplary embodiment of QMAX for pixelated reading.

FIG. 8 shows examples photos of 40 nm fluorescence beads on gold substrate (a) measured by high sensitive electron multiplying charge coupled device (EMCCD) and (b) measured by digital single-lens reflex (DSLR) camera, both of them are pixelated reading.

FIG. 9 shows examples photos of 40 nm fluorescence beads on glass substrate (a) measured by high sensitive electron multiplying charge coupled device (EMCCD) and (b) measured by digital single-lens reflex (DSLR) camera, both of them are pixelated reading.

FIG. 10 shows examples photos of 1 um fluorescence beads on gold substrate (a) measured by high sensitive electron multiplying charge coupled device (EMCCD) and (b) measured by digital single-lens reflex (DSLR) camera, both of them are pixelated reading.

FIG. 11 shows examples photos of 1 um fluorescence beads on glass substrate (a) measured by high sensitive electron multiplying charge coupled device (EMCCD) and (b) measured by digital single-lens reflex (DSLR) camera, both of them are pixelated reading.

FIG. 14 shows SEMs of structures on first plate and second plate of an exemplary embodiment of a QMAX devices that employs a wash-free homogenous assay.

FIG. 17 shows schematics of preparation of binding site plate (first plate) and storage plate (second plate) of an exemplary embodiment for homogenous QMAX.

FIG. 23 shows schematics of one experiment as example using device shown in FIG. 21. (a) Fluorescence dye or beads on top surface of one layer device; (b) Fluorescence dye or beads on top of two layer device (metal and dielectric material); (c) Fluorescence dye or beads on top of the two layer device (dielectric material and metal).

FIG. 25 shows experimental results of fluorescence beads enhancements with setup shown in FIG. 23. E.F. gives the enhancements for different devices.

FIG. 28 shows experimental results of fluorescence molecule (IR-800 dye) enhancements with setup shown in FIG. 26. E.F. gives the enhancements for different devices

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

QMAX Assay

In biological and chemical assaying (i.e. testing), a device and/or a method that simplifies assaying operation or accelerates assaying speed is often of great value.

Figure 1:
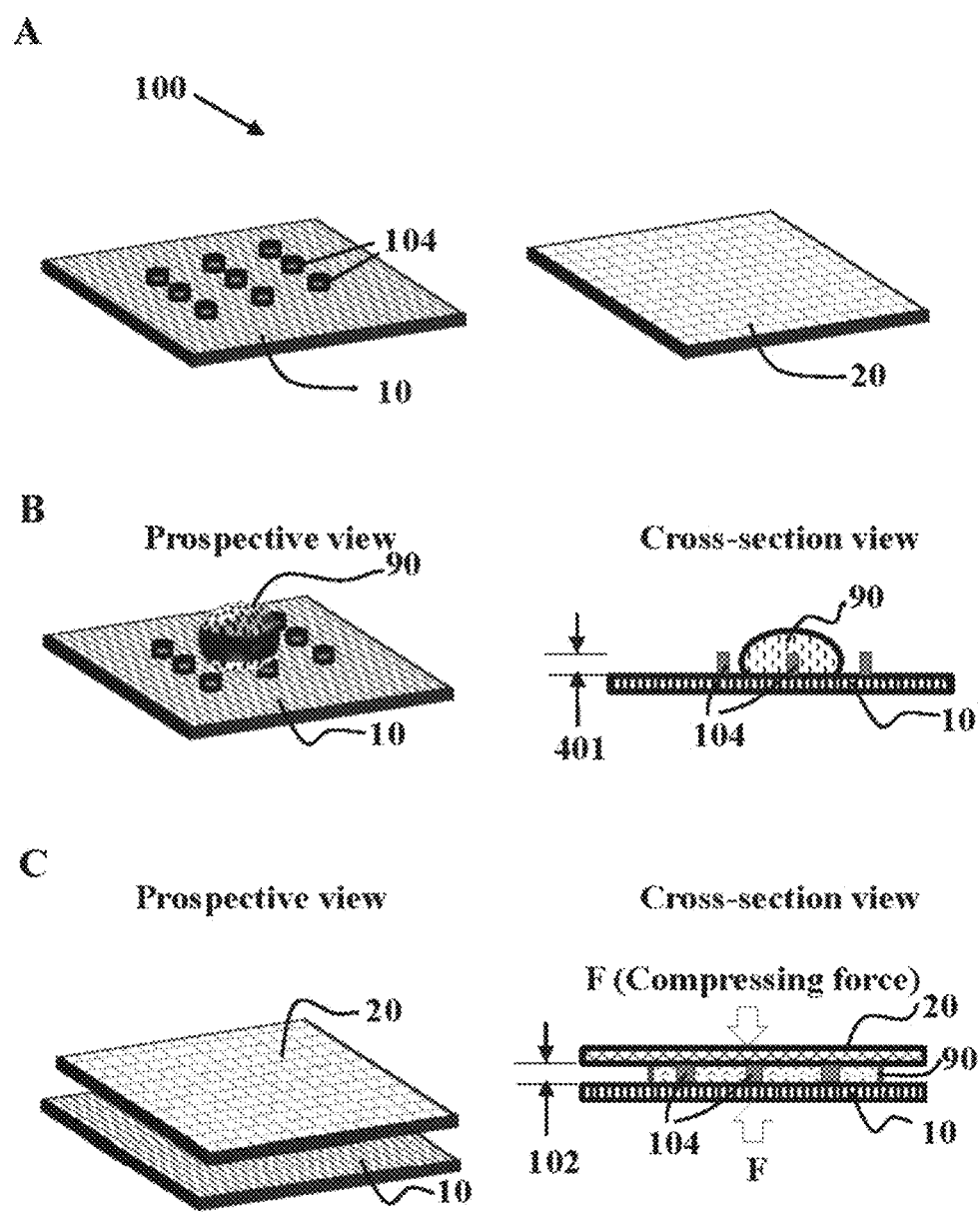
FIG. 1 shows an embodiment of a QMAX (Q: quantification; M: magnifying; A: adding reagents; X: acceleration; also known as compressed regulated open flow (CROF)) device, which comprises a first plate and a second plate. Panel (A) shows the perspective view of the plates in an open configuration when the plates are separated apart; panel (B) shows the perspective view and a sectional view of depositing a sample on the first plate at the open configuration; panel (C) the perspective view and a sectional view of the QMAX device in a closed configuration.

In the QMAX (Q: quantification; M: magnifying; A: adding reagents; X: acceleration; also known as compressed regulated open flow (CROF)) assay platform, a QMAX card uses two plates to manipulate the shape of a sample into a thin layer (e.g. by compressing) (as illustrated in FIG. 1). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers.

In a QMAX assay operation, an operator often needs to add assay reagents into the sample in a controlled fashion. For instance, in some embodiments, the reagents (e.g. detection agent and binding agent) are coated on the plate surface of the QMAX device, and some reagents (e.g. detection agent) are released into the sample at an appropriate timing during the assay process. Among many others, in some cases, it is desirable for the detection agent to be added after the substantial binding of the target analyte by the binding agent. In other cases, it is desirable to add the detection agent after the formation of the thin film of the sample. In other cases, it is desirable to delay the addition of the detection agent by a specified time period. The present invention is to provide devices and methods for achieving these goals as well as for making bio/chemical sensing (including, not limited to, immunoassay, nucleic assay, electrolyte analysis, etc.) faster, more sensitive, less steps, easy to perform, smaller amount of samples required, less or reduced (or no) needs for professional assistance, and/or lower cost, than many current sensing methods and devices.

The term "compressed open flow (COF)" refers to a method that changes the shape of a flowable sample deposited on a plate by (i) placing other plate on top of at least a part of the sample and (ii) then compressing the sample between the two plates by pushing the two plates towards each other; wherein the compression reduces a thickness of at least a part of the sample and makes the sample flow into open spaces between the plates. The term "compressed regulated open flow" or "CROF" (or "self-calibrated compressed open flow" or "SCOF" or "SCCOF") (also known as QMAX) refers to a particular type of COF, wherein the final thickness of a part or entire sample after the compression is "regulated" by spacers, wherein the spacers are placed between the two plates. Here the CROF device is used interchangeably with the QMAX device.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface. The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX device refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing. The term "area" of an object in a QMAX process refers to, unless specifically stated, the area of the object that is parallel to a surface of the plate. For example, spacer area is the area of the spacer that is parallel to a surface of the plate.

The term of QMAX device refers the device that perform a QMAX (e.g. CROF) process on a sample, and have or not have a hinge that connect the two plates.

A. Pixelated Counting Method for Assays Using QMAX Device

A-1. Examples of System and Method for Sample Analysis

FIG. 1 shows an embodiment of a generic QMAX device, that have or not have a hinge, and wherein Q: quantification; M: magnifying; A: adding reagents; X: acceleration; also known as compressed regulated open flow (CROF)) device. The generic QMAX device comprises a first plate 10 and a second plate 20. In particular, panel (A) shows the perspective view of a first plate 10 and a second plate 20 wherein the first plate has spacers. It should be noted, however, that the spacers also are fixed on the second plate 20 (not shown) or on both first plate 10 and second plate 20 (not shown). Panel (B) shows the perspective view and a sectional view of depositing a sample 90 on the first plate 10 at an open configuration. It should be noted, however, that the sample 90 also is deposited on the second plate 20 (not shown), or on both the first plate 10 and the second plate 20 (not shown). Panel (C) illustrates (i) using the first plate 10 and second plate 20 to spread the sample 90 (the sample flow between the inner surfaces of the plates) and reduce the sample thickness, and (ii) using the spacers and the plate to regulate the sample thickness at the closed configuration of the QMAX device. The inner surfaces of each plate have one or a plurality of binding sites and or storage sites (not shown).

In some embodiments, the spacers 40 have a predetermined uniform height and a predetermined uniform inter-spacer distance. In the closed configuration, as shown in panel (C) of FIG. 1, the spacing between the plates and the thus the thickness of the sample 90 is regulated by the spacers 40. In some embodiments, the uniform thickness of the sample 90 is substantially similar to the uniform height of the spacers 40. It should be noted that although FIG. 1 shows the spacers 40 to be fixed on one of the plates, in some embodiments the spacers are not fixed. For example, in certain embodiments the spacers is mixed with the sample so that when the sample is compressed into a thin layer, the spacers, which is rigid beads or particles that have a uniform size, regulate the thickness of the sample layer.

A-2. System for Sample Analysis with Pixelated Counting

One aspect of the present invention is to provide a system for sample analysis. The system comprises (a) a QMAX device for binding target analyte in a sample to capture agents that are attached to a plate of the device; (b) a reading device for producing an image of signals emanating from the device that represent individual targeted analyte binding events; (c) a computer comprising programs for identifying and counting individual binding events in an area of the image.

Figure 2:
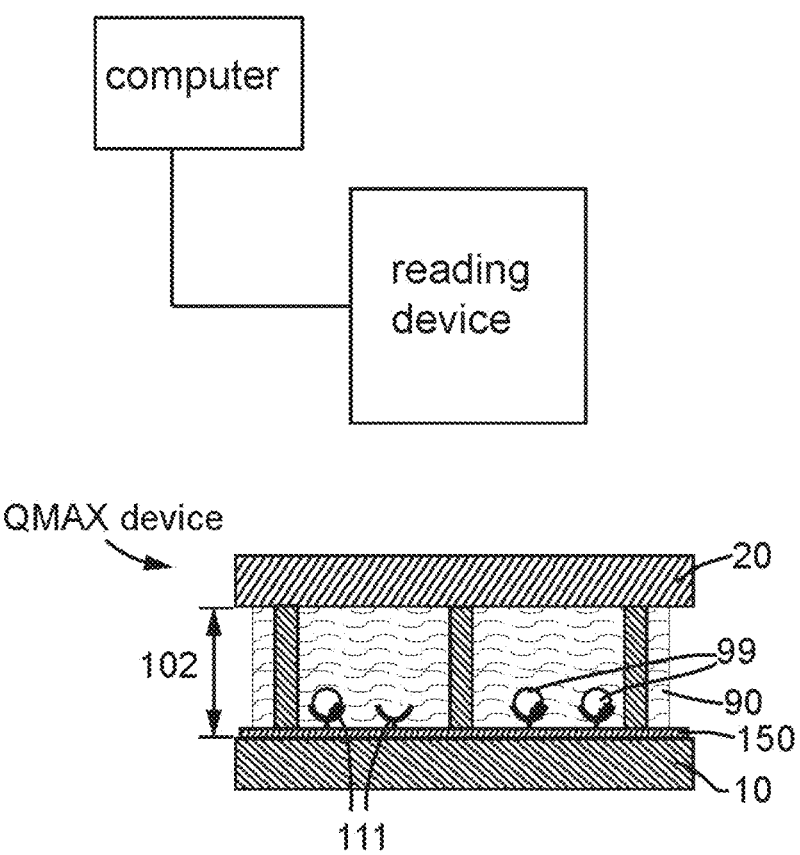
FIG. 2 shows an embodiment of a system for sample analysis, which comprises a QMAX device and a reading device.

FIG. 2 schematically shows of an embodiment of a system for sample analysis provided by the present invention. The system comprises a QMAX device, a reading device, and a computer. In this exemplary embodiment, the QMAX device is configured to bind target analyte 99 in the sample 90 to capture agents 111 that are attached to the first plate 10 when the first plate 10 and the second plate 20 are at the closed configuration. On the other hand, the reading device is configured to read the plates to provide an image of signals that represent individual binding events when the plates are at the closed configuration. The computer, as discussed above, comprises programs to identify and count individual binding events in an area of the image, thereby providing an estimate of the amount of one or more analytes in the sample.

As shown in the FIG. 2, similar to FIG. 1, the QMAX device comprises a first plate 10, a second plate 20, spacers 40, and proximity-dependent signal amplification layer 150. The spacers 40 are fixed to the first plate 10. The first plate 10 further comprises a binding site 101 (not shown) in its sample contact area (not shown). It should be noted, however, the binding site 101 can also be on the second plate 20, or both the first plate 10 and the second plate 20. The binding site 101 contains capture agents 111. FIG. 2 shows the closed configuration of the QMAX device, in which the sample 90 containing target analyte 99 is compressed by the two plates into a layer of uniform thickness. As discussed above, the uniform thickness of the layer is substantially similar to the uniform height of the spacers 40. The capture agents 111 are capable of binding and immobilizing the target analyte 99 in the sample. As demonstrated, at the closed configuration, the target analyte 99 in the layer of uniform thickness is bound by the capture agents 11. The proximity-dependent signal amplification layer 150 a signal amplification layer that amplifies a signal from an analyte or a labeled analyte (e.g., a light-emitting label) in a proximity-dependent manner.

The term "capture agent" as used herein refers to an agent that binds to a target analyte through an interaction that is sufficient to permit the agent to bind and concentrate the target molecule from a heterogeneous mixture of different molecules. The binding interaction is typically mediated by an affinity region of the capture agent. Typical capture agents include any moiety that can specifically bind to a target analyte. Certain capture agents specifically bind a target molecule with a dissociation constant (Kn) of less than about $10^{-6}$ M (e.g., less than about $10^{-7}$ M, less than about $10^{-8}$ M, less than about $10^{-9}$ M, less than about $10^{-19}$ M, less than about $10^{-11}$ M, less than about $10^{-12}$ M, to as low as $10^{-16}$ M, or a range between any two of the values) without significantly binding to other molecules. Exemplary capture agents include proteins (e.g., antibodies), and nucleic acids (e.g., oligonucleotides, DNA, RNA including aptamers).

In some embodiments, the reading device is a CCD camera. In some embodiments, the reading device is a photodetector and comprises one or more other optical devices that are selected from optical filters, spectrometer, lenses, apertures, beam splitter, mirrors, polarizers, waveplates, and shutters. The reading device collects the position, local intensity, local spectrum and local Raman signature of said signals.

For examples, for optical signal detection, optical filters, light beam splitters, optical fibers, a photodetector (e.g. PMT, APO), imaging camera (e.g. CCD's) and spectrometer together with a scanner provided by the device assembly can be coupled to a microscope system which uses a far-field confocal setting or a wide-field view setting.

In confocal setting, the reading is performed by recording the 's brightness, temporal change and spectral change of one or a few pixels a time and raster scanning the entire interested area of the SAL. In wide-field view setting, a camera is used to record the brightness and temporal change of the entire or a fraction of SAL area a time. Proper optical filters and light beam manipulators (polarizer, beam splitters, optical fibers, etc.) is need to ensure only the desired signal is collected and detected.

In some embodiments, the reading device is a mobile communication device that comprises a digital camera. In some embodiments, the mobile communication device further comprises a light source that provides uniform illumination of the QMAX device for the signal reading. In some embodiments, the system further comprises an external light source that provides uniform illumination of the QMAX device for the signal reading.

A-3. Proximity-Dependent Signal Amplification Layer

In some embodiments, the plate of the QMAX device that comprises the capture agents further comprises a proximity-dependent signal amplification layer in its sample contact area. The proximity-dependent signal amplification layer (SAL) is configured to enhance the signal representative of the binding events.

In some embodiments, the SAL comprises a layer of nanostructures made of metallic materials and dielectric/semiconductor materials, that can enhance the signal. Often the outer surface of the SAL (the inner surface of SAL is the surface in contact with the substrate surface) is coated with a molecular adhesion/spacer layer, which serves one of the two or both of the functions: (1) provide a good adhesion to bond to the capture agents, and (2) a spacer that control the distance between the metal in the SAL and the signal generation molecule to optimize signal amplification. One preferred SAL embodiment is that the dimension of one, several or all critical metallic and dielectric components of SAL are less than the wavelength of the light in sensing.

In some embodiments, the proximity-dependent signal amplification layer comprises a D2PA array. The terms "disk-coupled dots-on-pillar antenna array" and "D2PA" as used herein refer to an array that comprises: (a) substrate; and (b) a D2PA structure, on the surface of the substrate, comprising one or a plurality of pillars extending from a surface of the substrate, wherein at least one of the pillars comprises a pillar body, metallic disc on top of the pillar, metallic backplane at the foot of the pillar, the metallic back plane covering a substantial portion of the substrate surface near the foot of the pillar; metallic dot structure disposed on sidewall of the pillar. The D2PA amplifies a light signal that is proximal to the surface of the D2PA. The D2PA enhances local electric field and local electric field gradient in regions that is proximal to the surface of the D2PA. The light signal includes light scattering, light diffraction, light absorption, nonlinear light generation and absorption, Raman scattering, chromaticity, luminescence that includes fluorescence, electroluminescence, chemiluminescence, and electrochemiluminescence.

A D2PA array may also comprise a molecular adhesion layer that covers at least a part of said metallic dot structure, said metal disc, and/or said metallic back plane and, optionally, a capture agent that specifically binds to an analyte, wherein said capture agent is linked to the molecular adhesion layer of the D2PA array. The nanosensor can amplify a light signal from an analyte, when said analyte is bound to the capture agent. One preferred SAL embodiment is that the dimension of one, several or all critical metallic and dielectric components of SAL are less than the wavelength of the light in sensing.

The term "molecular adhesion layer" refers to a layer or multilayer of molecules of defined thickness that comprises an inner surface that is attached to a device and an outer (exterior) surface that can be bound to capture agents.

In some embodiments, the proximity-dependent signal amplification layer includes, but not limited to, the proximity-dependent signal amplification layers described in U.S. Provisional Patent Application No. 61/347,178, which was filed on May 21, 2010, U.S. Provisional Patent Application No. 61/622,226, which was filed on Apr. 10, 2012, U.S. Provisional Patent Application No. 61/708,314, which was filed on Oct. 1, 2012, U.S. Provisional Patent Application No. 61/800,915, which was filed on Mar. 15, 2013, U.S. Provisional Patent Application No. 61/801,933, which was filed on Mar. 15, 2013, U.S. Provisional Patent Application No. 61/801,096, which was filed on Mar. 15, 2013, U.S. Provisional Patent Application No. 61/801,424, which was filed on Mar. 15, 2013, U.S. Provisional Patent Application No. 61/794,317, which was filed on Mar. 15, 2013, U.S. Provisional Patent Application No. 62/090,299, which was filed on Dec. 10, 2014, U.S. Provisional Patent Application No. 62/066,777, which was filed on Oct. 21, 2014, U.S. Provisional Patent Application No. 62/234,538, which was filed on Sep. 29, 2015, U.S. Utility patent application Ser. No. 13/699,270, which was filed on Jun. 13, 2013, U.S. Utility patent application Ser. No. 13/838,600, which was filed on Mar. 15, 2013, U.S. Utility patent application Ser. No. 14/459,239, which was filed on Aug. 13, 2014, U.S. Utility patent application Ser. No. 14/459,251, which was filed on Aug. 13, 2014, U.S. Utility patent application Ser. No. 14/852,412, which was filed on Mar. 16, 2014, U.S. Utility patent application Ser. No. 14/871,678, which was filed on Sep. 30, 2015, U.S. Utility patent application Ser. No. 14/431,266, which was filed on Oct. 5, 2015, U.S. Utility patent application Ser. No. 14/668,750, which was filed on Mar. 25, 2015, U.S. Utility patent application Ser. No. 14/775,634, which was filed on Sep. 11, 2015, U.S. Utility patent application Ser. No. 14/775,638, which was filed on Sep. 11, 2015, U.S. Utility patent application Ser. No. 14/852,417, which was filed on Sep. 11, 2015, U.S. Utility patent application Ser. No. 14/964,394, which was filed on Dec. 9, 2015, PCT Application (designating U.S.) No. PCT/US2011/037455, which was filed on May 20, 2011, PCT Application (designating U.S.) No. PCT/US2013/032347, which was filed on Mar. 15, 2013, PCT Application (designating U.S.) No. PCT/US2013/062923, which was filed on Oct. 1, 2013, PCT Application (designating U.S.) No. PCT/US2014/030108, which was filed on Mar. 16, 2014, PCT Application (designating U.S.) No. PCT/US2014/029675, which was filed on Mar. 14, 2014, PCT Application (designating U.S.) No. PCT/US2014/028417, which was filed on Mar. 14, 2014, PCT Application (designating U.S.) No. PCT/US2014/029979, which was filed on Mar. 15, 2014, PCT Application (designating U.S.) No. PCT/US2015/056518, which was filed on Oct. 20, 2015, PCT Application (designating U.S.) No. PCT/US2016/054025, which was filed on Sep. 27, 2016, the complete disclosures of which are hereby incorporated by reference for all purposes.

The terms "proximity-dependent signal amplification layer", "amplification surface", and "surface amplification layer" are interchangeable.

A-4. Signals and Pixelated Reading

The signal emitted from a QMAX device can directly come from the analyte or a label attached to the analyte, or the combination. In some embodiments, the signal is an electromagnetic signal, including electrical and optical signals with different frequencies, light intensity, fluorescence, chromaticity, luminescence (electrical and chemo-luminescence), Raman scattering, time resolved signal (including blinking). In some embodiments, the signals also can be the forces due to local electrical, local mechanical, local biological, or local optical interaction between the plate and the reading device. In some embodiments, the signal includes the spatial (i.e. position), temporal and spectral distribution of the signal. In some embodiments, the detection signal also can be absorption.

In optical detection (i.e. detection by electromagnetic radiation), the methods that can be used include far-field optical methods, near-field optical methods, epifluorescence spectroscopy, confocal microscopy, two-photon microscopy, and total internal reflection microscopy, where the target analytes are labelled with an electromagnetic radiation emitter, and the signal in these microscopies can be amplified by the SML.

The reading will use appropriate detecting systems for the signal to be detected in sequence or in parallel or their combination. In a sequential detection, one or several pixels are detected a time, and scanner will be used to move the detection into other areas of the SAL. In a parallel detection, a multipixel detector array, such as imaging camera (e.g. CCD's), will be used to take detect the signals from different pixels at the same time. The scan can be single path or multi-path with a different pixel size for each path.

The pixel size for the reading/detection will be adjusted to for the balance of optical resolution and total reading time. A smaller pixel size will take a longer time for reading/scanning the entire or fraction of the SAL. A typical pixel size is 1 um to 10 um in size. The pixel has different shapes: round, square and rectangle. The lower limit of the pixel size is determined by the optical resolution of the microscope system, and the higher limit of the pixel size is determined in order to avoid reading error from the uneven optical response of the imager (optical aberration, illumination uniformity, etc.).

A-5. Pixelated Analysis

The signals detected in a pixelated manner are analyzed to determine the number and/or types of the particular molecules at a particular pixel or several pixels, which, in turn is used to quantify the type and/or concentration of the targeted analytes.

Figure 3:
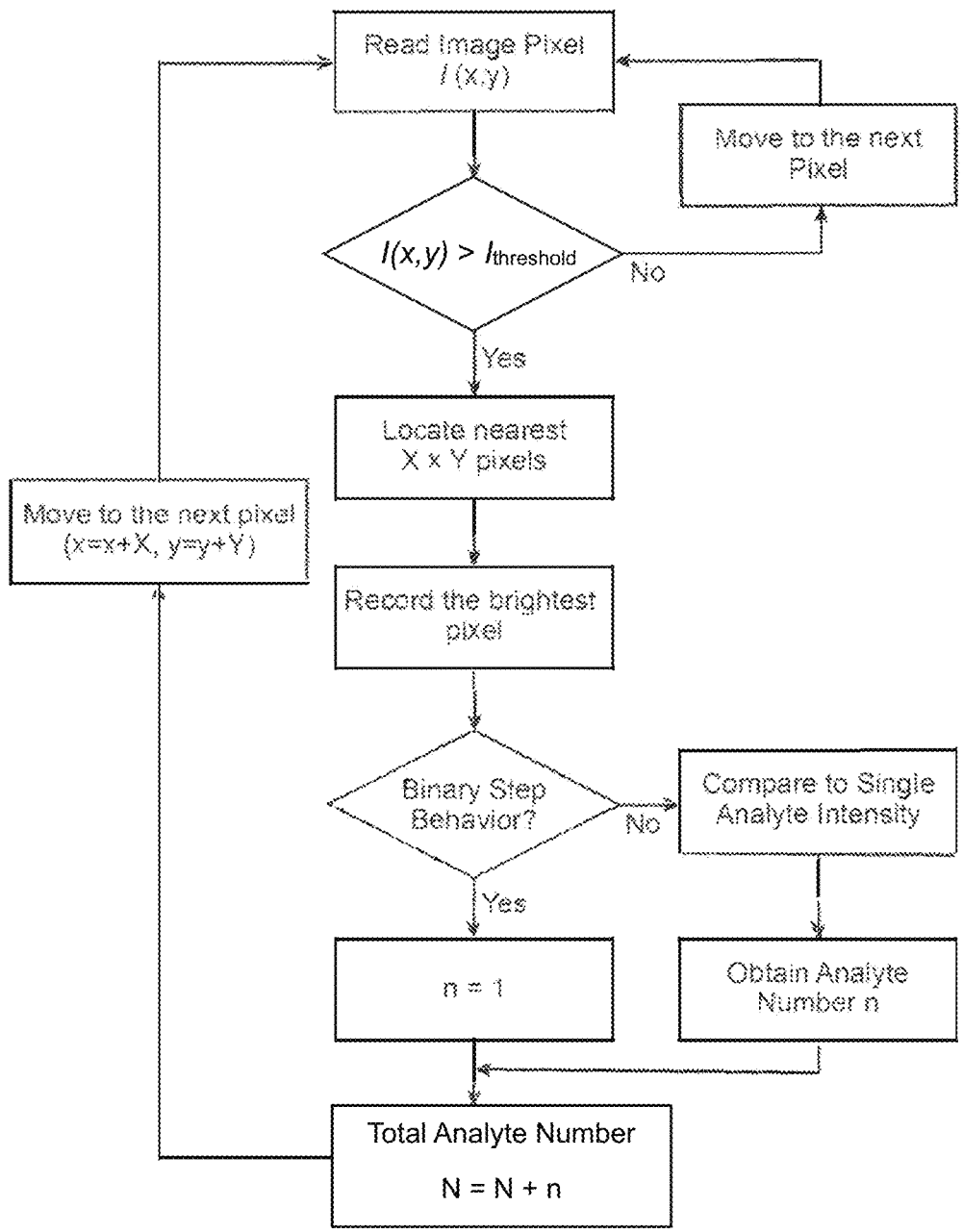
FIG. 3 is shows a flow chart of an embodiment of pixelated analyze (counting) process after reading the image.

The analysis includes to analyze the spatial, tempo, spectral information of the signal. The analysis includes statistical analysis, comparison, integration, and others. FIG. 3 shows a flow chart for one embodiment of this method. Some examples of the analysis are provided below.

The analysis method-1 includes (1) determine the local background signal intensity, (2) determine local signal intensity for one label, two labels, etc.; and (3) determine the total number of labels in the imaged area. The background signal means the signal that is generated under the exact conditions as other samples, except that the sample does not contain any targeted analytes.

Analysis-1 is based on using EM-CCD to record the spatial distribution bioassay signal intensity. It is used when discrete hot spot (bright pixels) on D2PA sensors are imaged.

(1) Determine the local background signal intensity. To determine the background signal, a reference sample is used. This reference sample is a D2PA sensor without any analyte immobilized and is imaged using the identical instrumentation set at identical experiment conditions for bioassays on D2PA. The intensities of all the pixels of the image are then plotted in a histogram, which gives the number of pixels at certain signal intensity. The signal intensity with the most corresponding pixel numbers is then determined as the background signal Background. This background intensities, together with their standard deviation (s.d.), is used to determine the threshold value defined to differentiate local background and local hot spot, which is Threshold=Background+n*s.d. Here n is an integer number used as a parameter to adjust the threshold value. Usually, n is set to 3, 5, or 7 in this work.

(2) For single bright pixel ($I_{x,y}$>Threshold), the local signal intensity of labels are determined using a two-step procedure. First, time-evolved imaging of a sample is used to find hot spot that has single labels (analyte). The total time of imaging is on the scale of 10 s of seconds and the resolution is on the scale of 10 s of milli-second. For hot spot of single analyte, a clear ON/OFF binary behavior of hot spot fluorescence intensity is observed. The pixels that displays such behavior are first counted as single labels/analyte. Their coordinate on the image and intensity is thus recorded. The averaged intensity of these hot pot is then used as the brightness of single label on D2PA assay.

Second, Bright pixels that does not show such binary behavior thus indicates multiple labels/analyte. We then compare their signal intensity to average brightness of single label to count the number of labels in local hot spot. Alternatively, another simplified procedure is utilized based on Poisson statistics principle. At low concentration of analyte (<1 pM), the probability of small amount of analyte 25 immobilized in the high density of plasmonic hot spot (~2.5×107 mm-2) observes Poisson distribution, which means the probability of more than two analyte being located in the same plasmonic hot spot is low. For example, at 1 fM of target analyte, the probability of more than two labels located within our imaging area, which contains more than 56,250 D2PA structures, is less than 0.01% (estimated). Therefore, it can be assumed that all bright hot spots that does not show single label behavior contains only two labels.

(3) After finishing (1) and (2), a list of hot spot pixel coordinates, intensities and corresponding label numbers can then be tabulated. The total number of labels can be obtained by SUM over the label numbers of each bright pixel.

The analysis-2 method includes (1) determine the local background signal spectrum, (2) determine local signal spectrum for one label, two labels, etc.; and (3) determine the total number of labels in the imaged area. Analysis-2 is based on using high-resolution spectrometer combined with a confocal microscope setup to record spatial distribution of bioassay signal spectra.

(1) To determine the background signal, a reference sample is used. This reference sample is a D2PA sensor without any analyte immobilized and is imaged using the identical instrumentation set at identical experiment conditions for bioassays on D2PA. A confocal microscope is then used to measure the local bioassay signal spectrum. The detection area is determined by the pin-hole size before the high-resolution spectrometer and the numerical aperture of the microscope objective lens. The confocal microscope raster scan the entire D2PA sensor to obtain the spatial distribution of background signal spectrum I(x,yJ). A histogram is then plotted which gives the number of pixels with a certain spectrum moment (fI(A)dA). Similarly to analysis-1 step (1), the spectrum moment with the most pixels are used as the background signal and their standard deviation is used to determine the threshold value: I(A)threshold=I(A)background+n*s.d(A). Here n is an integer number used as a parameter to adjust the threshold value. Usually, n is set equals to 3, 5, or 7 in this work. (2) To collect the spectrum of a single bright pixel, a confocal microscope setup coupled to a high resolution spectrometer is used. Read-out is performed similar to step (1). Since spectrum of a single molecule can only be reliably detected using high-sensitivity CCD with seconds of exposure time, which cannot provide enough time resolution to determine single labels' binary behavior in a hot spot. Thus to determine the number of labels at a bright pixel, we will compare the spectrum moment between different bright pixels. Due to the large amplification of D2PA sensor, single or multiple labels can be differentiated from background. Thus the number of analytes within the hot spot can be determined. (3) After finishing (1) and (2), a list of hot spot pixel coordinates, spectrum moments and corresponding label numbers can then be tabulated. The total number of labels can be obtained by SUM over the label numbers of each bright pixel. The analysis-3 (Sensing by Pixelated SERS signal) includes (1) determine the local background signal of "surface enhanced Raman scattering" (SERS) signature, (2) determine local SERS signal for one label, two labels, etc.; and (3) determine the total number of labels in the imaged area.

Analysis-3 is based on using high-resolution spectrometer combined with a confocal microscope setup to record spatial distribution of bioassay signal SERS spectra.

(1) To determine the background signal, a reference sample is used. This reference sample is a D2PA sensor without any analyte immobilized and is imaged using the identical instrumentation set at identical experiment conditions for bioassays on D2PA. A confocal microscope is then used to measure the local bioassay SERS spectrum. The detection area is determined by the pin-hole size before the high-resolution spectrometer and the numerical aperture of the microscope objective lens. The confocal microscope raster scan the entire D2PA sensor to obtain the spatial distribution of background signal spectrum I(x,y,cm-1). For a certain biomolecule, a histogram is then plotted which gives the number of pixels with the molecule's unique SERS signature intensity I(cm-1). Similarly to analysis-1 step (1), the spectrum moment with the most pixels are used as the background signal and their standard deviation is used to determine the threshold value: I(cm-1)threshold=I(cm-1) background+n*s.d(cm-1). Here n is an integer number used as a parameter to adjust the threshold value. Usually, n is set equals to 3, 5, or 7 in this work.

(2) To locate local hot spot, a confocal microscope setup is used to raster scan the entire D2PA sensor in a way similar to (1). Unlike analysis-1 or analysis-2, SERS is label free detection method and the single molecule SERS signal does not show binary behavior. Thus to determine the number of labels at a bright pixel, we will compare the SERS signature I(cm-1) between individual bright pixel. Due to the large amplification of D2PA sensor, single or multiple analyte can thus be differentiated from background. The number of analytes within the hot spot can then be determined.

(3) After finishing (1) and (2), a list of hot spot pixel coordinates, SERS signature intensity and corresponding label numbers can then be tabulated. The total number of labels can be obtained by SUM over the label numbers of each bright pixel.

A-6. Method of Sample Analysis with Pixelated Counting

Figure 4:
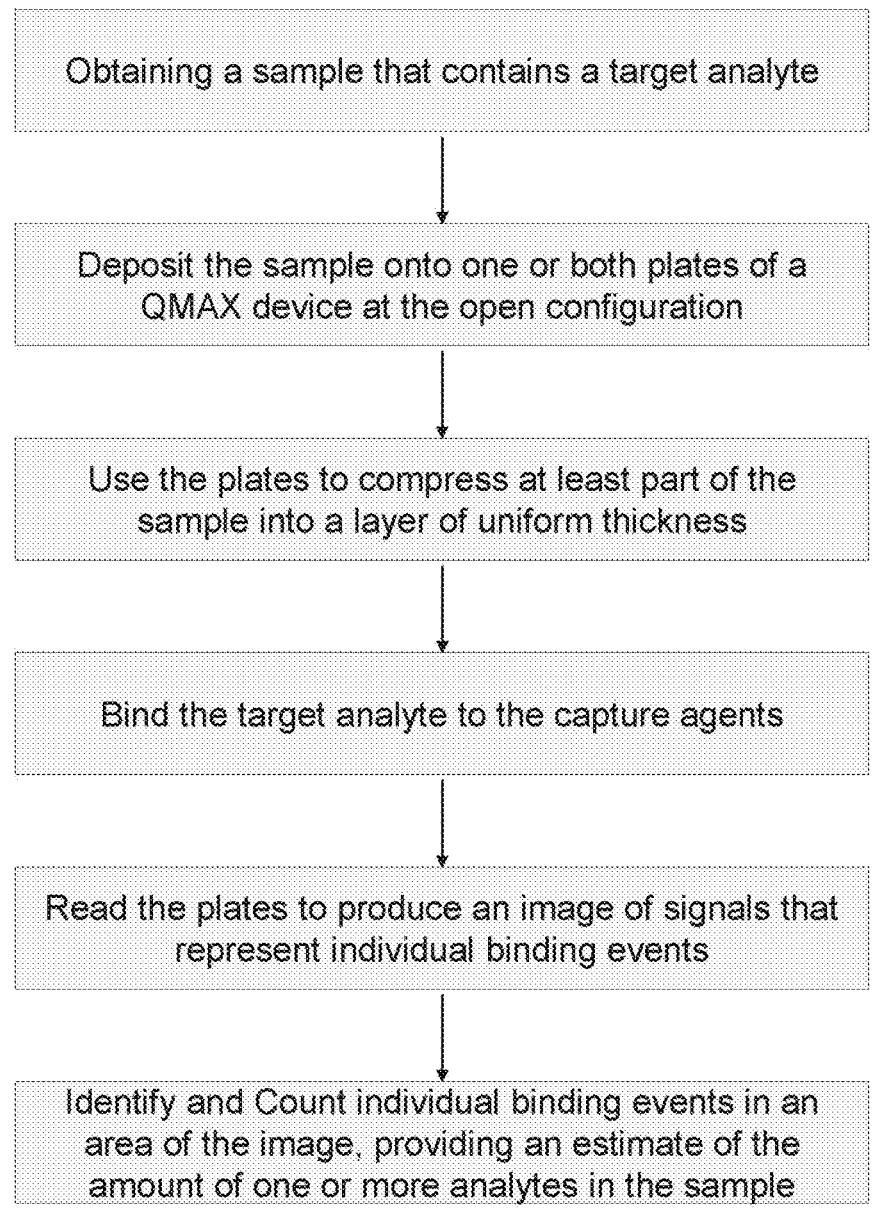
FIG. 4 is a flow chart showing the basic steps in an exemplary process for conducting an assay using the QMAX device, read by pixelated reading method.

Another aspect of the present invention is to provide a method of sample analysis with pixelated counting, as illustrated in FIG. 4, comprising the steps of:

(a) obtaining a sample that contains an analyte;

(b) obtaining a QMAX device;

(c) depositing the sample on one or both of the plates at the open configuration;

(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:

bringing the two plates together; and conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers;

(e) binding target analytes to capture agents while the plates are the closed configuration;

(f) reading the plates with a reading device to produce an image of signals that represent individual binding events; and (g) identifying and counting individual binding events in an area of the image, thereby providing an estimate of the amount of one or more analytes in the sample.

In some embodiments, a conformable pressing is a method that makes the pressure applied over an area is substantially constant regardless the shape variation of the outer surfaces of the plates.

In some embodiments, the parallel pressing applies the pressures on the intended area at the same time, and a sequential pressing applies the pressure on a part of the intended area and gradually move to other area.

In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

In some embodiments, for the method of the present invention, the sample is deposited on the first plate. In certain embodiments, before step (e) after step (d), the sample is incubated on the first plate for a predetermined period of time. In certain embodiments, the predetermined period of time is equal to or longer than the time needed for the binding between the capture antibody and the analyte to reach an equilibrium. In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

In some embodiments, for the method of the present invention, after step (e), the inner surface of the first plate can be washed to remove unbound molecules. For this approach, washing is conducted before switch the plates into the closed configuration. In some embodiments, for the method of the present invention, before step (e) and after step (d), before step (f) and after step (e), the plates can be switched into the open configuration (e.g. by removing the second plate) and the inner surface of the first plate can be washed. For this approach, washing is conducted before switch the plates into the closed configuration. In certain embodiments, such a step reduces non-specific binding and reduce signal noise. In certain embodiments, each of the wash step includes only one or multiple washes. In some embodiments, both of the washing steps are conducted. In some embodiments, only one of the washing steps is conducted.

In some embodiments, the inner surface can be washed with washing solution absorbed in a sponge. In some embodiments, the washing is conducted by squeezing the sponge to release the wash solution onto the inner surface of the first plate and releasing the sponge to reabsorb the wash solution. In some embodiments, the washing improves the limit of detection (LOD) for the detectable signal.

A-7. Example-1

Figure 5:
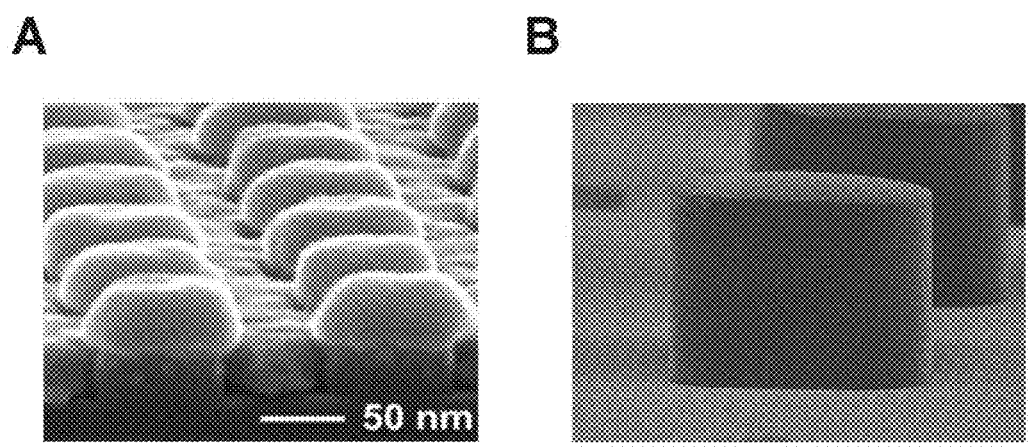
FIG. 5 shows SEMs of structures on first plate and second plate of an exemplary embodiment of a QMAX devices that employs a wash-free homogenous assay.
Figure 7:
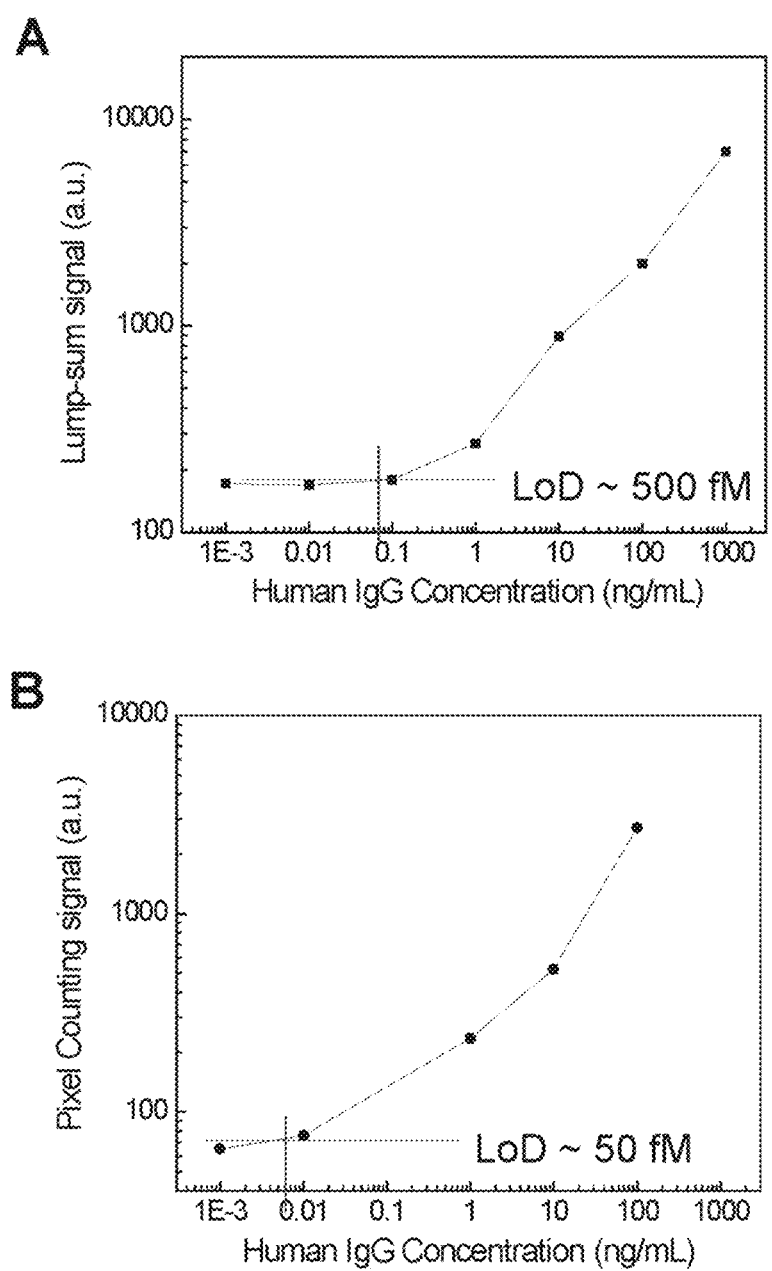
FIG. 7 shows examples of QMAX human IgG sandwich immunoassay with IR-800 label on M-Plate substrate (a) measured by lump-sum reading method (traditional reading method); and (b) measured by high sensitive electron multiplying charge coupled device (EMCCD), which is a pixelated reading method.

Referring to FIGS. 5-7, we experimentally demonstrated that pixelated reading improved the detection sensitivity in a sandwich immunoassay using a QMAX device.

The immunoassays in this experiment are a sandwich assay that utilized an immobilized capture antibody (goat anti-human IgG) to bind and immobilize a human IgG protein spiked in a PBS solution, which is then bound by a detection antibody (IR-800-conjugated mouse anti-human IgG), forming a sandwich-like structure. Both traditional "lump-sum" reading and pixelated counting methods were used to detect the immobilized IR-800 fluorescent signal and analyze the binding events, and their respective limit of detection (LoD) were calculated and compared based upon a series of assays with different human IgG concentrations.

Device Preparation:

In this experiment, the QMAX devices that we used comprised an X-plate and an M-plate, as shown in FIG. 5. The term "X-plate" as used herein refers to a plate with spacers fixed on one of its surfaces, wherein the spacers have a pre-determined uniform height and a constant inter-spacer distance. FIG. 5(B) shows an electromicroscopic image of an X-plate as used in this experiment. The X-plates were PMMA films of 25 mm×25 mm in area and 175 um in thickness, and the spacer arrays on the X-plates had pillar spacers of 30×40 um in lateral area and 30 um in height with 80 um inter-spacer distance.

The term "M-plate" as used herein refers to a plate that comprises: (a) substrate; and (b) a disk-coupled dots-on-pillar antenna (D2PA) structure. The terms "M-plate" and "D2PA" are interchangeable. FIG. 5 (A) shows an electromicroscopic image of an M-plate as used in this experiment. The M-plates were fabricated on a 500 um thick glass, and had a periodic nonmetallic pillar array with a period of 200 nm, pillar height of 55 nm and pillar diameter of 80 nm, a gold disk on top of each pillar with a thickness of 50 nm and a diameter of 100 nm, a gold backplane on the foot of the pillars, gold nanodots with 10 nm diameter randomly located on the pillar walls, and nanogaps between these metal components.

Furthermore, the M-plates were pre-treated with DSU (1 mM in Dioxane) overnight and then coated with Protein-A (10 ug/mL in PBS) for 2 hours. After the DSU coating, the M-plates were then coated with 10 ug/mL goat anti-human IgG in PBS) for 2 hours, washed with PBST for 3 times, and blocked with 2% BSA in PBS for 2 hours, washed with PBST for 3 times, and dried at 37° for 1 hour. As shown in FIG. 6 (A), DSU is used here functions as a molecular adhesion layer that attaches the capture antibody via protein-A (not shown in the figures) to the M-plate amplifying surface D2PA.

As shown in FIG. 6 (B), the X-plates were coated with IR-800-conjugated mouse anti-human IgG: before use, 200 uL antibody solution (10 ug/mL in PBS) was loaded and dried on the inner surface of the X-plate that comprises the spacers.

In some embodiments, the capture and detection antibody can be applied to the surface by printing, spraying, soaking or any other method that applies homogenous layer of capture reagents. In certain embodiments, the capture reagents are dried on the first plate.

Assay Steps:

For the assays, 1 uL sample solution (human IgG in PBS) with human IgG concentrations of 1 ug/mL, 100 ng/mL, 10 ng/mL, 1 ng/mL, 100 pg/mL, 10 pg/mL, or 1 pg/mL was loaded at different locations on the M-plate (25 mm×25 mm) inner surface. An X-plate (25 mm×25 mm) was pressed against the M-plate on top of the sample solution by hand. The assays were then incubated for 1 min, after which the X-plates were peeled off and M-plate was washed with PBST for 1 min and water for 1 min. Optical measurement was then taken with the M-plate.

For this approach, washing is conducted before switch the plates into the closed configuration. In certain embodiments, such a step reduces non-specific binding and reduce signal noise. In certain embodiments, each of the wash step includes only one or multiple washes. In some embodiments, both of the washing steps are conducted. In some embodiments, only one of the washing steps is conducted.

In some embodiments, the inner surface can be washed with washing solution absorbed in a sponge. In some embodiments, the washing is conducted by squeezing the sponge to release the wash solution onto the inner surface of the first plate and releasing the sponge to reabsorb the wash solution. In some embodiments, the washing improves the limit of detection (LOD) for the detectable signal.

Results:

FIG. 7 is plot of the experimental results from this experiment. Panel (A) shows the signal obtained by the "lump-sum" reading method, for which, a Raman microscopy with detection area of 200 um×200 um was used. As shown in the plot, the detected signal remained constantly low from 1 pg/mL to 100 pg/mL, and then increased as the human IgG concentration in the sample solution increased from 100 pg/mL to 1 ug/mL. However, enhanced sensitivity was observed with the pixelated counting method, as shown in panel (B), which was realized by imaging with electron multiplying charge coupled device EMCCD with a detection area of 200 um×200 um and analysis with a home-made image-processing software implemented with a pixelated reading algorithm.

LoD was determined as the IgG concentration corresponding to the fluorescent signal that is equal to the background optical noise plus three times of its standard deviation. Based on the acquired data, LoD for lump-sum reading method (red cross on the plot) was about 500 fM, while for pixelated counting method was reduced by 1 order to about 50 fM.

A-8. Example-2

Referring to FIGS. 8-12, we performed a different set of experiments that realized the pixelated reading method and demonstrated its advantages in sample analysis and analyte detection.

In the experiments described below, two different types of QMAX devices were tested in direct assays, in which streptavidin-coupled microspheres (fluorescence beads) were used as the nanoparticle label and human IgG-biotin antibody (IgG) as the binding agent.

Device preparation: One type of device tested here consisted of: a 3.5 mm×3.5 mm plain glass plate coated with gold on the surface (named "Au plate" herein), on which a layer of IgG was coated, a 5 mm×5 mm X-plate with pillar spacers of 30 μm uniform height, and 40 nm diameter streptavidin-coupled red fluorescent (580/605 nm) microspheres (40 nm streptavidin-beads). Another type of device consisted of: a 3.5 mm×3.5 mm plain glass plate with one surface coated with a layer of IgG, an X-plate (same as above), and 1 μm diameter streptavidin-coupled red fluorescent (580/605 nm) microspheres (1 μm streptavidin-beads). The term "X-plate" as used herein refers to part of the device of the present disclosure, the plate with spacers fixed on one of its surfaces, wherein the spacers have a pre-determined uniform height and a constant inter-spacer distance.

For Au plates, given that proteins do not bind to metal surface well, a self-assemble-monolayer (SAM) of dithiobis succinimidyl undecanoate (DSU) was used as the adhesion layer. First, Au plate was coated in DSU solution (1 mM in Dioxane) overnight at room temperature (RT). Second, after the formation of DSU adhesion layer, binding agent (human IgG-biotin) was bound to the plate. Briefly, 10 μL human IgG-biotin antibody (IgG) solution was dropped onto the gold surface of the Au plate to form a 1 mm thick layer for a 2-hour incubation at RT, and then washed away by PBST, which allowed the binding of IgG to the adhesion layer on the Au plate. Here the human IgG-biotin was dissolved in PBS solution in a series of concentrations from 1 μg/mL to 1 fg/mL, and each plate was coated with a pre-determined concentration of IgG. Last, 10 μL BSA (4% in PBS) was dropped onto the plate for a 2-hour blocking at RT and then washed away by PBST.

For plain glass plates, they were prepared following a similar protocol as for Au plates except that there was not a step of DSU coating due the efficient direct binding of proteins to glass, so that IgG and BSA were dropped onto the glass plate directly for binding agent coating and blocking.

Both 40 nm and 1 μm streptavidin-beads were kept in 1% (w/v) stock solution and added into BSA solution (4% in PBS) overnight at 4° C. for blocking, forming a working solution with a final concentration of beads at 0.1% (w/v). The final molar concentration for 40 nm beads is 50 nM, and for 1 μm beads is 32 pM.

Assay Steps:

For each assay with different plate and bead solution:

(1) 1 μL blocked bead solution was dropped onto the binding site of the assay plate (Au or glass plate);

(2) An X-plate was then put on top of the assay plate with the spacer pillars facing toward the deposited bead solution, and the two plates were pressed against each other by hand, and then left "self-held" in the closed configuration for a certain amount of time of assay incubation;

(3) After the incubation, the X-plate was peeled off and the assay plate was washed in PBST for 1 min and then in $H_2O$ for 1 min, after which fluorescence measurement was taken with the assay plate.

Results: FIGS. 8-11 show representative microscopic images taken by from the assays we performed, in which QMAX devices with the same human IgG concentration but different binding surface (Au plate or glass plate) were used and beads of different sizes (40 nm or 1 um) were loaded as the sample. FIG. 8 shows the images taken by EMCCD (A) and Nikon Camera (B) of 40 nm beads on Au plate (plate with gold surface). FIG. 9 shows the images taken by EMCCD (A) and Nikon Camera (B) of 40 nm beads on glass plate. FIG. 10 shows the images taken by EMCCD (A) and Nikon Camera (B) of 1 um beads on Au plate (plate with gold surface). FIG. 11 shows the images taken by EMCCD (A) and Nikon Camera (B) of 1 um beads on glass plate. Gold surface, as demonstrated by the images, served as a fluorescence signal enhancing layer that significantly increased the signal from both 40 nm beads and 1 um beads detected by either camera used in these experiments.

Figure 12:
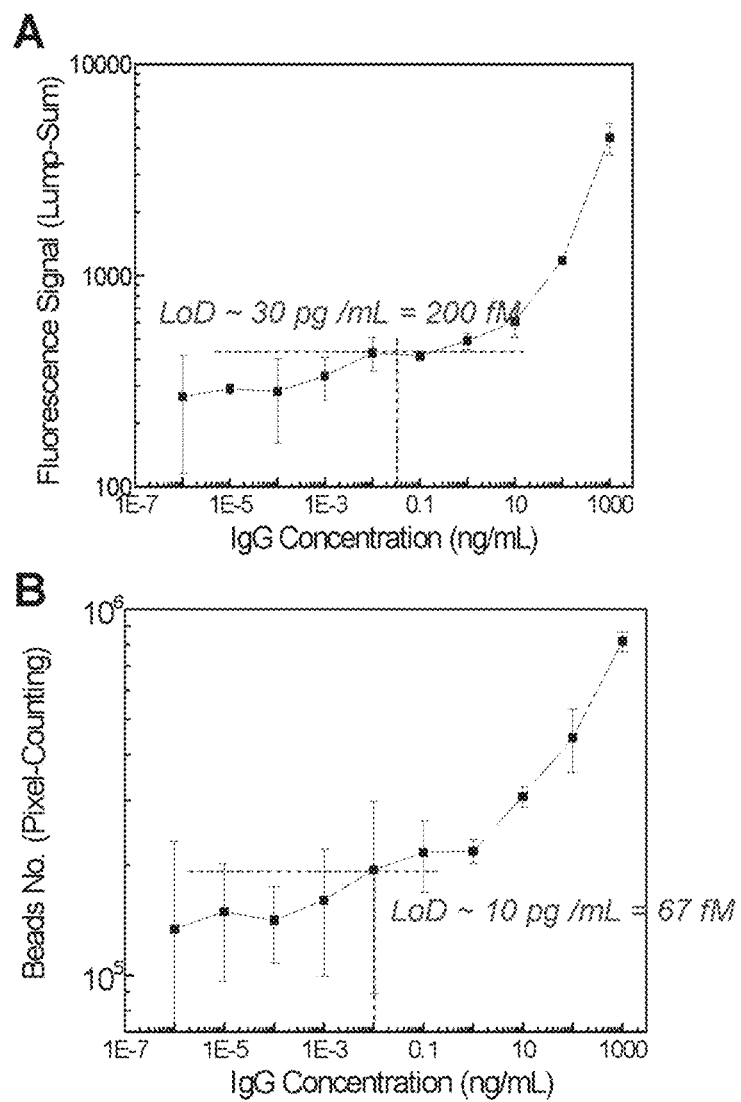
FIG. 12 shows examples of QMAX human IgG direct immunoassay with 40 nm beads label on gold substrate (a) measured by lump-sum reading method (traditional reading method); and (b) measured by high sensitive electron multiplying charge coupled device (EMCCD), which is a pixelated reading method.

FIG. 12 shows the relationship between measured fluorescence intensity and IgG concentration, as well as the limit of detection (LoD) in assays using Au plate and 40 nm beads with 1-min incubation time. Here, Au plates coated with different concentration of IgG were tested under the same condition, and fluorescent signal was detected using both "lump-sum" (a) and "pixel-counting" (b) methods. As shown in both plots, the fluorescent signal increased as a function of the concentration of IgG used to coat the plate. Under the experimental condition, LoD of IgG for the assay was around 15 pg/mL (100 fM) when the "lump-sum" method was used, and around 10 pg/mL (67 fM) when the "pixel-counting" method was used. Error bars are the standard deviation, calculated from the measurements at five different sample areas for each concentration.

Table A1 lists the raw data from the experiments that determined the LoD for assays using Au plate with 40 nm fluorescence beads and "pixel-counting" detection method. As demonstrated in Table A1, pixelated reading devices and methods as provided by the present invention enabled the estimation of total beads captured in the assays and analyses in many other aspects. In this table, "Total IgG coated" was calculated by multiplying the concentration and volume of the IgG solution used to prepare the plates, assuming all the IgG molecules in the solution were bound to the plate. "Average IgG distance" was then calculated by averaging the surface area of the Au plate over the number of IgG molecules. "Total Beads added" was calculated by multiplying the concentration and volume of the bead solution loaded to the Au plate during the assay. "Estimated Total Beads Captured" was estimated based on the pixel counting and the counting area. Two different types of "Capture Rate" were calculated, one is a quotient of "Estimated Total Beads Captured" and the number of "Total beads", and the other is a quotient of "Estimated Total Beads Captured" and the number of "Total IgG coated". "Captured beads average distance" was calculated by averaging the surface area of the Au plate over "Estimated Total Beads Captured".

TABLE A1

Raw data from LoD determination experiments with Au plates

| | Experimental Setup | | | | | | Experimental Results | | | |
|---|---|---|---|---|---|---|---|---|---|---|
| Chip Size | IgG Conc. (pM) | IgG volume | Total IgG coated | Average IgG distance (nm) | Beads Conc. (pM) | Total Beads added | Estimated Total Beads Captured | Capture Rate (Capture beads/ Total beads) | Capture Rate (Capture beads/ Total IgG) | Captured beads average distance (nm) |
| 3.5 mm × 3.5 mm LoD | 6.7E+03 | 10 ul | 4.0E+10 | 17 | 5.0E+04 | 1.1E+10 | 815360 | 0.0074% | 0.0020% | 3876 |
| | 6.7E+02 | 10 ul | 4.0E+09 | 55 | 5.0E+04 | 1.1E+10 | 445138 | 0.0040% | 0.0111% | 5246 |
| | 6.7E+01 | 10 ul | 4.0E+08 | 175 | 5.0E+04 | 1.1E+10 | 307796 | 0.0028% | 0.0767% | 6309 |
| | 6.7E+00 | 10 ul | 4.0E+07 | 552 | 5.0E+04 | 1.1E+10 | 218213 | 0.0020% | 0.5437% | 7493 |
| | 6.7E-01 | 10 ul | 4.0E+06 | 1747 | 5.0E+04 | 1.1E+10 | 216036 | 0.0020% | 5% | 7530 |
| | 6.7E-02 | 10 ul | 4.0E+05 | 5525 | 5.0E+04 | 1.1E+10 | 193822 | 0.0018% | 48% | 7950 |
| | 6.7E-03 | 10 ul | 4.0E+04 | 17471 | 5.0E+04 | 1.1E+10 | 160284 | 0.0014% | N.A | 8742 |
| | 6.7E-04 | 10 ul | 4.0E+03 | 55248 | 5.0E+04 | 1.1E+10 | 141120 | 0.0013% | N.A | 9317 |
| | 6.7E-05 | 10 ul | 4.0E+02 | 174709 | 5.0E+04 | 1.1E+10 | 148960 | 0.0013% | N.A | 9068 |
| | 6.7E-06 | 10 ul | 4.0E+01 | 552479 | 5.0E+04 | 1.1E+10 | 133716 | 0.0012% | N.A | 9571 |
| | Background | 10 ul | 0.0E+00 | 0 | 5.0E+04 | 1.1E+10 | 90596 | 0.0008% | N.A | 11628 |

A-9. Reasons (Mechanism) of Pixelated Reading has Better Sensitivity than Lumpsum Reading Consider following case as one example.

Both pixelated reading and lumpsum reading measure the signal from a same area (S) of one sample. The sample has very low concentration.

There are certain number ($n_s$) of hot spots have fluorescence signal ($l_s$) higher than surrounding background ($l_b$).

Each hot spots has an small area ($s_s$), while the total area is S (S>>$n_s$ $s_s$).

Pixelated reading measure and recognize the signal from each spots. The signal read by pixelated reading is $n_s$ $l_s$ or $s_s$ $l_s$. The background signal is recognized as $l_b$.

Thus the signal to noise ratio of pixelated reading is around $l_s/l_b$, which is much larger than 1.

However, lumpsum reading does not have the ability to recognize each spots, but measure and lump the signal from whole area. The signal read is $s_s$ $l_s$+S $l_b$. Consider S>>$s_s$, the signal reading is slightly larger $Sl_b$, while noise is $Sl_b$.

Thus the signal to noise ratio of lump-sum reading is close to 1.

Clearly, when measuring very low concentration of sample, the pixelated reading can provide much better sensitivity (signal to noise ratio) than lump-sum reading.

Examples of pixelated reading with QMAX immunoassay system shows: Pixel counting fluorescence detection method typically increase the assay limit of detection by 1-2 orders, which can be applied to QMAX assay system, but not only limit to QMAX assay system.

When combining pixel counting method with QMAX, achieve simple (one step), small volume (1 uL), fast (1 min), and high sensitive assay at the sample time.

The pixel counting measurement system is potable and simple. For example, when use beads and Au plate substrate, potentially can be read by DSRL camera and phone.

This platform can be adapted for any immunoassays that are performed in traditional micro titter plate and thus have broad applications.

A-10. Examples of Present Invention

Proximity-Dependent Signal Amplification Layer

The term "proximity-dependent signal amplification layer", "proximity-dependent signal amplification layer", or "surface signal amplification layer/surface" refers to a signal amplification layer that amplifies a signal from an analyte or a labeled analyte (e.g., a light-emitting label) in a proximity-dependent manner. In use of such a layer, the signal from an analyte or a labeled analyte increases the closer the molecule is to the surface of the signal amplification layer. As would be apparent, the magnitude of the signal produced by a first labeled molecule that is proximal to such a layer will be higher than the signal produced by a second labeled molecule that is distal to the layer. For example, the signal of a labeled molecule that is within 100 nm of a proximity-dependent signal amplification layer is greater than the signal of a labeled molecule that is 1 um or more away from the proximity-dependent amplification layer.

AA1. A method of sample analysis, comprising:
  (a) obtaining a sample that contains a target analyte;
  (b) obtaining a first and second plates that are movable relative to each other into different configurations and that have, on its respective surface, a sample contact area for contacting a sample that contains an analyte, wherein one of the sample contact areas on the first plate has a binding site that comprises:
    (i) proximity-dependent signal amplification layer as definition above, and
    (ii) capture agents that are attached to said proximity-dependent signal amplification layer and that bind the analyte;
  (c) depositing the sample on one or both of the plates when the plates are configured in an open configuration, in which the average spacing between the inner surfaces of the two plates is at least 200 um;
  (d) after (c), moving the two plates into a close configuration, in which, at least part of the sample is between the two plates and the average spacing between the inner surfaces of the plates is less than 200 um; and
  (e) reading the sample contact area with a reading device to produce an image of signals.

AB1. A device for analyzing a sample comprising:
  a first plate, a second plate, and a binding site, wherein
  (a) the first and second plats are movable relative to each other into different configurations, and have, on its respective surface, a sample contact area for contacting a sample that contains a target analyte,
  (b) one of the sample contact areas on the first plate has a binding site that comprises:
    (i) proximity-dependent signal amplification layer, and
    (ii) capture agents that are attached to said proximity-dependent signal amplification layer;
  wherein one of the configurations is an open configuration, in which the average spacing between the inner surfaces of the two plates is at least 200 um;
  wherein another of the configurations is a close configuration, in which, at least part of the sample is between the two plates and the average spacing between the inner surfaces of the plates is less than 200 um.

AC1. A system for analyzing a sample comprising:
  (a) a first plate and a second plate that are movable relative to each other into different configurations and that have, on its respective surface, a sample contact area for contacting a sample that contains a target analyte, wherein one of the sample contact areas on the first plate has a binding site that comprises:
    (i) proximity-dependent signal amplification layer, and
    (ii) capture agents that are attached to said proximity-dependent signal amplification layer;
  (b) a reading device for producing an image of signals emanating from the binding site of the first plate;
  (c) a device assembly that operably connects the reading device to a closed configuration of the first plate and second plate;
  (d) a memory for storing said image; and
  (e) programming for identifying and counting individual binding events in an area of the image;
  wherein the capture agents capture the target analyte.

Amplification Layer for Amplification Over the Sample Thickness

*The term "amplification layer" refers to a signal amplification layer that amplifies a signal from an analyte or a labeled analyte (e.g., a light-emitting label) over the sample thickness. For example, if the sample layer thickness is 30 um, the amplification layer can amplify the signal of a analyte and/or a label of the analyte in the sample.

NAA1. A method of sample analysis, comprising:
  (a) obtaining a sample that contains a target analyte;
  (b) obtaining a first and second plates that are movable relative to each other into different configurations and that have, on its respective surface, a sample contact area for contacting a sample that contains an analyte, wherein one of the sample contact areas on the first plate has a binding site that comprises:
- (i) amplification layer, and
- (ii) capture agents that are attached to said amplification layer and that bind the analyte;

(c) depositing the sample on one or both of the plates when the plates are configured in an open configuration, in which the average spacing between the inner surfaces of the two plates is at least 200 um;

(d) after (c), moving the two plates into a close configuration, in which, at least part of the sample is between the two plates and the average spacing between the inner surfaces of the plates is less than 200 um; and (e) reading the sample contact area with a reading device to produce an image of signals.

NAB1. A device for analyzing a sample comprising:
a first plate, a second plate, and a binding site, wherein
- (c) the first and second plats are movable relative to each other into different configurations, and have, on its respective surface, a sample contact area for contacting a sample that contains a target analyte,
- (d) one of the sample contact areas on the first plate has a binding site that comprises:
  - (i) amplification layer, and
  - (ii) capture agents that are attached to said amplification layer;

wherein one of the configurations is an open configuration, in which the average spacing between the inner surfaces of the two plates is at least 200 um;

wherein another of the configurations is a close configuration, in which, at least part of the sample is between the two plates and the average spacing between the inner surfaces of the plates is less than 200 um.

NAC1. A system for analyzing a sample comprising:
- (a) a first plate and a second plate that are movable relative to each other into different configurations and that have, on its respective surface, a sample contact area for contacting a sample that contains a target analyte, wherein one of the sample contact areas on the first plate has a binding site that comprises:
  - (i) amplification layer, and
  - (ii) capture agents that are attached to said amplification layer;
- (b) a reading device for producing an image of signals emanating from the binding site of the first plate;
- (c) a device assembly that operably connects the reading device to a closed configuration of the first plate and second plate;
- (d) a memory for storing said image; and
- (e) programming for identifying and counting individual binding events in an area of the image;

wherein the capture agents capture the target analyte.

AA2. The method of embodiment AA1, wherein the method is a homogeneous assay that the signal is read without using a wash step to remove any biological materials or labels that are not bound to the capture agent at the binding site.

AA3. The method of embodiment AA1, wherein the method further comprises (f) quantifying a signal in an area of the image to providing an estimate of the amount of one or more analytes in the sample.

AA4. The method of embodiment AA3, wherein step (f) comprises identifying and counting individual binding events between an analyte with a capture agents in an area of the image, thereby providing an estimate of the amount of one or more analytes in the sample.

AA5. The method of embodiment AA3, wherein step (f) comprises quantifying a lump-sum signal in an area of the image, thereby providing an estimate of the amount of one or more analytes in the sample.

NAB1.1 The devices, systems or methods of embodiment NAB1, NAC1, or NAA1, wherein the amplification layer comprises a layer of metallic material.

NAB1.2 The devices, systems or methods of embodiment NAB1, NAC1, or NAA1, wherein the amplification layer comprises a layer of metallic material and a dielectric material on top of the metallic material layer, wherein the capture agent is on the dielectric material.

The devices, systems or methods of embodiment NAB1.1 or NAB1.2, wherein the metallic material layer is a uniform metallic layer, nanostructured metallic layer, or a combination.

The devices, systems or methods of embodiment NAB1, NAC1, or NAA1, wherein the amplification layer comprises a layer of metallic material and a dielectric material on top of the metallic material layer, wherein the capture agent is on the dielectric material, and the dielectric material layer has a thickness of 0.5 nm, 1 nm, 5 nm, 10 nm, 20 nm, 50 nm, 00 nm, 200 nm, 500 nm, 1000 nm, 2 um, 3 um, 5 um, 10 um, 20 um, 30 um, 50 um, 100 um, 200 um, 500 um, or in a range of any two values.

AA6. The devices, systems or methods of any prior claim, wherein the sample contact area of the second plate has a reagent storage site.

AA7. The devices, systems or methods of any prior claim, wherein the sample contact area of the second plate has a reagent storage site, and the storage site is, in a closed configuration, approximately above the binding site on the first plate.

AA8. T The devices, systems or methods of any prior claim, wherein the sample contact area in the first plate further comprises a reagent storage site.

AA9. The devices, systems or methods of any prior claim, wherein the sample contact area in the first plate further comprises a reagent storage site, wherein the reagent storage site is not in the same location of the sample contact area as that of the binding site.

AA10. The devices, systems or methods of any prior claim, wherein the reagent in the reagent storage site is a detection agent that binds to the target analyte.

AA11. T The devices, systems or methods of any prior claim, wherein the method further comprises a step of labeling the target analyte with a detection agent.

AA12. The devices, systems or methods of any prior claim, wherein the detection agent comprises a label.

AA13. The devices, systems or methods of any prior claim, wherein the capture agent and detection agent both bind to the target analyte to form a sandwich.

AA14. The method of embodiment AA9, wherein the method further comprises measuring the volume of the sample in the area imaged by the reading device.

AA15. The method of embodiment AA9, wherein the first place comprises a plurality of binding sites that each comprise:
- (i) proximity-dependent signal amplification layer, and
- (ii) capture agents that are attached to the proximity-dependent signal amplification layer.

AA16. The method of embodiment AA1, wherein the target analyte is a protein, peptide, DNA, RNA, nucleic acid, small molecule, cell, or nanoparticle.

AA17. The method of any prior embodiment, wherein the capture agent specifically binds to the target analyte.

AA18. The method of any prior embodiment, wherein the image shows the position, local intensity, and local spectrum of the signals.

AA19. The method of any prior embodiment, wherein the signals are luminescence signals selected from the group consisting of fluorescence, electroluminescence, chemiluminescence, and electrochemiluminescence signals.

AA20. The method of any prior embodiment, wherein the signals are Raman scattering signals.

AA21. The method of any prior embodiment, wherein the signals are the forces due to local electrical, local mechanical, local biological, or local optical interaction between the plate and the reading device.

AA22. The method of any prior embodiment, wherein before the step (b), it further comprises a step of labeling the target analytes with a label, either prior to or after they are bound to said capture agent.

AA23. The method of any prior embodiment, wherein the reading step (b) is performed by applying a voltage bias between said signal amplification layer and another electrode, thereby providing greater sensitivity.

AA24. The method of any prior embodiment, wherein the identifying and counting step (c) comprises: (1) determining the local intensity of background signal, (2) determining local signal intensity for one label, two labels, three labels, and four or more labels; and (3) determining the total number of labels in the imaged area.

AA25. The method of any prior embodiment, wherein the identifying and counting step (c) comprises: (1) determining the local spectrum of background signal, (2) determining local signal spectrum for one label, two labels, three labels, and four or more labels; and (3) determining the total number of labels in the imaged area.

AA26. The method of any prior embodiment, wherein the identifying and counting step (c) comprises: (1) determining the local Raman signature of background signal, (2) determining local signal Raman signature for one label, two labels, three labels, and four or more labels; and (3) determining the total number of labels in the imaged area.

AA27. The method of any prior embodiment, wherein the identifying and counting step comprises determining one or more of the local intensity, spectrum, and Raman signatures.

AA28. The method of any prior embodiment, wherein the binding step (a) is accelerated by applying an electric field to the plate, thereby moving the analytes to the proximity-dependent signal amplification layer.

AA29. The method of any prior embodiment, wherein the proximity-dependent signal amplification layer comprises a D2PA.

AA30. The method of any prior embodiment, wherein the proximity-dependent signal amplification layer comprises one or a plurality of metallic discs and a significantly flat metallic film, wherein a substantial portion of the metallic disc has a separation from the metallic film and the separation and the dimensions of the disks are less than the wavelength of the light used in sensing.

AA31. The method of embodiment AA30, wherein the metallic disk has a shape selected from the group of shapes consisting of round, polygonal, pyramidal, elliptical, elongated bar shaped, or any combination thereof.

AA32. The method of embodiment AA30, wherein the separation is 0.5 to 30 nm, and wherein the discs have an average lateral dimension in the range of 20 nm to 250 nm.

AA33. The method of any prior embodiment, wherein the capture agents are attached to the proximity-dependent signal amplification layer through a molecular linking layer that links said capture agents with said proximity-dependent signal amplification layer.

AA34. The method of any prior embodiment, wherein the signals are light signals.

AA35. The method of any prior embodiment, wherein the signals are produced by a fluorescent label, that is associated with the bound analyte, either before or after binding of the analyte to the capture agent.

AA36. The method of any prior embodiment, wherein the average distance between the two adjacent signals being read to form the image of signals in reading step (c) is greater than 10 nm.

AA37. The method of any prior embodiment, wherein the signals are signals generated by Raman scattering.

AA38. The method of any prior embodiment, wherein the capture agent is an antibody.

AA39. The method of any prior embodiment, wherein the capture agent is a polynucleotide.

AC2. The system of embodiment AC1, wherein the reading device is the camera of a handheld mobile communication device.

AC3. The system of any prior AC embodiment, wherein the device assembly is an adaptor that connects to a camera of a handheld mobile communication device.

AC4. The system of any prior AC embodiment, wherein the signals represent individual target-analyte binding events.

AC5. The system of any prior AC embodiment, wherein the device assembly controls or changes the relative position between the plate and the reading device, in at least one of the three (x, y, z) orthogonal directions, for reading the signal.

AC6. The system of any prior AC embodiment, wherein the reading device is a CCD camera.

AC7. The system of any prior AC embodiment, wherein the reading device is a photodetector comprising one or more other optical devices that are selected from optical filters, spectrometer, lenses, apertures, beam splitter, mirrors, polarizers, waveplates, and shutters.

AC8. The system of any prior AC embodiment, wherein the reading device collects the position, local intensity, local spectrum and local Raman signature of said signals.

AC9. The system of any prior AC embodiment, wherein the programming comprises programming for: (1) determining the local intensity or spectrum or Raman signature of background signal, (2) determining local signal intensity or spectrum or Raman signature for one label, two labels, three labels, and four or more labels; and (3) determining the total number of labels in the imaged area.

AC10. The system of any prior AC embodiment, wherein the identifying and counting comprises determining of any, some or all of the local intensity, spectrum, and Raman signatures.

AC11. The system of any prior AC embodiment, wherein said system comprises a source of light, electricity, or chemical for exciting labels on the surface of said plate.

AC12. The system of any prior AC embodiment, wherein said system comprises an electrode for applying a voltage between the electrode and the proximity-dependent signal amplification layer for generating an electric field and/or electrical field gradient that either (a) moves analytes that have been placed in solution on the surface of the plate to the capture agents on the proximity-dependent signal amplification layer.

AC13. The system of any prior AC embodiment, wherein said system comprises an electrode for applying a voltage bias between said signal amplification layer and another electrode to further improve sensitivity.

AC14. The system of any prior AC embodiment, wherein the reading device is an electric or mechanical or biological probe that collects the position, local electrical, local mechanical, local biological, and local optical interaction between the plate and the reading device.

The devices or methods of any prior embodiment, wherein the signal related to the analyte captured by the capture agent comes from (i) a detection agent that is captured by the analyte, (ii) an analyte that is captured by the binding site, or (iii) both (i) and (ii).

The devices or methods of any prior embodiment, wherein the measuring of the signal related to the analyte captured by the capture agent is a measurement of electrical, optical, or a combination.

B. Homogenous Assay Using QMAX Device

B-1. Examples of Wash-Free Homogenous QMAX Devices

Figure 13:
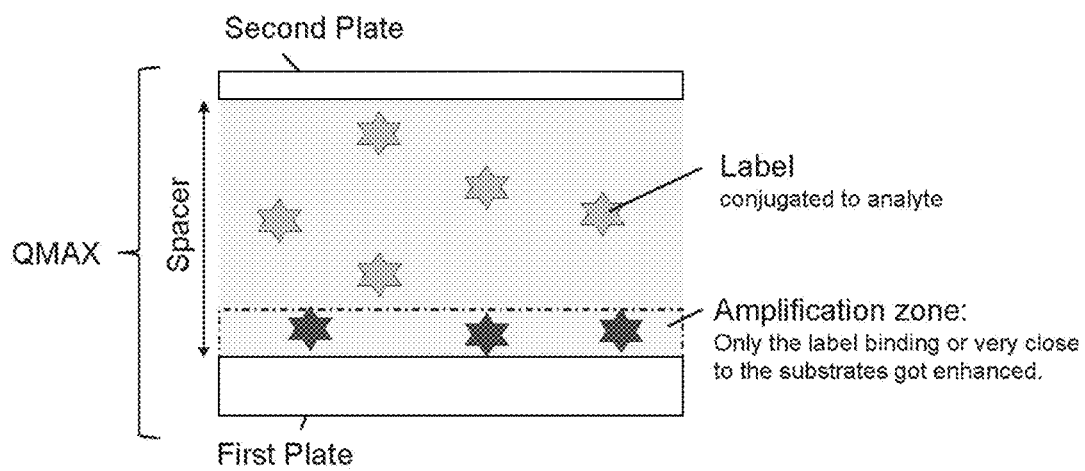
FIG. 13 is a schematic drawing for an exemplary embodiment of a QMAX (Q: quantification; M: magnifying; A: adding reagents; X: acceleration; also known as compressed regulated open flow (CROF)) device that employs a wash-free homogenous assay.

FIG. 13 shows an embodiment of a wash-free homogenous QMAX (Q: quantification; M: magnifying; A: adding reagents; X: acceleration; also known as compressed regulated open flow (CROF)) device, which comprises a first plate (In some embodiments marked as "substrate"), a second plate (In some embodiments marked as "X-plate"). In the space between the first plate and second plate, the sample contains label conjugated to the target analyte contacts both plates. The substrate is coated capture analyte to capture the target analyte. Near the top surface of substrate, there is an amplification zone, where only the label binding or very close to the substrates got enhanced.

The plates are moveable relative to each other into different configuration. One of the configurations is an open configuration, in which the two plates are partially or entirely separated apart and the spacing between the plates are not regulated by the spacers. In some embodiments, the inner surface of a respective plate comprises a sample contact area, which occupies a part of the entirety of the inner surface. In certain embodiments, the spacers are positioned within the sample contact area. In some embodiments, the spacers are not fixed to any one of the plates, but are mixed in the sample.

The sample is any liquid that needs testing. In some embodiments, the sample is a body fluid that is with or without processing or dilution. For example, the body fluid can be whole blood, blood plasma, serum, urine, saliva, sweat, or breath condensate. In some embodiments, the sample is blood. In certain embodiments, the sample comprises plasma. In certain embodiments, the sample comprises whole blood. In certain embodiments, the sample is a blood or plasma that has been diluted with buffer for 0.5, 1, 2, 3, 4, 5, 6, 7, 8, 9, 10, 20, 30, 40, 50, 60, 70, 80, 90, 100, 200, 300, 400, 500, 600, 700, 800, 900, 1,000, 5,000, 10,000, 50,000, 100,000, 500,000, or 1,000,000 times or in a range between any of the two values. In some embodiments, the sample comprises an analyte, which can be any cell or molecule that can be detected and quantified. In certain embodiments, the analyte is a cell that expresses specific antibodies or antibody paratopes on its surface. In certain embodiments, the analyte is a cell that expresses specific antigens or epitopes on its surface. In certain embodiments, the analyte is a protein, peptide or other molecule that can be recognized by an antibody or a series of antibodies. For example, in certain embodiments the analyte is an antigen or comprises an antigen epitope. In certain embodiments, the analyte is an antibody or comprises an antibody paratope.

The term "sample" as used herein relates to a material or mixture of materials containing one or more analytes of interest. In particular embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient.

The label is a light-emitting label or an optical detectable label, directly or indirectly, either prior to or after it is bound to said capture agent. The label is label with signal of Raman scattering, chromaticity, luminescence, fluorescence, electroluminescence, chemiluminescence, and/or electrochemiluminescence. As used herein, the term "light-emitting label" refers to a label that can emit light when under an external excitation. This can be luminescence. Fluorescent labels (which include dye molecules or quantum dots), and luminescent labels (e.g., electro- or chemiluminescent labels) are types of light-emitting label. The external excitation is light (photons) for fluorescence, electrical current for electroluminescence and chemical reaction for chemiluminscence. An external excitation can be a combination of the above. The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

The amplification layer amplifies a signal from the target analyte or a label of the target analyte when the target analyte or label is 1 nm, 10 nm, 20 nm, 30 nm, 40 nm, 50 nm, 60 nm, 70 nm, 80 nm, 90 nm, 100 nm, 200 nm, 300 nm, 400 nm, 500 nm, 1 um, 2 um, 5 um, 10 um from the amplification layer, or a range between any two of the values; and a preferred range of 1 nm to 50 nm, 50 nm to 100 nm, 100 nm to 200 nm, 200 nm to 500 nm.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

In some embodiments, the proximity-dependent signal amplification layer includes, but not limited to, the proximity-dependent signal amplification layers described in U.S. Provisional Patent Application No. 61/347,178, which was filed on May 21, 2010, U.S. Provisional Patent Application No. 61/622,226, which was filed on Apr. 10, 2012, U.S. Provisional Patent Application No. 61/708,314, which was filed on Oct. 1, 2012, U.S. Provisional Patent Application No. 61/800,915, which was filed on Mar. 15, 2013, U.S. Provisional Patent Application No. 61/801,933, which was filed on Mar. 15, 2013, U.S. Provisional Patent Application No. 61/801,096, which was filed on Mar. 15, 2013, U.S. Provisional Patent Application No. 61/801,424, which was filed on Mar. 15, 2013, U.S. Provisional Patent Application No. 61/794,317, which was filed on Mar. 15, 2013, U.S. Provisional Patent Application No. 62/090,299, which was filed on Dec. 10, 2014, U.S. Provisional Patent Application No. 62/066,777, which was filed on Oct. 21, 2014, U.S. Provisional Patent Application No. 62/234,538, which was filed on Sep. 29, 2015, U.S. Utility patent application Ser. No. 13/699,270, which was filed on Jun. 13, 2013, U.S. Utility patent application Ser. No. 13/838,600, which was filed on Mar. 15, 2013, U.S. Utility patent application Ser. No. 14/459,239, which was filed on Aug. 13, 2014, U.S. Utility patent application Ser. No. 14/459,251, which was filed on Aug. 13, 2014, U.S. Utility patent application Ser. No. 14/852,412, which was filed on Mar. 16, 2014, U.S. Utility patent application Ser. No. 14/871,678, which was filed on Sep. 30, 2015, U.S. Utility patent application Ser. No. 14/431,266, which was filed on Oct. 5, 2015, U.S. Utility patent application Ser. No. 14/668,750, which was filed on Mar. 25, 2015, U.S. Utility patent application Ser. No. 14/775,634, which was filed on Sep. 11, 2015, U.S. Utility patent application Ser. No. 14/775,638, which was filed on Sep. 11, 2015, U.S. Utility patent application Ser. No. 14/852,417, which was filed on Sep. 11, 2015, U.S. Utility patent application Ser. No. 14/964,394, which was filed on Dec. 9, 2015, PCT Application (designating U.S.) No. PCT/US2011/037455, which was filed on May 20, 2011, PCT Application (designating U.S.) No. PCT/US2013/032347, which was filed on Mar. 15, 2013, PCT Application (designating U.S.) No. PCT/US2013/062923, which was filed on Oct. 1, 2013, PCT Application (designating U.S.) No. PCT/US2014/030108, which was filed on Mar. 16, 2014, PCT Application (designating U.S.) No. PCT/US2014/029675, which was filed on Mar. 14, 2014, PCT Application (designating U.S.) No. PCT/US2014/028417, which was filed on Mar. 14, 2014, PCT Application (designating U.S.) No. PCT/US2014/029979, which was filed on Mar. 15, 2014, PCT Application (designating U.S.) No. PCT/US2015/056518, which was filed on Oct. 20, 2015, PCT Application (designating U.S.) No. PCT/US2016/054025, which was filed on Sep. 27, 2016, the complete disclosures of which are hereby incorporated by reference for all purposes.

The signal amplification layer comprises a continuous metallic film that is made of a material selected from the group consisting of gold, silver, copper, aluminum, alloys thereof, and combinations thereof. The signal amplification layer comprises high-amplification regions and low-amplification regions, wherein the high-amplification regions amplify signals at said surface more than the low-amplification regions, wherein the low-amplification regions of the layer have been selectively masked, wherein the signal amplification layer comprises (i) two or more protrusions, (ii) two or more metal metallic structures, and (iii) two or more gaps between the metallic structures; thereby increasing the probability that a target analyte will bind to a high-amplification region and be detected.

The signal amplification layer comprising:
(i) a substantially continuous metallic backplane on the substrate;
(ii) one or a plurality of dielectric or semiconductor pillars extending from the metallic backplane or from the substrate through holes in the backplane; and
(iii) a metallic disk on top of the pillar, wherein at least one portion of the edge of the disk is separated from the metallic backplane by a gap;

wherein the gap(s) and portion of the metal edges are a part of the high signal amplification area, wherein the metallic disk has a shape selected from the group of shapes consisting of round, polygonal, pyramidal, elliptical, elongated bar shaped, or any combination thereof. The metallic disc is separated from the metallic film by a distance in the range of 0.5 to 30 nm, and the average lateral dimension of the discs is in the range of 20 nm to 250 nm; wherein the signal amplification layer comprises one or more metallic discs has a shape selected from the group of shapes consisting of round, polygonal, pyramidal, elliptical, elongated bar shaped, or any combination thereof, wherein the average lateral dimension of the discs is in the range 20 nm to 250 nm, and the gap between adjacent discs in the range of 0.5 to 30 nm.

wherein the metallic structures are made of a material that is selected from the group consisting of gold, silver, copper, aluminum, alloys thereof, and combinations thereof.

wherein the pillars are periodic or aperiodic, or the metallic structures have a random shape.

wherein the signal that is amplified is Raman scattering, chromaticity, luminescence, fluorescence, electroluminescence, chemiluminescence, and/or electrochemiluminescence.

QMAX device's first plate further comprising a molecular linking layer that links said capture agents with said signal amplification layer, wherein said molecular adhesion layer is a self-assembled monolayer (SAM), wherein each molecule of the SAM comprises three parts: (i) a head group that has specific affinity to the signal amplification layer, (ii) a terminal group that specific affinity to the capture agent, and (iii) a linker that links the head group and terminal group, wherein the length of the linker determines the average spacing between the metal signal amplification layer and an attached capture agent can affects light amplification of the device.

QMAX device's second plate sample contact area comprises a storage site containing detection agents that upon contacting the sample, dissolves into the sample and diffuses in the sample, wherein each capture agent, target analyte and corresponding detection agent is capable of forming a capture agent-target analyte-detection agent sandwich in a binding site of the first plate.

The device of any prior paragraph, wherein the second plate sample contact area comprises a storage site containing detection agents that upon contacting the sample, dissolves into the sample and diffuses in the sample, wherein the detection agent binds to the capture agent and competitively inhibits the binding between the capture agent and the target analyte.

B-2. Examples of First Plate and Second Plate of Wash-Free Homogenous QMAX Devices FIG. 14 shows SEMs of structures on first plate and second plate of an exemplary embodiment of a QMAX devices that employs a wash-free homogenous assay.

(a) The first plate is called "M-Plate" fabricated on 500 um thick glass is a periodic nonmetallic pillar array with a period 200 nm, pillar height 55 nm and pillar diameter 80 nm, a gold disk on top of each pillar with a thickness 50 nm and diameter 100 nm, a gold backplane on the foot of the pillars, gold nanodots with 10 nm diameter randomly located on the pillar walls, and nanogaps between these metal components.

The M-Plate increase the signal intensity of Raman and/or fluorescence label in the magnitude of a signal, e.g., at least a 10-fold increase, at least a 100-fold increase at least a 1,000-fold increase, at least a 10,000-fold increase, or at least a 100,000-fold increase in a signal.

(b) The second plate is called "X-Plate", which is a micro-pillar array with 30×40 um pillar size, 80 um inter spacing distance and 30 um pillar height, made on 175 um thick PMMA film.

B-3. Amplification Simulation Near the First Plate (M-Plate)

Figure 15:
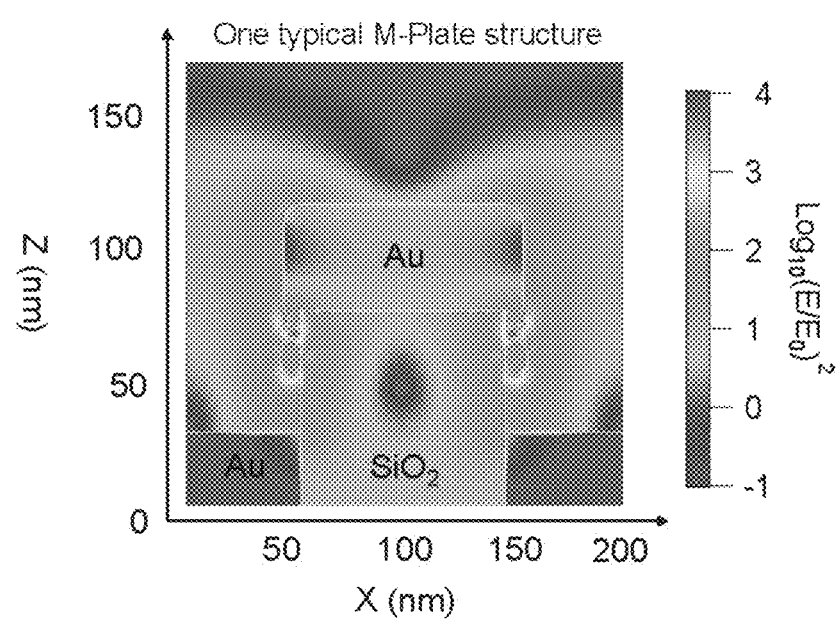
FIG. 15 shows simulation of two-dimensional map of the electric field square $|E|^2$ near the structure of second plate from a commercial finite-difference time-domain (FDTD) simulation software.

FIG. 15 shows simulation of two-dimensional map of the electric field square $|E|^2$ near the structure of second plate from a commercial finite-difference time-domain (FDTD) simulation software. To study the fluorescence enhancement near the M-Plate, a commercial finite-difference time-domain (FDTD) simulation software was used. Simulation of electric field near the M-Plate (electric field square intensity is proportional to the fluorescence amplification). Two-dimensional map of the electric field square $|E|^2$. The electric fields are concentrated and significantly enhanced around the M-Plate within 100 nm range, particularly in the regions of nanogap and around the nanodot of M-Plate.

This M-Plate in simulation, is on 500 um thick glass is a periodic nonmetallic pillar array with a period 200 nm, pillar height 75 nm and pillar diameter 80 nm, a gold disk on top of each pillar with a thickness 40 nm and diameter 100 nm, a gold backplane on the foot of the pillars, two gold nanodots with 10 nm diameter located on the pillar walls, and nanogaps between these metal components.

In this embodiment, the enhancement mechanism of fluorescence label is known as Plasmonic enhancement. The enhanced fluorescence intensity due to the proximity of metal nanostructures makes it possible to detect much lower concentrations of biomarkers tagged with fluorescence molecule either in sensing format or for tissue imaging. Metal enhanced fluorescence (MEF) arises from an increased excitation rate due to an enhanced local field experienced by the fluorophore, and the electromagnetic coupling of the fluorophore with the near-by metal nanoparticle. Therefore, metal nanostructures are able to produce desirable effects such as increased fluorescence quantum yield, decreased lifetime and better fluorophore photostability. During the past decade a number of existing and novel nanoparticles and structures have appeared in the literature designed to improve both the fluorescence intensity and photo stability of fluorophores through MEF. Metal nanostructures have long been researched due to their ability to manipulate incident light. Localised surface plasmons (LSP) are charge density oscillations confined to metallic nanostructures and nanoparticles. If a particle is considered then an external field is able to displace the free electrons in the metal nanoparticle with respect to the fixed ionic core. This displacement sets up a restoring force leading to coherent oscillations of the charge density. This is termed the Localised Surface Plasmon Resonance (LSPR). LSPR is responsible for the electromagnetic-field enhancement that is thought to lead to surface enhanced Raman scattering (SERS). When it was observed that fluorescent molecules showed enhanced emissions in the presence of this plasmonic effect the field of MEF was born. A representation of the different optical responses that occur when light is absorbed and scattered by a metal nanoparticle can be seen. Due to above mechanism, the plasmonic effect and related enhancement are near the surface between 10 nm to 200 nm.

B-4. Method of Wash-Free Homogenous QMAX

Figure 16:
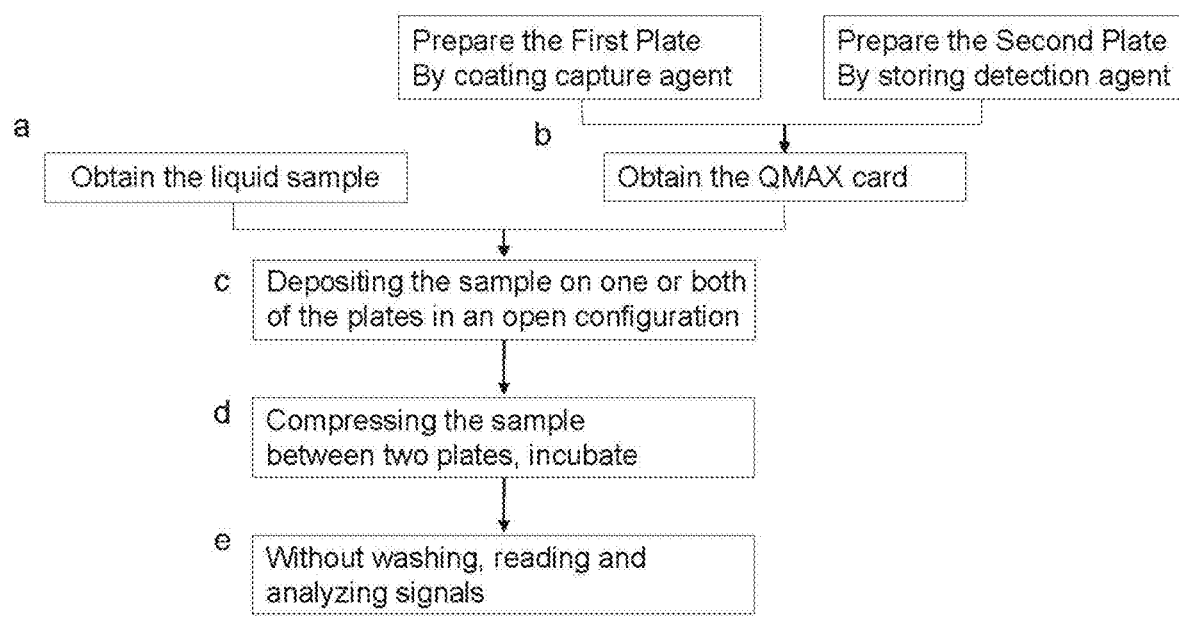
FIG. 16 is a flow chart showing the basic steps in an exemplary process for conducting an immunoassay using the wash-free homogenous QMAX device.

As shown in FIG. 16, in some embodiments, the process to prepare a QMAX device for an immunoassay includes:

(a) obtaining the liquid sample;
(b) obtaining a first plate, a second plate, and spacers fixed on one or both of the plates; wherein:
   i. the plates are movable relative to each other into different configurations;
   ii. one or both plates are flexible;
   iii. each of the plates has, on its respective inner surface, a sample contact area for contacting a sample that contains a target analyte;
   iv. the first plate sample contact area comprises: (a) a signal amplification layer that amplifies a signal from the target analyte or a label of the target analyte when the target analyte or label is 500 nm from the amplification layer; and (b) capture agents that are attached to the signal amplification layer and capable of binding and immobilizing the target analyte;
   v. the second plate comprises the spacers that are fixed with its inner surface;
   vi. the spacers have a predetermined substantially uniform height and a predetermined inter-spacer-distance; and
   vii. at least one of the spacers is inside the sample contact area;
(c) depositing the sample on one or both of the plates when the plates are in an open configuration, wherein in the open configuration the two plates are partially or entirely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises: bringing the two plates together; and conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and
(e) without washing, reading and analyzing signals emanating from at least part of the layer of uniform thickness, thereby determining the presence and/or quantity of the target analyte; wherein a conformable pressing is a method that makes the pressure applied over an area is substantially constant regardless the shape variation of the outer surfaces of the plates; and wherein the parallel pressing applies the pressures on the intended area at the same time, and a sequential pressing applies the pressure on a part of the intended area and gradually move to other area.

Here, the washing step means any processes to remove 30%, 40%, 50%, 60%, 70%, 80%, 90%, 100% or a range between any two of the values of the unbounded target analyte on the first plate after binding step. Typically, the washing step contains washing the plate with 1 times, 2 times, 3 times PBST, washing the plate with 1 times, 2 times, 3 times TBST, and washing the plate with 1 times, 2 times, 3 times water.

The method of any prior method paragraph, wherein the second plate sample contact area comprises a storage site containing detection agents that upon contacting the sample, dissolves into the sample and diffuses in the sample, wherein each capture agent, target analyte and corresponding detection agent is capable of forming a capture agent-target analyte-detection agent sandwich in a binding site of the first plate.

The method of any prior method paragraph, wherein the second plate sample contact area comprises a storage site containing detection agents that upon contacting the sample, dissolves into the sample and diffuses in the sample, wherein the detection agent binds to the capture agent and competitively inhibits the binding between the capture agent and the target analyte.

The method of any prior method paragraph, wherein during the step (b), the conformable pressing is by human hand.

The method of any prior method paragraph, wherein the conformable pressing of step (d) is provided by a pressured liquid, a pressed gas, or a conformal material.

The method of any prior method paragraph, before step (e) and after step (d), further comprising incubating the layer of uniform thickness for a predetermined period of time.

The method of paragraph B8, wherein the predetermined period of time is equal to or longer than the time needed for the detection agent to diffuse into the sample across the layer of uniform thickness.

The method of any prior paragraphs, wherein the sample is deposited on the first plate.

The method of any prior paragraphs, before step (d) after step (c), further comprising incubating the sample on the first plate for a predetermined period of time.

The method of paragraph B11, wherein the predetermined period of time is equal to or longer than the time needed for the binding between the capture agent and the target analyte to reach an equilibrium.

B-5. Theoretical Analyze of Sensitivity of Wash-Free Homogeneous QMAX Assay

Define final capture density (directly related to LoD or sensitivity of the assay) of the target analyte (with label) on the substrate (first plate) is $d_c$;

Define the label density in the liquid is $D_L$;

Define amplification factor is A;

Define amplification factor is uniform within $L_A$ of the substrate;

Define liquid height is by X-Plate is $L_X$ ($L_X \gg L_A$);

Define the label signal intensity's standard deviation (sd) of the liquid is $\sigma$;

Since signal from capture fluorophore must be larger than (1+3×sd)×background signal from liquid, thus:

$$Ad_c \geq (1+3\sigma)(D_L L_X + AD_L L_A)$$

The smallest capture density (proportional to LoD) detectable with this method is:

$$d_c = \frac{(1+3\sigma)(L_X + AL_A)D_L}{A}$$

Clearly, increase amplification factor (A) of substrate, decrease QMAX thickness ($L_X$) can improve the performance (sensitivity) of wash-free homogeneous assay in QMAX card format. But decrease the QMAX thickness might decrease the binding amount. Thus there is a trade-off for the parameter of QMAX gap size or liquid thickness.

B-6. Examples of a Process of Wash-Free Homogenous Assay to Detect Human-IgG FIG. 17, a shows the schematic of preparing M-Plate as the binding site plate (first plate). M-Plate is fabricated on 500 um thick glass is a periodic nonmetallic pillar array with a period 200 nm, pillar height 55 nm and pillar diameter 80 nm, a gold disk on top of each pillar with a thickness 50 nm and diameter 100 nm, a gold backplane on the foot of the pillars, gold nanodots with 10 nm diameter randomly located on the pillar walls, and nanogaps between these metal components.

M-Plate with a size of 1 inch by 1 inch was first incubated in DSU 1 mM in Dioxin overnight, then washed with dioxin. After coating the self-assemble layer (DSU), M-Plate was put in a container with 10 ug/mL protein-A in PBS for 2 hours, followed by washing 3 times with PBST. M-Plate was then coated with Capture Ab (goat anti-human IgG) 10 ug/mL in PBS for 2 hours, followed by washing 3 times with PBST. At last, M-Plate was blocked with 2% BSA in PBS for 2 hours, followed by washing 3 times with PBST, and 3 times with water and dry at 37° C. in air for 1 hour.

FIG. 17, b shows the schematic of preparing X-Plate as the storage plate (second plate). X-Plate is a micro-pillar array with 30×40 um pillar size, 80 um inter spacing distance and 30 um pillar height, made on 175 um thick PMMA film.

Detection Ab (mouse anti-human IgG) conjugated IR-800 10 ug/mL 200 uL uniformly dried on X-Plate (25 mm×25 mm area) at 37° C. for 2 hours.

In some embodiments, the surface of the first plate facing the second plate is defined as the inner surface of the first plate; the surface of the second plate that faces the first plate are also defined as the inner surface of the second plate. In some embodiments, the inner surfaces of the respective plates comprise a sample contact area for contacting a sample that comprises an analyte. The sample contact area can occupy part or the entirety of the respective inner surface. As shown in FIG. 13, the second plate can comprises spacers that are fixed on the inner surface of the second plate. It should be noted, however, that in some embodiments the spacers are fixed on the inner surface of the first plate and in other embodiments on the inner surfaces of both the second plate and the first plate.

In some embodiments the first plate comprises a capture antibody that is coated on the inner surface of the first plate. In some embodiments, the capture antibody 150 can be applied to the surface by printing, spraying, soaking or any other method that applies homogenous layer of reagents. In certain embodiments, the capture antibody 150 is dried on the first plate 10. It should also be noted that in some embodiments the capture antibody 150 is coated on the inner surface of the first plate 10, not the second plate 20; in some embodiments the capture antibody 150 is coated on the inner surface of the second plate 20, not the first plate 10; in some embodiments the capture antibody 150 is coated on the inner surfaces of both plates 10 and 20. In some embodiments, the capture antibody is either monocolonal, polycolonal antibody, engineered antibody (e.g. single chain variable fragments (scFv)) or fragments thereof. In some embodiments, the concentration of coated capture antibody ranges from 1 fg/mL to 1 g/mL.

In some embodiments, the capture antibody 150 is configured to bind to the analyte 95. For example, when the analyte 95 comprises an antigen epitope, in certain embodiments the capture antibody 150 is configured to specifically bind to the antigen epitope. In some embodiments, the capture antibody 150 is (a) covalently bound to the inner surface, or (b) attached to the surface by passive absorption through hydrophobic interactions between solid surface and non-polar residues on the proteins. For example, in some embodiments as shown in FIG. 13, the capture antibody 150 is attached to the first plate 10 through protein A 158. In certain embodiments, the capture antibody 150 can immobilize the analyte 95 onto the inner surface of the first plate 10.

While antibodies can be used to detect antigens, antigens can also be used to detect antibodies. For example, in some embodiments the present invention, a capture antigen (or epitope), instead of the capture antibody, can be coated on the inner surface of a respective plate (e.g. the first plate 10). The capture antigen can be attached to the inner surface and used to immobilize an analyte (e.g. antibody or antibody-expressing cell) onto the inner surface.

In some embodiments the first plate 10 comprises blockers 152 that are coated on the inner surface of the first plate 10. In some embodiments, the blockers 152 block any unoccupied sites on the solid surface that can cause unwanted nonspecific bindings in assays. In certain embodiments, the blocker 152 reduces nonspecific binding. In certain embodiments, the blockers 152 can be applied to the surface by printing, spraying, soaking or any other method that applies homogenous layer of reagents. In certain embodiments, the blockers 152 are dried on the first plate 10. It should also be noted that in some embodiments the blockers 152 are coated on the inner surface of the first plate 10, not the second plate 20; in some embodiments the blockers 152 are coated on the inner surface of the second plate 20, not the first plate 10; in some embodiments the blockers 152 are coated on the inner surfaces of both plates 10 and 20. In some embodiments, the blockers 152 are bovine serum albumin (BSA), casein or total proteins from whole milk, etc.

In some embodiments the first plate 10 comprises a stabilizer 155 that is coated on the inner surface of the first plate 10. In some embodiments, the stabilizer 155 helps maintain the proper folding of protein when dried so that the function of the protein is not disrupted during storage. In certain embodiments, the stabilizer 155 prolongs the usage life span of the reagents, such as but not limited to a protein. In certain embodiments, the stabilizer 155 can be applied to the surface by printing, spraying, soaking or any other method that applies homogenous layer of reagents. In certain embodiments, the stabilizer 155 is dried on the first plate 10. It should also be noted that in some embodiments the stabilizer 155 is coated on the inner surface of the first plate 10, not the second plate 20; in some embodiments the stabilizer 155 is coated on the inner surface of the second plate 20, not the first plate 10; in some embodiments the stabilizer 155 is coated on the inner surfaces of both plates 10 and 20. In some embodiments, the stabilizer 155 is sugar such as but not limited to sucrose and glucose. In some embodiments, the stabilizer 155 is a polymer. In certain embodiments, the stabilizer 155 is glycerol.

In some embodiments the second plate 20 comprises a detection antibody 160 that is coated on the inner surface of the second plate 20. In some embodiments, the detection antibody 160 can be applied to the surface by printing, spraying, soaking or any other method that applies homogenous layer of reagents. In certain embodiments, the detection antibody 160 is dried on the second plate 20. It should also be noted that in some embodiments the detection antibody 160 is coated on the inner surface of the second plate 20, not the first plate 10; in some embodiments the detection antibody 160 is coated on the inner surface of the first plate 10, not the second plate 20; in some embodiments the detection antibody 160 is coated on the inner surfaces of both plates 10 and 20. In some embodiments, the detection antibody 160 is either monoclonal, polyclonal antibody, engineered antibody (e.g. single chain variable fragments (scFv)) or fragments thereof. In some embodiments, the concentration of coated detection antibody ranges from 1 fg/mL to 1 g/mL.

In some embodiments, the detection antibody 160 is configured to bind to the analyte 95. For example, when the analyte 95 comprises an antigen epitope, in certain embodiments the detection antibody 160 is configured to specifically bind to the antigen epitope. In certain embodiments, the capture antibody 150 and the detection antibody 160 bind to different sites (e.g. epitopes) of the analyte 95. In certain embodiments, the detection antibody is configured to specifically bind to a capture antibody-analyte complex. In certain embodiments, the detection antibody 160 is not covalently bound to the inner surface. In certain embodiments, the detection antibody 160 is not attached to the surface by passive absorption through hydrophobic interactions between solid surface and non-polar residues on the proteins. In certain embodiments, the detection antibody 160 can diffuse into the sample after the sample is deposited and the detection antibody 160 is in contact with the sample liquid.

In some embodiments, the detection antibody 160 is configured to produce a detectable signal after binding to the analyte 95. For example, in some embodiments the signal can be a colorimetric signal, a luminescent signal, or a fluorescent signal. In some embodiments for example, the detection antibody 160 is labeled by a fluorescent label 165, which produces a signal after the detection antibody 160 binds to the analyte or to the capture antibody-analyte complex. In some embodiments, the fluorescent label 165 directly labels the detection antibody 160. In some embodiments, the fluorescent label 165 labels a reagent that can bind to the detection antibody 160 or a detection antibody-analyte complex. In some embodiments, the secondary antibody can be conjugated with an optical detectable label, e.g., a fluorophore such as but not limited to cy5, IR800, SAPE IRDye800CW, Alexa 790, Dylight 800.

While antibodies can be used to detect antigens, antigens can also be used to detect antibodies. For example, in some embodiments of the present invention, a detection antigen (or epitope), instead of the detection antibody, can be coated on the inner surface of a respective plate (e.g. the second plate 20). The capture antigen can be attached to the inner surface and used to detect an analyte (e.g. antibody or antibody-expressing cell) onto the inner surface.

In some embodiments the second plate 20 comprises stabilizers 155, which stabilizes the proteins (e.g. the detection antibody 160) and prolongs the shelf-life of the device. In some embodiments, the stabilizer 155 helps maintain the proper folding of protein when dried so that the function of the protein is not disrupted during storage. In certain embodiments, the stabilizer 155 prolongs the usage life span of the reagents, such as but not limited to a protein. In certain embodiments, the stabilizer 155 can be applied to the surface by printing, spraying, soaking or any other method that applies homogenous layer of reagents. In certain embodiments, the stabilizer 155 is dried on the first plate 10. It should also be noted that in some embodiments the stabilizer 155 is coated on the inner surface of the first plate 10, not the second plate 20; in some embodiments the stabilizer 155 is coated on the inner surface of the second plate 20, not the first plate 10; in some embodiments the stabilizer 155 is coated on the inner surfaces of both plates 10 and 20. In some embodiments, the stabilizer 155 is sugar such as but not limited to sucrose and glucose. In some embodiments, the stabilizer 155 is a polymer. In certain embodiments, the stabilizer 155 is glycerol. In some embodiments, the stabilizer coated on the first plate 10 and the stabilizer coated on the second plate 20 are the same. In some embodiments, the stabilizer coated on the first plate 10 and the stabilizer coated on the second plate 20 are different.

In some embodiments, the above chemicals including capture antibody, blocker, stabilizer, detection antibody are printed in a periodic/aperiodic array with droplet size 10 µL, 50 µL, 100 µL, 500 µL, 1 nL, 5 nL, 10 nL, 100 nL, 1 uL, 10 uL, or a range between any two of the values; and a preferred range of 10 µL to 100 µL, 100 µL to 500 µL, 500 µL to 1 nL, 1 nL to 10 nL, 10 nL to 100 nL, 100 nL to 500 nL.

In some embodiments, the above chemicals including capture antibody, blocker, stabilizer, detection antibody are printed in a periodic/aperiodic array with droplet with average periodicity of 10 um, 100 um, 500 um, 1 mm, 5 mm, 10 mm or a range between any two of the values.

Figure 18:
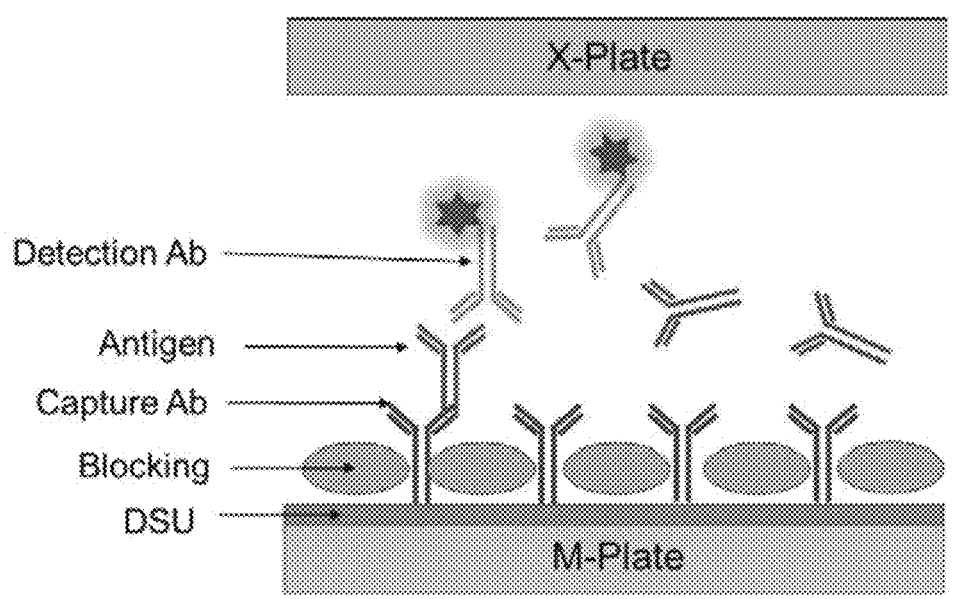
FIG. 18 shows a schematic drawing for an exemplary embodiment of a QMAX device in a closed configuration.

FIG. 18 shows the schematic of testing antigen of human-IgG with wash-free homogenous QMAX device in close configuration. In the experiment, 1 uL antigen (human IgG in PBS) with concentrations of 1 ug/mL, 100 ng/mL, 10 ng/mL, 1 ng/mL, 100 pg/mL, 10 pg/mL were dropped on binding site plate (2.5 mm×2.5 mm) at different locations. Then press the center of storage site plate (2.5 mm×2.5 mm) on top of the liquid by hand. Incubate for 1 min. Without wash, direct measure the fluorescence signal at different spot.

In some embodiments, the reagents are labeled for detection and/or measurement of the analyte. With a labeled reagent, the analyte can be labeled by chemical reagents and/or specific finding. Labeling the analyte includes using, for example, a labeling agent, such as an analyte specific binding member that includes a detectable label. Detectable labels include, but are not limited to, fluorescent labels, colorimetric labels, chemiluminescent labels, enzyme-linked reagents, multicolor reagents, avidin-streptavidin associated detection reagents, and the like. In certain embodiments, the detectable label is a fluorescent label. Fluorescent labels are labeling moieties that are detectable by a fluorescence detector. For example, binding of a fluorescent label to an analyte of interest allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

In certain embodiments, suitable fluorescent molecules (fluorophores) for labeling include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAM RA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In certain embodiments, the labeling agent is configured to bind specifically to the analyte of interest. In certain embodiments, a labeling agent is present in the QMAX device before the sample is applied to the QMAX device. In other embodiments, the labeling agent is applied to the QMAX device after the sample is applied to the QMAX device. In certain embodiments, after the sample is applied to the QMAX device, the QMAX device is washed to remove any unbound components, e.g. un bound analyte and other non-analyte coponents in the sample, and the labeling agent is applied to the QMAX device after the washing to label the bound analyte. In some embodiments, the QMAX device is washed after the labeling agent is bound to the analyte-capture agent complex to remove from the QMAX device any excess labeling agent that is not bound to an analyte-capture agent complex.

In certain embodiments, the analyte is labeled after the analyte is bound to the QMAX device, e.g., using a labeled binding agent that can bind to the analyte simultaneously as the capture agent to which the analyte is bound in the QMAX device, i.e., in a sandwich-type assay. In some embodiments, a nucleic acid analyte is captured on the QMAX device, and a labeled nucleic acid that can hybridize to the analyte simultaneously as the capture agent to which the nucleic acid analyte is bound in the QMAX device.

In certain aspects, a QMAX device enhances the light signal, e.g., fluorescence or luminescence, that is produced by the detectable label bound directly or indirectly to an analyte, which is in turn bound to the QMAX device. In certain embodiments, the signal is enhanced by a physical process of signal amplification. In some embodiments, the light signal is enhanced by a nanoplasmonic effect (e.g., surface-enhanced Raman scattering). Examples of signal enhancement by nanoplasmonic effects is described, e.g., in Li et al, Optics Express 2011 19: 3925-3936 and WO2012/024006, which are incorporated herein by reference. In certain embodiments, signal enhancement is achieved without the use of biological/chemical amplification of the signal. Biological/chemical amplification of the signal includes enzymatic amplification of the signal (e.g., used in enzyme-linked immunosorbent assays (ELISAs)) and polymerase chain reaction (PCR) amplification of the signal. In other embodiments, the signal enhancement is achieved by a physical process and biological/chemical amplification.

In certain embodiments, the QMAX device is configured to enhance the signal from a detectable label that is proximal to the surface of the QMAX device by 103 fold or more, for example, 104 fold or more, 105 fold or more, 106 fold or more, 107 fold or more, including 108 fold or more, where the signal is enhanced by a range of 103 to 109 fold, for example, 104 to 108 fold, or 105 to 107 fold, compared to a detectable label that is not proximal to the surface of the QMAX device, i.e., compared to a detectable label bound to an analyte on a conventional ELISA plate, on a conventional nucleic acid microarray, suspended in solution, etc. In certain embodiments, the QMAX device is configured to enhance the signal from a detectable label that is proximal to the surface of the QMAX device by 103 fold or more, for example, 104 fold or more, 105 fold or more, 106 fold or more, 107 fold or more, including 108 fold or more, where the signal is enhanced by a range of 103 to 109 fold, for example, 104 to 108 fold, or 105 to 107 fold, compared to an analyte detecting array that is not configured to enhance the signal using a physical amplification process, as described above.

In certain embodiments, the QMAX device is configured to have a detection sensitivity of 0.1 nM or less, such as 10 pM or less, or 1 pM or less, or 100 fM or less, such as 10 fM or less, including 1 fM or less, or 0.5 fM or less, or 100 aM or less, or 50 aM or less, or 20 aM or less. In certain embodiments, the QMAX device is configured to have a detection sensitivity in the range of 10 aM to 0.1 nM, such as 20 aM to 10 pM, 50 aM to 1 pM, including 100 aM to 100 fM. In some instances, the QMAX device is configured to be able to detect analytes at a concentration of 1 ng/mL or less, such as 100 pg/mL or less, including 10 pg/mL or less, 1 pg/mL or less, 100 fg/mL or less, 10 fg/mL or less, or 5 fg/mL or less. In some instances, the QMAX device is configured to be able to detect analytes at a concentration in the range of 1 fg/mL to 1 ng/mL, such as 5 fg/mL to 100 pg/mL, including 10 fg/mL to 10 pg/mL. In certain embodiments, the QMAX device is configured to have a dynamic range of 5 orders of magnitude or more, such as 6 orders of magnitude or more, including 7 orders of magnitude or more.

In certain instances, the period of time from applying the sample to the QMAX device to reading the QMAX device ranges from 1 second to 30 minutes, such as 10 seconds to 20 minutes, 30 seconds to 10 minutes, including 1 minute to 5 minutes. In some instances, the period of time from applying the sample to the signal enhancing detector to generating an output that can be received by the device is 1 hour or less, 30 minutes or less, 15 minutes or less, 10 minutes or less, 5 minutes or less, 3 minutes or less, 1 minute or less, 50 seconds or less, 40 seconds or less, 30 seconds or less, 20 seconds or less, 10 seconds or less, 5 seconds or less, 2 seconds or less, 1 second or less, or even shorter. In some instances, the period of time from applying the sample to the signal enhancing detector to generating an output that can be received by the device is 100 milliseconds or more, including 200 milliseconds or more, such as 500 milliseconds or more, 1 second or more, 10 seconds or more, 30 seconds or more, 1 minute or more, 5 minutes or more, or longer.

Any suitable method is used to read the QMAX device to obtain a measurement of the amount of analyte in the sample. In some embodiments, reading the QMAX device includes obtaining an electromagnetic signal from the detectable label bound to the analyte in the QMAX device. In certain embodiments the electromagnetic signal is a light signal. The light signal obtained include the intensity of light, the wavelength of light, the location of the source of light, and the like. In particular embodiments, the light signal produced by the label has a wavelength that is in the range of 300 nm to 900 nm. In certain embodiments, the light signal is read in the form of a visual image of the QMAX device.

In certain embodiments, reading the QMAX device includes providing a source of electromagnetic radiation, e.g., light source, as an excitation source for the detectable label bound to the biomarker in the QMAX device. The light source is any suitable light source to excite the detectable label. Exemplary light sources include, but are not limited to, sun light, ambient light, UV lamps, fluorescent lamps, light-emitting diodes (LEDs), photodiodes, incandescent lamps, halogen lamps, and the like.

Reading the QMAX device is achieved by any suitable method to measure the amount of analyte that is present in the sample and bound to the QMAX device. In certain embodiments, the QMAX device is read with a device configured to acquire the light signal from the detectable label bound to the analyte in the QMAX device. In some cases, the device is a handheld device, such as a mobile phone or a smart phone. Any suitable handheld device configured to read the QMAX device is used in the devices, systems and methods in the present invention. Devices configured to read the QMAX device are described in, e.g., U.S. Provisional Application Ser. No. 62/066,777, filed on Oct. 21, 2014, which is incorporated herein by reference.

In some embodiments, the device includes an optical recording apparatus that is configured to acquire a light signal from the QMAX device, e.g., acquire an image of the QMAX device. In certain instances, the optical recording apparatus is a camera, such as a digital camera. The term "digital camera" denotes any camera that includes as its main component an image-taking apparatus provided with an image-taking lens system for forming an optical image, an image sensor for converting the optical image into an electrical signal, and other components, examples of such cameras including digital still cameras, digital movie cameras, and Web cameras (i.e., cameras that are connected, either publicly or privately, to an apparatus connected to a network to permit exchange of images, including both those connected directly to a network and those connected to a network by way of an apparatus, such as a personal computer, having an information processing capability). In one example, reading the QMAX device includes video imaging that captures changes over time. For example, a video is acquired to provide evaluation on dynamic changes in the sample applied to the QMAX device.

In certain embodiments, the optical recording apparatus has a sensitivity that is lower than the sensitivity of a high-sensitivity optical recording apparatus used in research/clinical laboratory settings. In certain cases, the optical recording apparatus used in the subject method has a sensitivity that is lower by 10 times or more, such as 100 times or more, including 200 times or more, 500 times or more, or 1,000 times or more than the sensitivity of a high-sensitivity optical recording apparatus used in research/clinical laboratory settings.

In certain embodiments, the device has a video display. Video displays include components upon which a display page is displayed in a manner perceptible to a user, such as, for example, a computer monitor, cathode ray tube, liquid crystal display, light emitting diode display, touchpad or touchscreen display, and/or other means known in the art for emitting a visually perceptible output. In certain embodiments, the device is equipped with a touch screen for displaying information, such as the image acquired from the detector and/or a report generated from the processed data, and allowing information to be entered by the subject.

In any embodiment described herein, the system is designed for performing a multiplex assay and, as such, contain multiple storage sites, multiple binding/assaying sites, or multiple storage sites and multiple binding/assaying sites such that different assays can be performed on different areas on the surface of one of the plates. For example, in one embodiment, in one embodiment, one of the plates contains multiple binding/assaying sites that each contains a different capture agent, thereby allowing the detection of multiple analytes in the sample in the same assay. The sites are spatially separated from, although proximal to, one another.

In certain embodiments, the first plate further comprises, on its surface, a first predetermined assay site and a second predetermined assay site, wherein the distance between the edges of the neighboring multiple assay sites is substantially larger than the thickness of the uniform thickness layer when the plates are in the closed position, wherein at least a part of the uniform thickness layer of the sample is over the predetermined assay sites, and wherein the sample has one or a plurality of analytes that are capable of diffusing in the sample. By making the distance between the edges of the neighboring multiple assay sites large than the sample thickness, it makes it possible to have multiple binding/assaying sites without fluidically isolated the different portion of a sample, since an saturation incubation of the assay can complete between a significant inter-diffusion between the two neighboring sites. By properly choosing the ratio of the neighboring distance to the sample thickness and properly selecting the measurement time between a time longer than the assay saturation incubation time but less than a time for a significant inter-diffusion between two neighboring sites, one can do multiplexing by QMAX without isolating different part of a sample. In some embodiments, the ratio of the neighbor distance to the sample thickness at the closed configuration is 1.5 or larger, 3 or larger, 5 or larger, 10 or larger, 20 or larger, 30 or larger, 50 or larger, 100 or larger, 200 or larger, 1000 or larger, 10,000 or larger, or a range between any two of the values. The ratio is 3 or larger for a preferred embodiment, 5 or larger for another preferred embodiment, 10 or larger for a certain preferred embodiment, 30 or larger for another preferred embodiment, and 100 or larger for another preferred embodiment.

In certain embodiments, the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In certain embodiments, the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the QMAX device can for parallel, multiplex, assaying of a liquid sample without fluidic isolation (i.e., without their being a physical barrier between the assay regions). In some embodiments, this device comprises a first plate and a second plate, wherein: i. the plates are movable relative to each other into different configurations; one or both plates are flexible; ii. one or both of the plates comprise spacers that are fixed with a respective plate; and the spacers have a predetermined substantially uniform height and a predetermined constant inter-spacer distance; iii. each of the plates has, on its respective surface, a sample contact area for contacting a sample that contains a sample that contains one or more target analytes which is capable of diffusing in the sample, iii. the first plate has, on its surface, one or a plurality of binding/assaying sites that each has a predetermined area comprising a capture agent that binds and immobilizes a corresponding target analyte of the sample; and iv the second plate has, on its surface, one or a plurality of corresponding storage sites that each has a predetermined area and comprises a detection agent of a concentration that, upon contacting the sample, dissolves into the sample and diffuses in the sample, wherein each capture agent, target analyte and corresponding detection agent is capable of forming a capture agent-target analyte-detection agent sandwich in a binding/assaying site of the first plate; wherein one of the configurations is an open configuration, in which: the two plates are either partially or completely separated apart, the spacing between the plates is not regulated by the spacers, and the sample is deposited on one or both of the plates, and wherein another of the configurations is a closed configuration which is configured after the sample deposition in the open configuration; and in the closed configuration: i. at least part of the sample is compressed into a layer of uniform thickness that is in contact with and confined by the inner surfaces of the two plates and that covers the one or a plurality of binding/ assaying sites and the one or a plurality of storage sites, ii the one or a plurality of corresponding storage sites are over the one or a plurality of binding/assaying sites, and iii. the uniform thickness of the layer is regulated by the spacers and the plates, is less than 250 um, and is substantially less than the linear dimension of the predetermined area of each storage site; and iv. there is no fluidic isolation between the binding/assaying site and/or the storage sites, wherein the separation between the edges of the neighboring storage sites and the separation between the edges of the neighboring binding/assaying sites are larger than the distance that a target analyte or detection agent can diffuse in the relevant time, and wherein there is no fluidic isolation between the binding/assaying site sites and/or the storage sites.

In some embodiments, the first plate has, on its surface, a plurality of (at least 2, at least 4 or at least 16 or more) of the binding/assaying sites.

In some embodiments, each of said plurality of binding/assaying sites binds to a different target analyte.

In some embodiments, the second plate has, on its surface, a plurality (at least 2, at least 4 or at least 16 or more) of the corresponding storage sites.

In some embodiments, each of the plurality of corresponding storage sites binds to a different target analyte.

In some embodiments, the first plate has, on its surface, a plurality of said binding/assaying sites and the second plate has, on its surface, a plurality of said corresponding storage sites, wherein each binding/assaying site faces a corresponding storage site when the plates are in the closed configuration.

In some embodiments, the first plate has, on its surface, a plurality of said binding/assaying sites and the second plate has, on its surface, a storage site, wherein at least some of the binding/assaying sites face an area in the storage site when the plates are in the closed configuration.

In some embodiments the first plate has, on its surface, a binding/assaying site and the second plate has, on its surface, a plurality of storage sites, wherein at least some of the storage sites face an area in the binding/assaying site when the plates are in the closed configuration.

In some embodiments the first plate has, on its surface, a plurality of binding/assaying sites, wherein the binding/assaying sites contain different capture agents that bind and immobilize the same target analyte.

In some embodiments the first plate has, on its surface, a plurality of binding/assaying sites, wherein the binding/assaying sites contain the same capture agent.

In some embodiments, the capture agent is at different densities in the different binding/assaying sites. These embodiments are used to provide a way to quantify the amount of analyte in a sample.

In some embodiments, there is a separation between two neighboring binding/assaying sites or two neighboring storage sites, and the ratio of the separation to the sample thickness in the closed configuration is at least 3, e.g., at least 5, at least 10, at least 20 or at least 50.

In some embodiments, the inter-spacer distance is in the range of 1 um to 120 um.

In some embodiments, the flexible plates have a thickness in the range of 20 um to 250 um (e.g., in the range of 50 um to 150 um) and Young's modulus in the range 0.1 to 5 GPa (e.g., in the range of 0.5-2 GPa).

In some embodiments, the thickness of the flexible plate times the Young's modulus of the flexible plate is in the range 60 to 750 GPa-um.

In some embodiments, this method comprises: (a) obtaining a sample that contains one or more target analytes, which are capable of diffusing in the sample; (b) obtaining a first and second plates that are movable relative to each other into different configurations, wherein: i. one or both of the plates comprise spacers that are fixed with a respective plate and one or both plates are flexible, ii. the spacers have a predetermined substantially uniform height and a predetermined constant inter-spacer distance, iii. the first plate has, on its surface, one or a plurality of binding/assaying sites that each has a predetermined area comprising a capture agent that binds and immobilizes a corresponding target analyte of (a); and iv. the second plate has, on its surface, one or a plurality of corresponding storage sites that each has a predetermined area and comprises a detection agent of a concentration that, upon contacting the sample, dissolves into the sample and diffuses in the sample, wherein each capture agent, target analyte and corresponding detection agent is capable of forming a capture agent-target analyte-detection agent sandwich in a binding/assaying site of the first plate; (c) depositing the sample on one or both of the plates when the plates are configured in an open configuration, wherein the open configuration is a configuration in which the two plates are either partially or completely separated apart and the spacing between the plates is not regulated by the spacers; (d) after (c), compressing the sample by bringing the two plates into a closed configuration, wherein the closed configuration is a configuration in which: i. at least part of the sample is compressed into a layer of uniform thickness that is in contact with and confined by the inner surfaces of the two plates and that is in contact with the one or a plurality of binding/assaying sites and the one or a plurality of storage sites, ii the one or a plurality of corresponding storage sites are over the one or a plurality of binding/assaying sites, and iii. the uniform thickness of the layer is regulated by the spacers and the plates, is less than 250 um, and is substantially less than the linear dimension of the predetermined area of each storage site; (e) after (d) and while the plates are in the closed configuration, either: (1) incubating the sample for a relevant time length and then stopping the incubation; or (2) incubating the sample for a time that is equal or longer than the minimum of a relevant time length and then assessing, within a time period that is equal or less than the maximum of the relevant length of time, the binding of each target analyte to a binding/assaying site; wherein the relevant time length is: i. equal to or longer than the time that it takes for a target analyte of (a) to diffuse across the thickness of the uniform thickness layer at the closed configuration; and ii. significantly shorter than the time that it takes a target analyte of (a) to laterally diffuse across the smallest linear dimension of the predetermined area of a storage site or binding/assaying site; thereby producing a reaction in which, at the end of the incubation in (1) or during the assessing in (2), the majority of the capture agent-target analyte-detection agent sandwich bound to each binding/assaying site is from a corresponding relevant volume of the sample; wherein the incubation allows each target analyte to bind to a binding/assaying site and a detection agent, wherein the corresponding relevant volume is a portion of the sample that is above the corresponding storage site at the closed configuration, wherein the separation between the edges of the neighboring storage sites and the separation between the edges of the neighboring binding/assaying sites are larger than the distance that a target analyte or detection agent can diffuse in the relevant time, and wherein there is no fluidic isolation between the binding/assaying site sites and/or the storage sites.

B-7. Examples and Comparison for Wash-Free Homogenous Immunoassay QMAX Results

Figure 19:
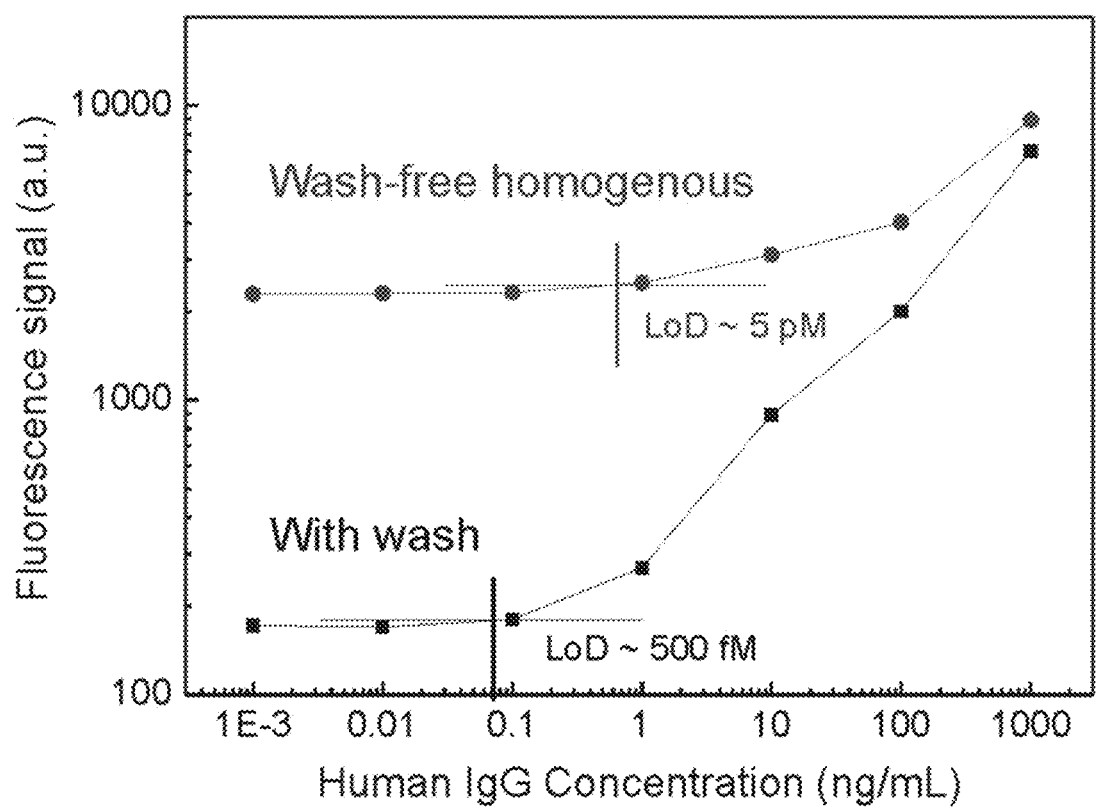
FIG. 19 shows an example of a standard curve of a homogenous QMAX human IgG sandwich immunoassay, compared with normal QMAX human IgG sandwich immunoassay.

FIG. 19 (a) shows a standard curve of wash-free homogenous QMAX card with limit of detection (LoD) of human-IgG assay 5 pM; (b) while QMAX card with wash 3 times with PBST shows LoD 500 fM. Wash-free homogenous QMAX card has higher overall signal due to the liquid background, for example, at concentration of 1 pg/mL, 10 pg/mL, 100 pg/mL the background signal of wash-free QMAX is around 10 times higher than with-wash QMAX.

In the detection, laser light source with 785 nm wavelength 1 mW power, spectrometer and photodetector were used.

To compare the performances of wash-free homogenous Immunoassay QMAX with traditional microplate immunoassay, we performed the microplate immunoassay in parallel with the same chemicals used in QMAX. We used the Corning 96 well microplate, first incubated Capture Ab (goat anti-human IgG) 10 ug/mL in PBS, 100 uL each well, coated for 2 h/Wash 3× with PBST, followed by Blocking with 2% BSA in PBS, 150 uL each well, for 2 h/Wash 3× with PBST, then captured antigen (human IgG in PBS) with concentrations of 1 ug/mL to 1 pg/mL, 100 uL each well, for 2 h/Wash 3× with PBST; at last incubated detection Ab (mouse anti-human IgG) conjugated IR-800 10 ug/mL in PBS, 100 uL each well, coated for 2 h/Wash 3× with PBST. We measured the microplate in parallel with the homogenous immunoassay QMAX.

Figure 20:
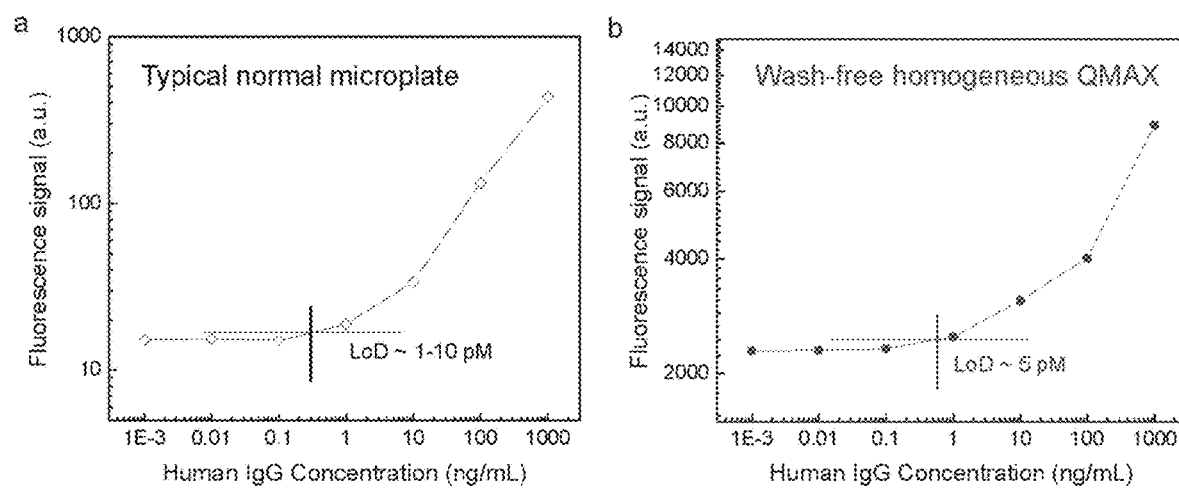
FIG. 20 shows an example of a standard curve of a homogenous QMAX human IgG sandwich immunoassay, compared with normal microplate human IgG sandwich immunoassay.
Figure 21:
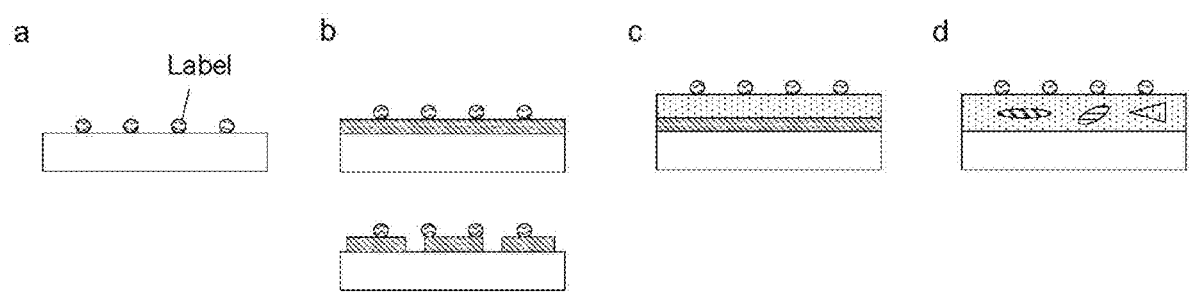
FIG. 21 shows schematics of amplification surfaces with (a) plate have one layer of material; (b) plate have two layers of material (one of the layers is continuous or non-continuous); (c) plate have three or over three layers of material; (d) plate have layers which are the combination of materials. Labels are on top surface of the device.

FIG. 20 shows the standard curves of both homogenous QMAX and traditional microplate IgG immunoassay. Compared with normal microplate human IgG immunoassay (100 uL sample volume, hours assay time, multi steps and multi washing) with LoD=1-10 pM, the Wash-free homogenous QMAX card (1 uL sample volume, 1 min assay time, one step assay and no wash) is more simple, fast, cheap and have similar or even better sensitivity.

As demonstrated by the examples, in some embodiments, the present invention provides a point-of-care (POC) platform for immunoassays that is a wash-free homogeneous assay method without requirements of any separation steps and washing steps, other than the performances to accelerate the process with 1 min incubation time and quantify the parameters (achieve the human-IgG sandwich assay with LoD 5 pM, which is similar to microplate IgG immunoassay, which require 100 uL sample volume, hours assay time, multi steps and multi washing), simplify the sample collection and measurement processes, handle samples with small volumes (1 uL), allow results to be analyzed automatically (e.g. by a mobile phone), and allow non-professionals to perform the assay her/himself.

Example of human IgG QMAX assay is provided here in which no-washing step is required in process, 1 μL of samples were used in the one minute assay. Limit of detection (LOD) of human IgG QMAX assay is 5 pM. IgG from human blood and saliva could be readily detected in one minute. This platform can be adapted for any immunoassays that are performed in traditional micro titter plate and thus have broad applications.

B-8. Examples of Present Invention

BA1. A device for homogenous assay, comprising:
a first plate, a second plate, and spacers, wherein:
i. the plates are movable relative to each other into different configurations;
ii. one or both plates are flexible;
iii. each of the plates has, on its respective inner surface, a sample contact area for contacting a sample that contains a target analyte;
iv. the first plate sample contact area comprises: (a) a signal amplification layer that amplifies a signal from the target analyte or a label of the target analyte when the target analyte or label is 500 nm from the amplification layer; and (b) capture agents that are attached to the signal amplification layer and capable of binding and immobilizing the target analyte;
v. the second plate comprises the spacers that are fixed with its inner surface;
vi. the spacers have a predetermined substantially uniform height and a predetermined inter-spacer-distance; and
vii. at least one of the spacers is inside the sample contact area;
wherein one of the configurations is an open configuration, in which: the two plates are separated apart, the spacing between the plates is not regulated by the spacers, and the sample is deposited on one or both of the plates; and
wherein another of the configurations is a closed configuration which is configured after the sample deposition in the open configuration; and in the closed configuration: at least part of the sample is compressed by the two plates into a layer of uniform thickness, wherein the uniform thickness of the layer is confined by the inner surfaces of the two plates and is regulated by the plates and the spacers.

BB1. A method of homogeneous assay with no wash step after assay incubation, comprising the steps of:
(c) obtaining the liquid sample;
(d) obtaining a first plate, a second plate, and spacers fixed on one or both of the plates; wherein:
viii. the plates are movable relative to each other into different configurations;
ix. one or both plates are flexible;
x. each of the plates has, on its respective inner surface, a sample contact area for contacting a sample that contains a target analyte;
xi. the first plate sample contact area comprises: (a) a signal amplification layer that amplifies a signal from the target analyte or a label of the target analyte when the target analyte or label is 500 nm from the amplification layer; and (b) capture agents that are attached to the signal amplification layer and capable of binding and immobilizing the target analyte;
xii. the second plate comprises the spacers that are fixed with its inner surface;
xiii. the spacers have a predetermined substantially uniform height and a predetermined inter-spacer-distance; and
xiv. at least one of the spacers is inside the sample contact area;
(c) depositing the sample on one or both of the plates when the plates are in an open configuration, wherein in the open configuration the two plates are partially or entirely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and (e) without washing, reading and analyzing signals emanating from at least part of the layer of uniform thickness, thereby determining the presence and/or quantity of the target analyte;

wherein a conformable pressing is a method that makes the pressure applied over an area is substantially constant regardless the shape variation of the outer surfaces of the plates;

and wherein the parallel pressing applies the pressures on the intended area at the same time, and a sequential pressing applies the pressure on a part of the intended area and gradually move to other area.

BA2. The device of embodiment BA1, further comprising a molecular linking layer that links said capture agents with said signal amplification layer.

BA3. The device of embodiment BA2, wherein said molecular adhesion layer is a self-assembled monolayer (SAM), wherein each molecule of the SAM comprises three parts: (i) a head group that has specific affinity to the signal amplification layer, (ii) a terminal group that specific affinity to the capture agent, and (iii) a linker that links the head group and terminal group, wherein the length of the linker determines the average spacing between the metal signal amplification layer and an attached capture agent can affects light amplification of the device.

BA4. The device of any prior embodiment, wherein the second plate sample contact area comprises a storage site containing detection agents that upon contacting the sample, dissolves into the sample and diffuses in the sample, wherein each capture agent, target analyte and corresponding detection agent is capable of forming a capture agent-target analyte-detection agent sandwich in a binding site of the first plate.

BA5. The device of any prior embodiment, wherein the second plate sample contact area comprises a storage site containing detection agents that upon contacting the sample, dissolves into the sample and diffuses in the sample, wherein the detection agent binds to the capture agent and competitively inhibits the binding between the capture agent and the target analyte.

BA6. The device of any prior embodiment, wherein the signal amplification layer comprises a continuous metallic film that is made of a material selected from the group consisting of gold, silver, copper, aluminum, alloys thereof, and combinations thereof.

BA7. The device of any prior embodiment, wherein the signal amplification layer comprises high-amplification regions and low-amplification regions, wherein the high-amplification regions amplify signals at said surface more than the low-amplification regions, wherein the low-amplification regions of the layer have been selectively masked, wherein the signal amplification layer comprises (i) two or more protrusions, (ii) two or more metal metallic structures, and (iii) two or more gaps between the metallic structures; thereby increasing the probability that a target analyte will bind to a high-amplification region and be detected.

BA8. The device of embodiment BA7, wherein the masking material is PMMA, polystyrene, a co-block polymer, silicon dioxide or silicon nitride.

BA9. The device of any of embodiments BA7-BA8, wherein the mask is of a thickness of 0.1 nm to 200 nm.

BA10. The device of any of embodiments BA7-BA9, wherein the high-amplification regions have capture agents bound thereto.

BA11. The device of any of embodiments BA7-BA10, wherein the signal amplification layer comprising:

(iv) a substantially continuous metallic backplane on the substrate;

(v) one or a plurality of dielectric or semiconductor pillars extending from the metallic backplane or from the substrate through holes in the backplane; and (vi) a metallic disk on top of the pillar, wherein at least one portion of the edge of the disk is separated from the metallic backplane by a gap;

wherein the gap(s) and portion of the metal edges are a part of the high signal amplification area.

BA12. The device of any of embodiments BA7-BA11, wherein the metallic disk has a shape selected from the group of shapes consisting of round, polygonal, pyramidal, elliptical, elongated bar shaped, or any combination thereof.

BA13. The device of any of embodiments BA7-BA12, wherein the metallic disc is separated from the metallic film by a distance in the range of 0.5 to 30 nm, and the average lateral dimension of the discs is in the range of 20 nm to 250 nm.

BA14. The device of any of embodiments BA7-BA13, wherein the signal amplification layer comprises one or more metallic discs has a shape selected from the group of shapes consisting of round, polygonal, pyramidal, elliptical, elongated bar shaped, or any combination thereof, wherein the average lateral dimension of the discs is in the range 20 nm to 250 nm, and the gap between adjacent discs in the range of 0.5 to 30 nm.

BA15. The device of any of embodiments BA7-BA14, wherein the metallic structures are made of a material that is selected from the group consisting of gold, silver, copper, aluminum, alloys thereof, and combinations thereof.

BA16. The device of any of embodiments BA7-BA15, wherein the pillars are periodic or aperiodic, or the metallic structures have a random shape.

BA17. The device of any of embodiments BA7-BA16, wherein the signal that is amplified is Raman scattering, chromaticity, luminescence, fluorescence, electroluminescence, chemiluminescence, and/or electrochemiluminescence.

BA18. The device of any prior embodiment, wherein the first plate further comprises blockers that are coated on the inner surface of the first plate.

BA19. The device of any prior embodiment, wherein the first plate and/or the second plate further comprise stabilizers that are coated on the inner surface of the respective plate.

BA20. The device of embodiment BA19, wherein the stabilizer is selected from: sugar, polymers, glycerol, and a mixture thereof.

BA21. The device of embodiment BA19, wherein the stabilizer is sucrose or glucose.

BA22. The device of any prior embodiment, wherein the target analyte is selected from the group consisting of a protein, a peptide, a DNA, an RNA, a nucleic acid, a small molecule, a cell, and a nanoparticle with different shapes.

BA23. The device of any prior embodiment, wherein the sample comprises whole blood.

BA24. The device of any prior embodiment, wherein the sample comprises blood serum.

BA25. The method of any prior method embodiment, wherein the sample is a biological sample selected from the group consisting of: cells, tissues, bodily fluids, stool, and any combination thereof.

BA26. The method of any prior method embodiment, wherein the sample is an environmental sample from an environmental source selected from the group consisting of a river, lake, pond, ocean, glaciers, icebergs, rain, snow, sewage, reservoirs, tap water, drinking water, etc.; solid samples from soil, compost, sand, rocks, concrete, wood, brick, sewage, the air, underwater heat vents, industrial exhaust, vehicular exhaust and any combination thereof.

BA27. The method of any prior method embodiment, wherein the sample is a foodstuff sample selected from the group consisting of: raw ingredients, cooked food, plant and animal sources of food, preprocessed food, partially or fully processed food, and any combination thereof.

BB2. The method of embodiment BB1, further comprising a molecular linking layer that links said capture agents with said signal amplification layer.

BB3. The method of embodiment BB2, wherein said molecular adhesion layer is a self-assembled monolayer (SAM), wherein each molecule of the SAM comprises three parts: (i) a head group that has specific affinity to the signal amplification layer, (ii) a terminal group that specific affinity to the capture agent, and (iii) a linker that links the head group and terminal group, wherein the length of the linker determines the average spacing between the metal signal amplification layer and an attached capture agent can affects light amplification of the device.

BB4. The method of any prior method embodiment, wherein the second plate sample contact area comprises a storage site containing detection agents that upon contacting the sample, dissolves into the sample and diffuses in the sample, wherein each capture agent, target analyte and corresponding detection agent is capable of forming a capture agent-target analyte-detection agent sandwich in a binding site of the first plate.

BB5. The method of any prior method embodiment, wherein the second plate sample contact area comprises a storage site containing detection agents that upon contacting the sample, dissolves into the sample and diffuses in the sample, wherein the detection agent binds to the capture agent and competitively inhibits the binding between the capture agent and the target analyte.

BB6. The method of any prior method embodiment, wherein during the step (b), the conformable pressing is by human hand.

BB7. The method of any prior method embodiment, wherein the conformable pressing of step (d) is provided by a pressured liquid, a pressed gas, or a conformal material.

BB8. The method of any prior method embodiment, before step (e) and after step (d), further comprising incubating the layer of uniform thickness for a predetermined period of time.

BB9. The method of embodiment BB8, wherein the predetermined period of time is equal to or longer than the time needed for the detection agent to diffuse into the sample across the layer of uniform thickness.

BB10. The method of any prior embodiments, wherein the sample is deposited on the first plate.

BB11. The method of any prior embodiments, before step (d) after step (c), further comprising incubating the sample on the first plate for a predetermined period of time.

BB12. The method of embodiment BB11, wherein the predetermined period of time is equal to or longer than the time needed for the binding between the capture agent and the target analyte to reach an equilibrium.

BB13. The method of any prior method embodiment, wherein the signal amplification layer comprises a continuous metallic film that is made of a material selected from the group consisting of gold, silver, copper, aluminum, alloys thereof, and combinations thereof.

BB14. The method of any prior method embodiment, wherein the signal amplification layer comprises high-amplification regions and low-amplification regions, wherein the high-amplification regions amplify signals at said surface more than the low-amplification regions, wherein the low-amplification regions of the layer have been selectively masked, wherein the signal amplification layer comprises (i) two or more protrusions, (ii) two or more metal metallic structures, and (iii) two or more gaps between the metallic structures; thereby increasing the probability that a target analyte will bind to a high-amplification region and be detected.

BB15. The method of embodiment BB14, wherein the masking material is PMMA, polystyrene, a co-block polymer, silicon dioxide or silicon nitride.

BB16. The method of any of embodiments BB14-BB15, wherein the mask is of a thickness of 0.1 nm to 200 nm.

BB17. The method of any of embodiments BB14-BB16, wherein the high-amplification regions have capture agents bound thereto.

BB18. The method of any of embodiments BB14-BB17, wherein the signal amplification layer comprising:
(i) a substantially continuous metallic backplane on the substrate;
(ii) one or a plurality of dielectric or semiconductor pillars extending from the metallic backplane or from the substrate through holes in the backplane; and
(iii) a metallic disk on top of the pillar, wherein at least one portion of the edge of the disk is separated from the metallic backplane by a gap;
wherein the gap(s) and portion of the metal edges are a part of the high signal amplification area.

BB19. The method of any of embodiments BB14-BB18, wherein the metallic disk has a shape selected from the group of shapes consisting of round, polygonal, pyramidal, elliptical, elongated bar shaped, or any combination thereof.

BB20. The method of any of embodiments BB14-BB19, wherein the metallic disc is separated from the metallic film by a distance in the range of 0.5 to 30 nm, and the average lateral dimension of the discs is in the range of 20 nm to 250 nm.

BB21. The method of any of embodiments BB14-BB20, wherein the signal amplification layer comprises one or more metallic discs has a shape selected from the group of shapes consisting of round, polygonal, pyramidal, elliptical, elongated bar shaped, or any combination thereof, wherein the average lateral dimension of the discs is in the range 20 nm to 250 nm, and the gap between adjacent discs in the range of 0.5 to 30 nm.

BB22. The method of any of embodiments BB14-BB21, wherein the metallic structures are made of a material that is selected from the group consisting of gold, silver, copper, aluminum, alloys thereof, and combinations thereof.

BB23. The method of any of embodiments BB14-BB22, wherein the pillars are periodic or aperiodic, or the metallic structures have a random shape.

BB24. The method of any of embodiments BB14-BB23, wherein the signal that is amplified is Raman scattering, chromaticity, luminescence, fluorescence, electroluminescence, chemiluminescence, and/or electrochemiluminescence.

BB25. The method of any prior method embodiment, wherein the first plate further comprises blockers that are coated on the inner surface of the first plate.

BB26. The method of any prior method embodiment, wherein the first plate and/or the second plate further comprise stabilizers that are coated on the inner surface of the respective plate.

BB27. The method of embodiment BB26, wherein the stabilizer is selected from: sugar, polymers, glycerol, and a mixture thereof.

BB28. The method of embodiment BB26, wherein the stabilizer is sucrose or glucose.

BB29. The method of any prior method embodiment, wherein the analyte is selected from the group consisting of a protein, a peptide, a DNA, an RNA, a nucleic acid, a small molecule, a cell, and a nanoparticle with different shapes.

BB30. The method of any prior method embodiment, wherein the sample comprises whole blood.

BB31. The method of any prior method embodiment, wherein the sample comprises blood serum.

BB32. The method of any prior method embodiment, wherein the sample is a biological sample selected from the group consisting of: cells, tissues, bodily fluids, stool, and any combination thereof.

BB33. The method of any prior method embodiment, wherein the sample is an environmental sample from an environmental source selected from the group consisting of a river, lake, pond, ocean, glaciers, icebergs, rain, snow, sewage, reservoirs, tap water, drinking water, etc.; solid samples from soil, compost, sand, rocks, concrete, wood, brick, sewage, the air, underwater heat vents, industrial exhaust, vehicular exhaust and any combination thereof.

BB34. The method of any prior method embodiment, wherein the sample is a foodstuff sample selected from the group consisting of: raw ingredients, cooked food, plant and animal sources of food, preprocessed food, partially or fully processed food, and any combination thereof.

The devices or methods of any prior embodiment, wherein the signal related to the analyte captured by the capture agent comes from (i) a detection agent that is captured by the analyte, (ii) an analyte that is captured by the binding site, or (iii) both (i) and (ii).

The devices or methods of any prior embodiment, wherein the measuring of the signal related to the analyte captured by the capture agent is a measurement of electrical, optical, or a combination.

C. Amplification Surface in QMAX Card

The devices or methods of any prior embodiment, wherein the device further comprises, on one or both plates, amplification surfaces that enhance the signal intensity or signal to noise ratio from labels close to it.

In some embodiments, the amplification surfaces have one layer of material.

In some embodiments, the amplification surfaces have two layers of materials, and one of the layers is continuous or non-continuous.

In some embodiments, the amplification surfaces have three or over three layers of material.

In some embodiments, the amplification surfaces have layers which are a combination of materials.

In some embodiments, the device comprises:
a first plate, a second plate, wherein:
i. the plates are movable relative to each other into different configurations;
ii. one or both plates are flexible;
iii. each of the plates comprises, on its inner surface, a sample contact area for contacting a fluidic sample;
iv. each of the plates comprises, on its respective outer surface, a force area for applying an pressing force that forces the plates together;
v. one or both of the plates comprise the amplification surfaces to amplify the signal or signal to noise ratio from labels close to it.
wherein one of the configurations is an open configuration, in which: the two plates are partially or completely separated apart, and the sample is deposited on one or both of the plates;
wherein another of the configurations is a closed configuration which is configured after the sample is deposited in the open configuration; and in the closed configuration: at least part of the sample is compressed by the two plates into a layer of highly uniform thickness and is substantially stagnant relative to the plates.

In some embodiments, one or both of the plates comprise spacers that are permanently fixed on the sample contact area of a respective plate.

In some embodiments, the spacers have a predetermined substantially uniform height.

In some embodiments, the spacers have a predetermined inter-spacer distance.

In some embodiments, at least one of the spacers is inside the sample contact area.

In some embodiments, the amplification surfaces are made of metal, including gold, silver, copper, aluminum, alloys thereof, and combinations thereof;

In some embodiments, the amplification surfaces are made of polymers (e.g. plastics) or amorphous organic materials. The polymer materials include, not limited to, acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In some embodiments, the amplification surfaces are made of inorganic materials including dielectric materials of silicon oxide, porcelain, orcelain (ceramic), mica, glass, oxides of various metals, etc.

In some embodiments, the amplification surfaces are made of inorganic compounds including, but not limited to, aluminium oxide, aluminium chloride, cadmium sulfide, gallium nitride, gold chlorid, indium arsenide, lithium borohydride, silver bromide, sodium chloride, etc.

The signal amplification layer comprises a continuous metallic film including, but not limited to, gold, silver, copper, aluminum, alloys thereof, and combinations thereof.

The signal amplification layer comprises high-amplification regions and low-amplification regions, wherein the high-amplification regions amplify signals at said surface more than the low-amplification regions, wherein the low-amplification regions of the layer have been selectively masked, wherein the signal amplification layer comprises (i) two or more protrusions, (ii) two or more metal metallic structures, and (iii) two or more gaps between the metallic structures; thereby increasing the probability that a target analyte will bind to a high-amplification region and be detected.

In some embodiments, the signal amplification layer comprising:
  (i) a substantially continuous metallic backplane on the substrate;
  (ii) one or a plurality of dielectric or semiconductor pillars extending from the metallic backplane or from the substrate through holes in the backplane; and
  (iii) a metallic disk on top of the pillar, wherein at least one portion of the edge of the disk is separated from the metallic backplane by a gap;
wherein the gap(s) and portion of the metal edges are a part of the high signal amplification area, wherein the metallic disk has a shape selected from the group of shapes consisting of round, polygonal, pyramidal, elliptical, elongated bar shaped, or any combination thereof. The metallic disc is separated from the metallic film by a distance in the range of 0.5 to 30 nm, and the average lateral dimension of the discs is in the range of 20 nm to 250 nm; wherein the signal amplification layer comprises one or more metallic discs has a shape selected from the group of shapes consisting of round, polygonal, pyramidal, elliptical, elongated bar shaped, or any combination thereof, wherein the average lateral dimension of the discs is in the range 20 nm to 250 nm, and the gap between adjacent discs in the range of 0.5 to 30 nm.

wherein the metallic structures are made of a material that is selected from the group consisting of gold, silver, copper, aluminum, alloys thereof, and combinations thereof.

wherein the pillars are periodic or aperiodic, or the metallic structures have a random shape.

In some embodiments, the amplification surface comprises a layer of nanostructures made of metallic materials and dielectric/semiconductor materials, that can enhance the signal. Often the outer surface of the amplification surface (the inner surface of amplification surface is the surface in contact with the substrate surface) is coated with a molecular adhesion/spacer layer, which serves one of the two or both of the functions: (1) provide a good adhesion to bond to the capture agents, and (2) a spacer that control the distance between the metal in the amplification surface and the signal generation molecule to optimize signal amplification. One preferred amplification surface embodiment is that the dimension of one, several or all critical metallic and dielectric components of SAL are less than the wavelength of the light in sensing.

In some embodiments, the amplification layer comprises a D2PA array. The terms "disk-coupled dots-on-pillar antenna array" and "D2PA" as used herein refer to an array that comprises: (a) substrate; and (b) a D2PA structure, on the surface of the substrate, comprising one or a plurality of pillars extending from a surface of the substrate, wherein at least one of the pillars comprises a pillar body, metallic disc on top of the pillar, metallic backplane at the foot of the pillar, the metallic back plane covering a substantial portion of the substrate surface near the foot of the pillar; metallic dot structure disposed on sidewall of the pillar. The D2PA amplifies a light signal that is proximal to the surface of the D2PA. The D2PA enhances local electric field and local electric field gradient in regions that is proximal to the surface of the D2PA. The light signal includes light scattering, light diffraction, light absorption, nonlinear light generation and absorption, Raman scattering, chromaticity, luminescence that includes fluorescence, electroluminescence, chemiluminescence, and electrochemiluminescence.

A D2PA array may also comprise a molecular adhesion layer that covers at least a part of said metallic dot structure, said metal disc, and/or said metallic back plane and, optionally, a capture agent that specifically binds to an analyte, wherein said capture agent is linked to the molecular adhesion layer of the D2PA array. The nanosensor can amplify a light signal from an analyte, when said analyte is bound to the capture agent. One preferred amplification surface embodiment is that the dimension of one, several or all critical metallic and dielectric components of SAL are less than the wavelength of the light in sensing.

In some embodiments, the amplification surface includes, but not limited to, the proximity-dependent signal amplification layers described in U.S. Provisional Patent Application No. 61/347,178, which was filed on May 21, 2010, U.S. Provisional Patent Application No. 61/622,226, which was filed on Apr. 10, 2012, U.S. Provisional Patent Application No. 61/708,314, which was filed on Oct. 1, 2012, U.S. Provisional Patent Application No. 61/800,915, which was filed on Mar. 15, 2013, U.S. Provisional Patent Application No. 61/801,933, which was filed on Mar. 15, 2013, U.S. Provisional Patent Application No. 61/801,096, which was filed on Mar. 15, 2013, U.S. Provisional Patent Application No. 61/801,424, which was filed on Mar. 15, 2013, U.S. Provisional Patent Application No. 61/794,317, which was filed on Mar. 15, 2013, U.S. Provisional Patent Application No. 62/090,299, which was filed on Dec. 10, 2014, U.S. Provisional Patent Application No. 62/066,777, which was filed on Oct. 21, 2014, U.S. Provisional Patent Application No. 62/234,538, which was filed on Sep. 29, 2015, U.S. Utility patent application Ser. No. 13/699,270, which was filed on Jun. 13, 2013, U.S. Utility patent application Ser. No. 13/838,600, which was filed on Mar. 15, 2013, U.S. Utility patent application Ser. No. 14/459,239, which was filed on Aug. 13, 2014, U.S. Utility patent application Ser. No. 14/459,251, which was filed on Aug. 13, 2014, U.S. Utility patent application Ser. No. 14/852,412, which was filed on Mar. 16, 2014, U.S. Utility patent application Ser. No. 14/871,678, which was filed on Sep. 30, 2015, U.S. Utility patent application Ser. No. 14/431,266, which was filed on Oct. 5, 2015, U.S. Utility patent application Ser. No. 14/668,750, which was filed on Mar. 25, 2015, U.S. Utility patent application Ser. No. 14/775,634, which was filed on Sep. 11, 2015, U.S. Utility patent application Ser. No. 14/775,638, which was filed on Sep. 11, 2015, U.S. Utility patent application Ser. No. 14/852,417, which was filed on Sep. 11, 2015, U.S. Utility patent application Ser. No. 14/964,394, which was filed on Dec. 9, 2015, PCT Application (designating U.S.) No. PCT/US2011/037455, which was filed on May 20, 2011, PCT Application (designating U.S.) No. PCT/US2013/032347, which was filed on Mar. 15, 2013, PCT Application (designating U.S.) No. PCT/US2013/062923, which was filed on Oct. 1, 2013, PCT Application (designating U.S.) No. PCT/US2014/030108, which was filed on Mar. 16, 2014, PCT Application (designating U.S.) No. PCT/US2014/029675, which was filed on Mar. 14, 2014, PCT Application (designating U.S.) No. PCT/US2014/028417, which was filed on Mar. 14, 2014, PCT Application (designating U.S.) No. PCT/US2014/029979, which was filed on Mar. 15, 2014, PCT Application (designating U.S.) No. PCT/US2015/056518, which was filed on Oct. 20, 2015, PCT Application (designating U.S.) No. PCT/US2016/054025, which was filed on Sep. 27, 2016, the complete disclosures of which are hereby incorporated by reference for all purposes.

In some embodiments, the amplification surface has a thickness of 1 nm, 10 nm, 50 nm, 100 nm, 200 nm, 500 nm, 1 um, 2 um, 5 um, 10 um, or in a range between any two of these values.

In some embodiments, the amplification surface has a preferred thickness of 1 nm to 10 nm.

In some embodiments, the amplification surface has a preferred thickness of 10 nm to 100 nm.

In some embodiments, the amplification surface has a preferred thickness of 100 nm to 200 nm.

In some embodiments, wherein the amplification surface has a preferred thickness of 200 nm to 500 nm.

In some embodiments, the signal get amplified is an electromagnetic signal, including electrical and optical signals with different frequencies, light intensity, fluorescence, chromaticity, luminescence (electrical and chemo-luminescence), Raman scattering, time resolved signal (including blinking).

In some embodiments, the label is a molecule or protein based reporter, including but not limit to IRDye800CW, Cy-3, Cy-5, Cy-7, Alexa 790, Dylight 800, Phycoerythrin, fluorescein, fluorescein isothiocyanate, succinimidyl esters of carboxyfluorescein, succinimidyl esters of fluorescein, isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), 15 tetramethylrosamine, rhodamine B and 4-dimethylaminotetramethylrosamine, green fluorescent protein, blue-shifted green fluorescent protein, cyan-shifted green fluorescent protein, redshifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-20 vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethyl-coumarin (Coumarin 151); cyanine dyes; cyanosine; 4',6-diaminidino-2-phenylindole (DAPI); 5',5"-dibromopyrogallol25 sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino] naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: 30 erythrosin B, erythrosin, isothiocyanate; ethidium; fluorescein and derivatives: 5-carboxyfluorescein (FAM),5-(4,6-dichlorotriazin-2-yl)aminofluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of 5 sulforhodamine 101 (Texas Red); N,N,N', N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; 10 La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as Renilla reniformis, Renilla mulleri, or Ptilosarcus guernyi; "humanized" recombinant GFP (hrGFP); any of a variety of fluorescent and colored proteins from Anthozoan species; combinations thereof; and the like.

In some embodiments, wherein the label is a particle or bead reporter, including but not limit to gold nanoparticle, silver nanoparticle, silicon quantum dots, CdSe quantum dots, silicon nanowires, melamine resin particles, fluorescently labeled and carboxylate-modified melamine microparticles, fluorescent nanobeads (nanoparticles), polyacrylnitrile (pan) nanoparticles, fluorescent polystyrene beads, latex particles etc.

In some embodiments, when using particle or beads as the label, the average particle or beads size is 1 nm to 10 nm.

In some embodiments, when using particle or beads as the label, the average particle or beads size is 10 nm to 50 nm.

In some embodiments, when using particle or beads as the label, the average particle or beads size is 50 nm to 100 nm.

In some embodiments, when using particle or beads as the label, the average particle or beads size is 100 nm to 500 nm.

In some embodiments, when using particle or beads as the label, the average particle or beads size is 500 nm to 1 um.

In some embodiments, when using particle or beads as the label, the average particle or beads size is 1 um to 2 um.

In some embodiments, the label is within 1 nm distance from the amplification surface.

In some embodiments, the label is within 5 nm distance from the amplification surface.

In some embodiments, the label is within 10 nm distance from the amplification surface.

In some embodiments, the label is within 100 nm distance from the amplification surface.

In some embodiments, he label is within 500 nm distance from the amplification surface.

In some embodiments, the label is within 10 um distance from the amplification surface.

In some embodiments, the label is within 50 um distance from the amplification surface.

In some embodiments, the label is within 100 um distance from the amplification surface.

In some embodiments, the label is within 200 um distance from the amplification surface.

In some embodiments, the excitation light source and detector are at the same front side of the device.

In some embodiments, the excitation light source and detector are at the same back side of the device.

In some embodiments, one of the excitation light source and detector are at the front side of the device.

In some embodiments, one of the excitation light source and detector are at the back side of the device.

In some embodiments, one of the excitation light source and detector are at the same plane of the device and face to the device.

In some embodiments, both the excitation light source and detector are at the same plane of the device.

Signal Amplification by Having a Metal Layer on QMAX Card.

Our experiments have found that by putting a thin metal layer on or near the inner surface of a plate of QMAX card, the metal layer can enhance light signal of a light emitter near the metal. The light emitter can be light excited, electrically excited, or chemically excited. The light emitter can a fluorescence label, or beads, and other light emitters. The metal layer be next to the light emitter, or some distance away. Our experiments showed that for signal enhencement the distance between the light emitter and the metal layer can be 5 nm, 10 nm, 50 nm, 100 nm, 200 nm, 300 nm, 500 nm, 1 um, 5 um, 10 um, 20 um, 30 um, 40 um, 100 um, or in a range of any two of the value. The distance between the light emitter and the metal can be filled with dielectrics. In some embodiment, the metal layer put on a QMAX-card and use QMAX card to measure the sample volume, speed up the assay, having binding sites, adding reagents, or any combination of thereof. Below are some experimental observations of the metal layer enhancement of a light emitter.

FIG. 12 shows schematics of amplification surfaces with (a) plate have one layer of material; (b) plate have two layers of material (one of the layers is continuous or non-continuous); (c) plate have three or over three layers of material; (d) plate have layers which are the combination of materials. Labels are on top surface of the device.

Figure 22:
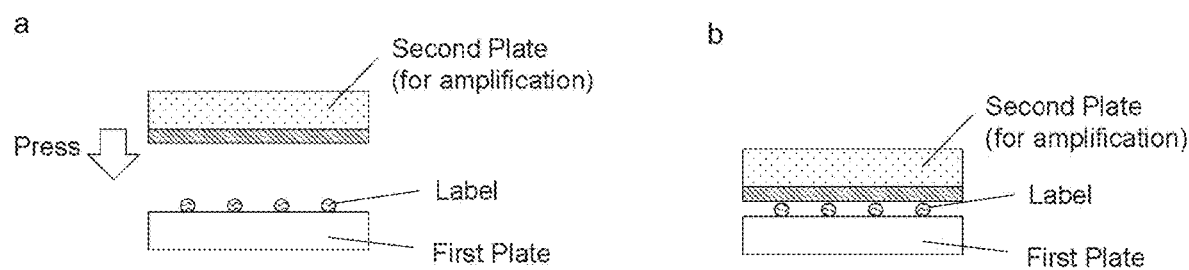
FIG. 22 shows schematics of amplification device with two plates, where first plate with label on top surface; and second plate for amplification. The device has (a) open configuration and (b) close configuration.

FIG. 22 shows schematics of amplification device with two plates, where first plate with label on top surface; and second plate for amplification. The device has (a) open configuration and (b) close configuration.

FIG. 23 shows schematics of one experiment as example using device shown in FIG. X1. (a) Fluorescence dye or beads on top surface of one layer device; (b) Fluorescence dye or beads on top of two layer device (metal and dielectric material); (c) Fluorescence dye or beads on top of the two layer device (dielectric material and metal).

Here the fluorescence dye is Antibody conjugated Cy-5 dye 100 nM, volume 10 uL, dried in black chamber 37° C. for 1 h.

Fluorescence bead is 40 nm Streptavidin conjugated fluorescence bead 1010/mL, volume 10 uL, dried in black chamber 37° C. for 1 h.

For detecting fluorescence from small molecule dye, 1 mW 633 nm laser is the excitation light source, a spectrometer and photodetector with filters are the detectors.

For detecting fluorescence from beads, 1 mW 532 nm laser is the excitation light source, a spectrometer and photodetector with filters are the detectors.

Figure 24:
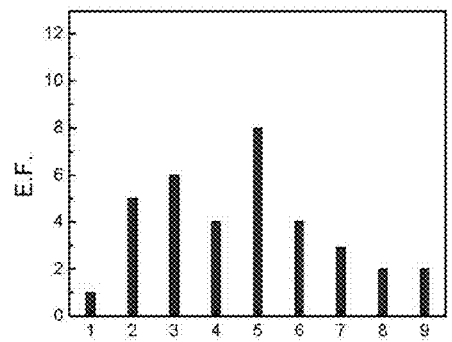
FIG. 24 shows experimental results of fluorescence molecule enhancements with setup shown in FIG. 23. E.F. gives the enhancements for different devices.

FIG. 24 shows experimental results of fluorescence molecule enhancements with setup shown in FIG. 23. E.F. gives the enhancements for different devices.

Gold and aluminum coated thin substrate (25 um to 50 um) have fluorescence enhancement 3 to 8 times for both small molecule dye on metal or glass/plastic side;

Gold and aluminum coated thick substrate (thicker than 175 um to 1000 um) have fluorescence enhancement 4 to 8 times for small molecule dye on metal side, 2 times for small molecule dye on glass/plastic side.

FIG. 25 shows experimental results of fluorescence beads enhancements with setup shown in FIG. 23. E.F. gives the enhancements for different devices.

Gold and aluminum coated thin substrate (25 um to 50 um) have fluorescence enhancement 6 to 12 times for both beads on metal or glass/plastic side;

Gold and aluminum coated thick substrate (thicker than 175 um to 1000 um) have fluorescence enhancement 6 to 12 times for beads on metal side, 1 to 2 times for beads on glass/plastic side.

Figure 26:
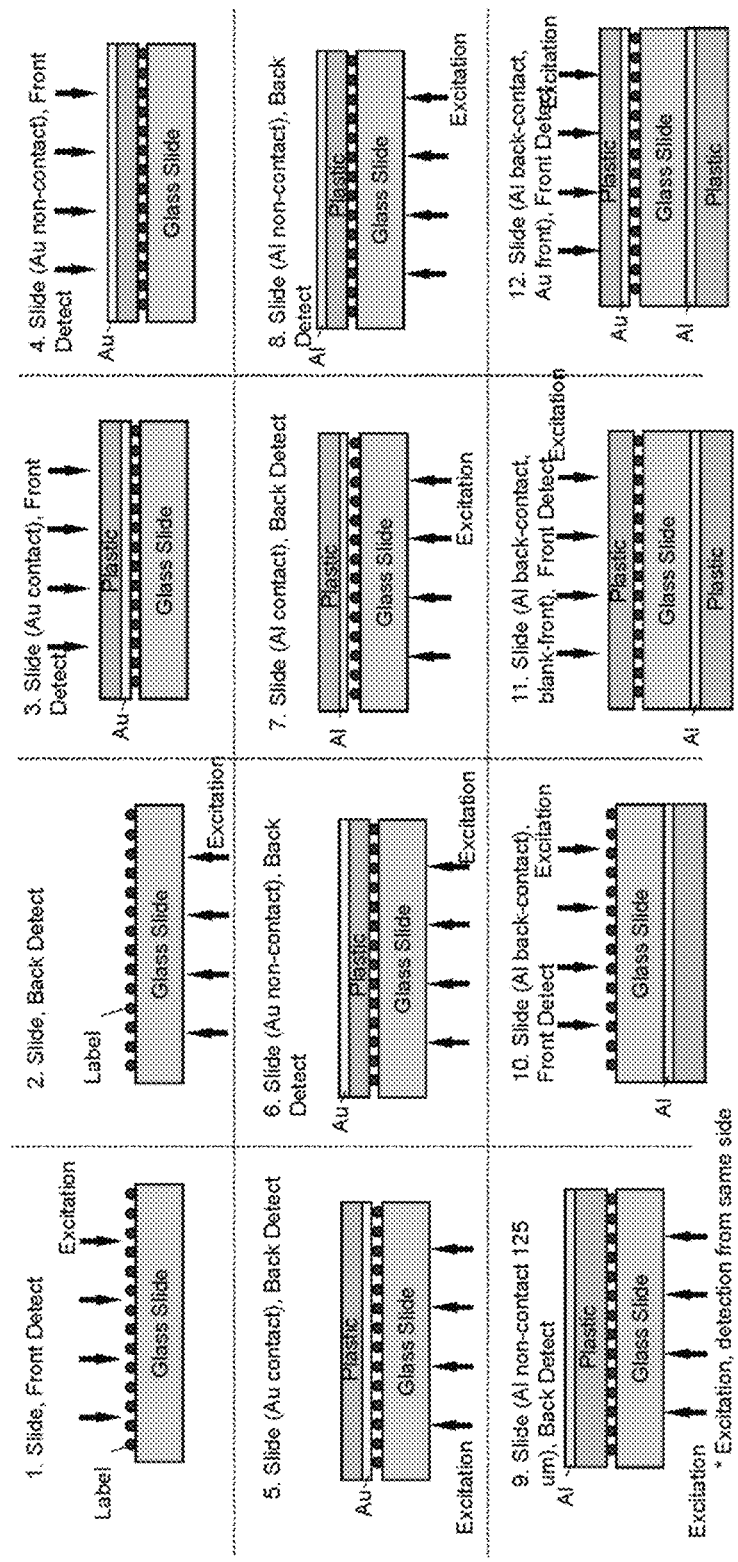
FIG. 26 shows schematics of one experiment as example using device shown in FIG. 22.

FIG. 26 shows schematics of one experiment as example using device shown in FIG. 22. (1) Label on top of glass slide, with excitation and detection both at front side; (2) Label on top of glass slide, with excitation at back side and detection at front side; (3)-(10) Label sandwiched between a glass slide and two layer device (metal and plastics), excitation and detection are at one side or different side; (11)-(12) Label sandwiched between two devices, each device has one layer, two layers or three layers, excitation and detection both at front side. Here the fluorescence dye is Antibody conjugated Cy-5 or IR-800 dye 100 nM, volume 10 uL, dried in black chamber 37° C. for 1 h.

Figure 27:
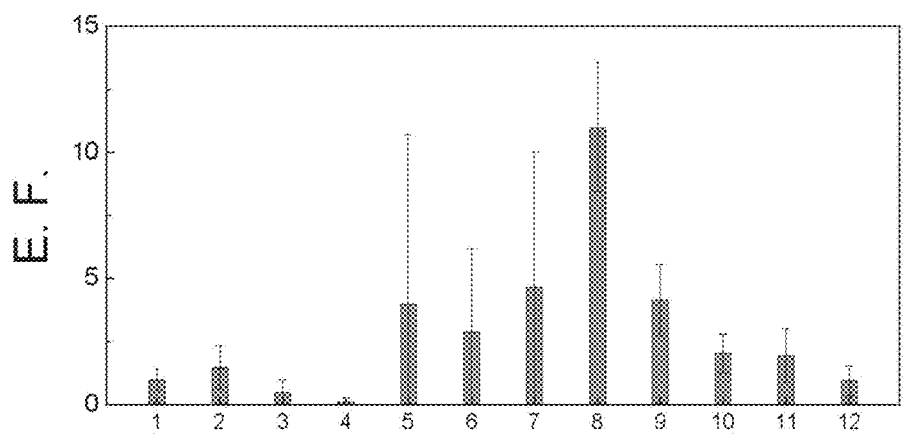
FIG. 27 shows experimental results of fluorescence molecule (Cy-5 dye) enhancements with setup shown in FIG. 26. E.F. gives the enhancements for different devices

FIG. 27 shows experimental results of fluorescence molecule (Cy-5 dye) enhancements with setup shown in FIG. 26. E.F. gives the enhancements for different devices FIG. 28 shows experimental results of fluorescence molecule (IR-800 dye) enhancements with setup shown in FIG. 26. E.F. gives the enhancements for different devices A "capture component", as used herein, is any molecule, other chemical/biological entity or solid support modification disposed upon a solid support that can be used to specifically attach, bind or otherwise capture a target molecule or particle (e.g., an analyte molecule or dissociated species), such that the target molecule/particle becomes immobilized with respect to the capture component and solid substrate. As used herein, "immobilized" means captured, attached, bound, or affixed so as to prevent dissociation or loss of the target molecule/particle, but does not require absolute immobility with respect to either the capture component or the solid substrate. Capture components which are useful or potentially useful for practicing certain aspects and embodiments of the invention are discussed in more detail below. At least some of the analyte molecules, upon exposure to the substrate comprising a plurality of capture components, can become immobilized with respect to a capture component, thereby forming a plurality of immobilized complexes. For example, in certain embodiments, substantially all of the plurality of analyte molecules may become immobilized with respect to capture components such that essentially each of the plurality of immobilized complexes comprises a capture component and an analyte molecule.

A "binding ligand," as used herein, is any molecule, particle, or the like which specifically binds to or otherwise specifically associates with an analyte molecule, immobilized complex and/or dissociated species or another molecule or particle bound to or otherwise associated with the analyte molecule, immobilized complex and/or dissociated species (e.g., another binding ligand). In certain embodiments, the binding ligand can convert a precursor labeling agent molecule to a labeling agent, as discussed more below. More than one type of binding ligand may be employed in any given assay method, for example, a first type of binding ligand and a second type of binding ligand. In one example, the first binding ligand is able to associate with an analyte molecule and the second binding ligand is able to associate with the first binding ligand. When the substrate is exposed to a plurality of types of binding ligand, at least some of the plurality of immobilized complexes may additionally comprise, in some cases, at least one of each type of binding ligand. In certain embodiments, the binding ligand can be exposed to the substrate after capture of the analyte molecule so that the binding ligand binds to the immobilized complex. In other embodiments, the binding ligand may become associated with the analyte molecule to form a complex followed by capture of the complex by the substrate to form the immobilized complex. In yet other embodiments, the binding ligand may bind to the dissociated species formed upon release of the immobilized complex, or portion thereof, from the substrate.

In some embodiments, the immobilized complex comprises a cleavable linkage. A "cleavable linkage," as used herein, is linkage that is able to be readily (i.e. Under conditions not detrimental to the integrity of other portions of the immobilized complex) and selectively cleaved upon exposure to a dissociating agent. The cleavable linkage upon cleavage by exposure to a dissociating agent forms the dissociated species. One specific example of a cleavable linkage, which can be cleaved using beta-mercaptoethanol, is a disulfide linkage. Cleavable linkages and corresponding dissociating agents that can cause the cleavable linkage to cleave are discussed in more detail below.

In some embodiments, the plurality of molecules may be released from the first substrate by exposure to a dissociating agent. For example, a substrate comprising a plurality of capture components may be exposed to a sample comprising a plurality of analyte molecules or particles, such that analyte molecules or particles associate with capture components to form a plurality of complexes, which are immobilized with respect to the substrate. Each of the immobilized complexes may comprise at least one capture component and at least one analyte molecule or particle. Exposure of the plurality of immobilized complexes to a reducing agent (e.g., beta-mercaptoethanol, dithiothreitol, tris(2-carboxyethyl)phosphine, etc.) Causes at least a portion of at least some of the plurality of immobilized complexes to dissociate from the substrate to form a plurality of dissociated species. At least some of the dissociated species may be detected to determine the presence of and/or a measurement of the amount or concentration of the analyte molecules or particles in the fluid sample, as discussed more herein. The reducing agent may or may not be removed form the solution comprising the dissociated species prior to detection of the dissociated species, as discussed more herein. In some embodiments, the dissociating agent is a reducing agent (e.g., beta-mercaptoethanol). In some embodiments, the dissociating agent has essentially no specific affinity for the capture components. That is, the dissociating agent does not bring about release of the dissociating species by interacting with the capture component and employing competitive binding to release the analyte molecule that associated with the capture component.

In some embodiments, the plurality of dissociated species may be formed by cleavage of cleavable linkages. For example, each of the immobilized complexes may comprise at least one cleavable linkage (e.g., a disulfide linkage). The cleavable linkage may located in a capture component, analyte molecule or a binding ligand and may be cleaved to form a plurality of dissociated species, for example, see FIG. 4 as discussed more herein. In a particular embodiment, the cleavable linkage is a disulfide linkage which may, in some cases, be cleaved by exposure of the immobilized complexes to a reducing agent.

In some embodiments, at least a portion of an immobilized complex comprises an enzymatic component. That is, at least one of the capture component, the analyte molecule or any additional components of the immobilized complex (e.g., binding ligand(s)) comprises an enzymatic component. In some cases, the enzymatic component may be located in the portion of the immobilized complex which is dissociated from the first substrate to form a dissociated species. For example, FIG. 8 illustrate an exemplary embodiment of an assay wherein the binding ligand comprises a moiety (e.g., an enzymatic component), as discussed more herein.

In certain embodiments, the protocol may include the use of at least one binding ligand, at least a portion of which comprises at least a portion of the dissociated species transferred from the first substrate to the second substrate (e.g., the binding ligand may be immobilized prior to release or following release of the molecules or particles from the first substrate). In some embodiments, the binding ligand comprises a cleavable linkage (e.g., a disulfide linkage) and/or is dissociated from the first substrate by exposure to a reducing agent. In some embodiments, at least one binding ligand comprises an enzymatic component. For example, the binding ligand(s), or at least the portions thereof forming at least a portion of the dissociated species transferred from the first substrate to the second substrate, may further comprise a moiety (e.g., an enzymatic component or enzyme substrate) able to convert a precursor labeling agent molecule (e.g., an enzymatic substrate) into a labeling agent (e.g., a detectable product). After transfer of and, optionally, capture of the dissociated species on or within the second substrate, the second substrate may be exposed to a plurality of precursor labeling agent molecules, wherein the plurality of precursor labeling agent molecules are converted to a plurality of labeling agent molecules upon exposure to a binding ligand. A measure of the concentration of the analyte molecules or particles in the fluid sample can then be determined based on the measurement of the labeling agent molecules on or within the second substrate.

Metal Layers in Microwell

Below it assumes that a metal layer in microwell.

A method of detecting analyte molecules or particles in QMAX device, comprising:

(a) obtaining a sample comprising a plurality of analyte molecules or particles;

(b) obtaining a QMAX device that comprises:

a first plate, a second plate, and spacers, wherein:

i. the plates are movable relative to each other into different configurations;

ii. one or both plates are flexible;

iii. one or both plates have a plurality of reaction vessels;

iv. each of the plates comprises an inner surface that has a sample contact area for contacting a blood sample;

v. one or both of the plates comprising a plurality of capture components;

vi. one or both of the plates comprise the spacers that are permanently fixed on the sample contact area of a respective plate;

vii. the spacers have:
- (1) a predetermined substantially uniform height that has a value selected in the range of 1 um to 80 um,
- (2) a shape of pillar with substantially uniform cross-section and a flat top surface;
- (3) a ratio of the width to the height equal or larger than one;
- (4) a predetermined fixed, non-random, inter-spacer distance that is in the range of 10 um to 200 um (micron); and (c) depositing the sample on one or both of the plate, exposing the plate comprising a plurality of capture components to a sample comprising a plurality of analyte molecules or particles, so that analyte molecules or particles associate with capture components to form a plurality of complexes, each complex being immobilized with respect to the plate and comprising at least one capture component and at least one analyte molecule or particle;

(d) dissociating at least a portion of each complex to form a plurality of dissociated species, which are not immobilized with respect to the plate;

(e) partitioning the plurality of dissociated species across a plurality of reaction vessels;

(f) determining the presence or absence of a dissociated species in at least one reaction vessel;

(g) determining the number of the plurality of reaction vessels and/or fraction of the plurality of reaction vessels that contain or do not contain a dissociated species, wherein the plurality of dissociated species are partitioned such that a statistically significant fraction of the reaction vessels contain no dissociated species and a statistically significant fraction of reaction vessels contain at least one dissociated species.

A method for determining a measure of the concentration of analyte molecules or particles in a fluid sample, comprising:

capturing a plurality of analyte molecules or particles on a first plate;

releasing a plurality of molecules or particles from the first plate;

detecting molecules or particles released from the first plate on or within a second plate comprising a plurality of reaction vessels;

and determining a measure of the concentration of the analyte molecules or particles in the fluid sample based on the detection of molecules or particles released from the first plate on or within the second plate, wherein the measure of the concentration of the analyte molecules or particles in the fluid sample is determined by determining the number or fraction of the plurality of reaction vessels that contain or do not contain a molecule or particle released from the first plate.

The method or device of any prior embodiment, wherein the number or fraction of the plurality of reaction vessels that contain a dissociated species is related to the concentration of analyte molecules or particles in the sample.

The method or device of any prior embodiment, further comprising an act of determining the concentration of analyte molecules or particles in the fluid sample.

The method or device of any prior embodiment, wherein the plate comprises a plurality of beads.

The method or device of any prior embodiment, wherein the beads are magnetic.

The method or device of any prior embodiment, wherein the plate comprises a microtiter plate.

The method or device of any prior embodiment, wherein the plurality of reaction vessels are formed upon the mating of at least a portion of a sealing component and at least a portion of a second plate.

The method or device of any prior embodiment, wherein the plurality of reaction vessels are defined on a planar second plate.

The method or device of any prior embodiment, wherein the volume of each of the plurality of reaction vessels is between about 10 attoliters and about 100 picoliters.

The method or device of any prior embodiment, wherein each of the plurality of reaction vessels comprise at least one dissociated species capture component.

The method or device of any prior embodiment, further comprising immobilizing at least one of the plurality of dissociated species with respect to the at least one dissociated species capture component.

The method or device of any prior embodiment, wherein each of the plurality of reaction vessels is exposed to at least one precursor labeling agent molecule.

The method or device of any prior embodiment, wherein the at least one precursor labeling agent molecule is converted to a labeling agent molecule when contained in a reaction vessel comprising a dissociated species.

The method or device of any prior embodiment, wherein the presence or absence of a dissociated species in a reaction vessel is determined by determining the presence or absence of a labeling agent molecule in the reaction vessel.

The method or device of any prior embodiment, wherein the plate is exposed to a plurality of first binding ligands.

The method or device of any prior embodiment, wherein a first binding ligand associates with each of the plurality of analyte molecules or particles in the exposing act to form at least a portion of the plurality of complexes.

The method or device of any prior embodiment, wherein each first binding ligand comprises an enzymatic component.

The method or device of any prior embodiment, wherein the first binding ligand comprises a cleavable linkage.

The method or device of any prior embodiment, wherein the plurality of dissociated species is formed by cleaving at least some of the cleavable linkages.

The method or device of any prior embodiment, wherein at least one of the plurality of dissociated species comprises at least a portion of a first binding ligand.

The method or device of any prior embodiment, wherein the plurality of dissociated species are formed by exposing the plate to electromagnetic radiation.

The method or device of any prior embodiment, wherein the plurality of dissociated species are formed by exposing the plate to a dissociating agent.

The method or device of any prior embodiment, wherein the dissociating agent comprises at least one of a pH agent, salt agent, denaturing agent, reducing agent, chemical agent, or enzyme.

The method or device of any prior embodiment, wherein the analyte molecules or particles are proteins.

The method or device of any prior embodiment, wherein the capture component is an antibody.

The method or device of any prior embodiment, further comprising sealing the plurality of reaction vessels.

The method or device of any prior embodiment, wherein the first plate comprises a plurality of first capture components.

The method or device of any prior embodiment, wherein at least one of the plurality of analyte molecules or particles is captured by being specifically immobilized with respect to at least one of the plurality of first capture components.

The method or device of any prior embodiment, further comprising the act of exposing the plurality of analyte molecules or particles captured on the first plate to a plurality of first binding ligands.

The method or device of any prior embodiment, wherein at least one of the plurality of first binding ligands becomes immobilized with respect to each of at least a fraction of the plurality of analyte molecules or particles captured on the first plate.

The method or device of any prior embodiment, wherein the releasing act comprises exposing the plate to electromagnetic radiation.

The method or device of any prior embodiment, wherein the releasing act comprises exposing the plate to a dissociating agent.

The method or device of any prior embodiment, wherein the second plate comprises a plurality of second capture components.

The method or device of any prior embodiment, wherein each of at least a fraction of the plurality of molecules or particles released from the first plate become immobilized with respect to at least one second capture component on the second plate.

The method or device of any prior embodiment, further comprising an act of sealing at least a fraction of the plurality of reaction vessels.

The method or device of any prior embodiment, wherein the measure of the concentration of the analyte molecules or particles in the fluid sample is determined at least in part by a Poisson distribution analysis of the number or fraction of the plurality of reaction vessels that contain an analyte molecule or particle released from the plate.

The method or device of any prior embodiment, wherein less than about 80% of the total number of the plurality of reaction vessels contain at least one analyte molecule or particle released from the plate.

The method or device of any prior embodiment, wherein the second plate comprises a planar surface and a sealing component comprising a plurality of microwells, and the plurality of reaction vessels are formed upon mating of at least a portion of the planar plate with at least a portion of the sealing component.

Label Beads with Different Color Code for Multiplexing:

The devices or methods of any prior embodiment, wherein the label is beads containing color bar-code.

The devices or methods of any prior embodiment, wherein the beads with one kind of color bar-codes contains reagent that have affinity for one kind of analyte.

The devices or methods of any prior embodiment, wherein the number of beads of each kind of bar-code that captures specific kind of analyte are statistical significant.

The devices or methods of any prior embodiment, wherein the label is beads with different geometric sizes, wherein the sizes include, but not limited to, sphere, cube, cuboid, tetrahedron.

The devices or methods of any prior embodiment, wherein the microwells have different geometric shape, wherein each one shape of microwell can only accommodate one geometric size of beads The devices or methods of any prior embodiment, wherein the beads with different geometric sizes contains capture agent for different analyte.

The devices or methods of any prior embodiment, wherein the number of beads of each individual geometric size that captures specific analyte are statistical significant.

The devices or methods of any prior embodiment wherein the quantification by using the ratio of number of labels to the number of spacer/pillars]

A method for determining a measure of the concentration of analyte molecules or particles in a fluid sample on QMAX card, comprising:

Perform assay on QMAX card using beads as label; Determining a measure of the concentration of analyte in the sample based on the ratio of the number of beads determined to bound with analyte molecule to the number of spacers (pillars).

Other Embodiments and Related Disclosures

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(6) Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

Flat Top of Pillar Spacers

In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, or in a range between any two of the values. A preferred flat pillar top smoothness is that surface variation of 50 nm or less.

Furthermore, the surface variation is relative to the spacer height and the ratio of the pillar flat top surface variation to the spacer height is less than 0.5%, 1%, 3%,5%,7%,10%, 15%, 20%, 30%,40%, or in a range between any two of the values. A preferred flat pillar top smoothness has a ratio of the pillar flat top surface variation to the spacer height is less than 2%, 5%, or 10%.

Sidewall Angle of Pillar Spacers

In certain embodiments of the present invention, the spacers are pillars that have a sidewall angle. In some embodiments, the sidewall angle is less than 5 degree (measured from the normal of a surface), 10 degree, 20 degree, 30 degree, 40 degree, 50 degree, 70 degree, or in a range between any two of the values. In a preferred embodiment, the sidewall angle is less 5 degree, 10 degree, or 20 degree.

Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm$^2$ (centimeter square) to 100 kg/cm$^2$, (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 um×10 um), a nearly uniform cross-section and 2 um tall, and the spacers are periodic with a period of 100 um, then the filing factor of the spacer is 1%. If in the above example, the foot of the pillar spacer is a square shape of 15 um×15 um, then the filling factor is still 1% by the definition.

The method or device of any prior embodiment, wherein the spacers have pillar shape and nearly uniform cross-section.

The method or device of any prior embodiment, wherein the inter spacer distance (SD) is equal or less than about 120 um (micrometer).

The method or device of any prior embodiment, wherein the inter spacer distance (SD) is equal or less than about 100 um (micrometer).

The method or device of any prior embodiment, wherein the fourth power of the inter-spacer-distance (ISD) divided by the thickness (h) and the Young's modulus (E) of the flexible plate (ISD4/(hE)) is 5×106 um3/GPa or less.

The method or device of any prior embodiment, wherein the fourth power of the inter-spacer-distance (ISD) divided by the thickness (h) and the Young's modulus (E) of the flexible plate (ISD4/(hE)) is 5×105 um3/GPa or less.

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD4/(hE)) is 5×106 um3/GPa or less.

The device of any prior device embodiment, wherein the ratio of the inter-spacing distance of the spacers to the average width of the spacer is 2 or larger, and the filling factor of the spacers multiplied by the Young's modulus of the spacers is 2 MPa or larger.

The method or device of any prior embodiment, wherein the analytes is proteins, peptides, nucleic acids, synthetic compounds, or inorganic compounds.

The method or device of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The method or device of any prior embodiment, wherein the spacers have a shape of pillars and a ratio of the width to the height of the pillar is equal or larger than one.

The method of any prior embodiment, wherein the sample that is deposited on one or both of the plates has an unknown volume.

The method or device of any prior embodiment, wherein the spacers have a shape of pillar, and the pillar has substantially uniform cross-section.

The method or device of any prior embodiment, wherein the samples is for the detection, purification and quantification of chemical compounds or biomolecules that correlates with the stage of certain diseases.

The method or device of any prior embodiment, wherein the samples is related to infectious and parasitic disease, injuries, cardiovascular disease, cancer, mental disorders, neuropsychiatric disorders, pulmonary diseases, renal diseases, and other and organic diseases.

The method or device of any prior embodiment, wherein the samples is related to the detection, purification and quantification of microorganism.

The method or device of any prior embodiment, wherein the samples is related to virus, fungus and bacteria from environment, e.g., water, soil, or biological samples.

The method or device of any prior embodiment, wherein the samples is related to the detection, quantification of chemical compounds or biological samples that pose hazard to food safety or national security, e.g. toxic waste, anthrax.

The method or device of any prior embodiment, wherein the samples is related to quantification of vital parameters in medical or physiological monitor.

The method or device of any prior embodiment, wherein the samples is related to glucose, blood, oxygen level, total blood count.

The method or device of any prior embodiment, wherein the samples is related to the detection and quantification of specific DNA or RNA from biosamples.

The method or device of any prior embodiment, wherein the samples is related to the sequencing and comparing of genetic sequences in DNA in the chromosomes and mitochondria for genome analysis.

The method or device of any prior embodiment, wherein the samples is related to detect reaction products, e.g., during synthesis or purification of pharmaceuticals.

The method or device of any prior embodiment, wherein the samples is cells, tissues, bodily fluids, and stool.

The method or device of any prior embodiment, wherein the sample is the sample in the fields of human, veterinary, agriculture, foods, environments, and drug testing.

The method or device of any prior embodiment, wherein the sample is a biological sample is selected from hair, finger nail, ear wax, breath, connective tissue, muscle tissue, nervous tissue, epithelial tissue, cartilage, cancerous sample, or bone.

The devices or methods of any prior embodiment, wherein the inter-spacer distance is in the range of 5 um to 120 um. um The devices or methods of any prior embodiment, wherein the inter-spacer distance is in the range of 120 um to 200 um.

The device of any prior device embodiment, wherein the flexible plates have a thickness in the range of 20 um to 250 um and Young's modulus in the range 0.1 to 5 GPa.

The device of any prior device embodiment, wherein for a flexible plate, the thickness of the flexible plate times the Young's modulus of the flexible plate is in the range 60 to 750 GPa-um.

The device of any prior device embodiment, wherein the layer of uniform thickness sample is uniform over a lateral area that is at least 1 mm2.

The device of any prior device embodiment, wherein the layer of uniform thickness sample is uniform over a lateral area that is at least 3 mm2.

The device of any prior device embodiment, wherein the layer of uniform thickness sample is uniform over a lateral area that is at least 5 mm2.

The device of any prior device embodiment, wherein the layer of uniform thickness sample is uniform over a lateral area that is at least 10 mm2.

The device of any prior device embodiment, wherein the layer of uniform thickness sample is uniform over a lateral area that is at least 20 mm2.

The device of any prior device embodiment, wherein the layer of uniform thickness sample is uniform over a lateral area that is in a range of 20 mm2 to 100 mm2.

The device of any prior device embodiment, wherein the layer of uniform thickness sample has a thickness uniformity of up to +/−5% or better.

The device of any prior device embodiment, wherein the layer of uniform thickness sample has a thickness uniformity of up to +/−10% or better.

The device of any prior device embodiment, wherein the layer of uniform thickness sample has a thickness uniformity of up to +/−20% or better.

The device of any prior device embodiment, wherein the layer of uniform thickness sample has a thickness uniformity of up to +/−30% or better.

The present invention find use in a variety of different applications in various fields, where determination of the presence or absence, and/or quantification of one or more analytes in a sample are desired. For example, the present inventions finds use in the detection of atoms, molecules, proteins, peptides, nucleic acids, synthetic compounds, inorganic compounds, organic compounds, bacteria, virus, cells, tissues, nanoparticles, and the like. The sample can be a sample in various fields, that include, but not limited to, human, veterinary, agriculture, foods, environments, health, wellness, beauty, and others. Among other things, the present method may be used to detect and/or measure the amount of a diagnostic biomarker that is associated with a disease such as cancer, infection, or inflammatory disease (see, e.g., Tables 1-3 of WO2017058827), an autoantibody epitope (see Table 4 of WO2017058827), an allergen epitope (see Table 5 of WO2017058827), an infectious agent (see, e.g., Table 6 of WO2017058827), a miRNA (see, e.g., Table 7 of WO2017058827), an environmental marker (see, e.g., Table 8 of WO2017058827), a foodstuff markers (see, e.g., Table 9 of WO2017058827), a small molecule such as a metabolite or a drug (e.g., THC—COOH (11-nor-9-carboxy-THC)), one or molecules in cell free DNA (cfDNA), including circulating tumor DNA (ctDNA), one or molecules in cell free RNA (cfRNA), and cells, e.g., circulating tumor cells, viruses or bacteria, etc.

In some embodiments, sample is a bodily fluid or a processed form thereof. Bodily fluids of interest include plasma, saliva and urine, although several other bodily fluids may be used in the present method. Bodily fluids include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, and urine. In some embodiments, a sample may be obtained from a subject, e.g., a human, and it may be processed prior to use in the subject assay. For example, prior to analysis, the protein may be extracted from a tissue sample prior to initiating the present method. In particular embodiments, the sample may be a clinical sample, e.g., a sample collected from a patient.

The present method may have a sensitivity of at least 5 fM, 10 fM, 50 fM, 100 fM, 0.5 pM, 1 pM, 5 pM, 10 pM, 50 pM, 100 pM, 0.5 nM, 1 nM, 5 nM, 10 nM, 50 nM or 100 nM depending on the target analyte.

Without wishing to be bound to any particular use, the present method has particular utility in analyzing blood plasma. Blood plasma can be obtained non-invasively and it contains a variety of different, low abundance proteins that are diagnostic, prognostic or theranostic (see, generally, Anderson et al., Molecular & Cellular Proteomics 2002 1: 845-867 and Anderson et al., Clinical Chemistry 2010 56: 177-185). As such, in some embodiments, the present method may be used to quantify any one or combination (e.g., 2, 3, 4, 5 or more) of the following proteins in plasma: acid phosphatase, IgG, alanine aminotransferase (ALT or SGPT), IgM, albumin, inhibin-A, aldolase, insulin, alkaline phosphatase (ALP), insulinlike growth factor-I (IGF-I), α-1-acid glycoprotein (orosomucoid), insulinlike growth factor-II (IGF-II), α-1-antitrypsin, IGFBP-1, α-2-antiplasmin, IGFBP-3, α-2-HS-glycoprotein, interleukin-2 receptor (IL-2R), α-2-macroglobulin, isocitric dehydrogenase, α-fetoprotein (tumor marker), K light chains, amylase, lactate dehydrogenase heart fraction (LDH-1), amylase, lactate dehydrogenase liver fraction (LLDH), ACE, lactoferrin, antithrombin III (ATM), A light chains, apolipoprotein A1, lipase, apolipoprotein B, Lp(a), aspartate aminotransferase (AST or SGOT), lipoprotein-associated phospholipase A2 (LP-PLA2), 3-2 microglobulin, LH, 3-thromboglobulin, lysozyme, biotinidase, macrophage migration inhibitory factor (MIF) myeloperoxidase (MPO), cancer antigen 125 (CA 125), myoglobin, cancer antigen 15-3 (CA 15-3), osteocalcin, cancer antigen, human epididymis protein (HE4), parathyroid hormone, carcinoembryonic antigen (CEA), phosphohexose isomerase, ceruloplasmin, plasminogen, cholinesterase, plasminogen activator inhibitor (PAI), complement C1, prealbumin, complement C1 Inhibitor, NTproBNP, complement C1Q, procalcitonin (PCT), complement C3, prolactin, complement C4, properdin factor B, complement C5, prostatic acid phosphatase (PAP), CRP, prostatic specific antigen (PSA), creatine kinase-BB (CKBB), protein C, creatine kinase-MM (CKMM), protein S, cystatin C, pseudocholinesterase, erythropoietin, pyruvate kinase, factor IX antigen, renin, factor X, retinol binding protein (RBP), factor XIII, sex hormone-binding globulin, ferritin, soluble mesothelin-related peptide, fibrinogen, sorbital dehydrogenase (SDH), fibronectin, thyroglobulin, FSH, TSH, GGT, thyroxine binding globulin (TBG), haptoglobin, tissue plasminogen activator (T-PA), human chorionic gonadotropin (hCG), transferrin, hemopexin, transferrin receptor (TFR), her-2/neu protein, troponin T (TnT), human growth hormone (HGH), TnI (cardiac), human placental lactogen (HPL), trypsin, IgA, urokinase, IgD, Von Willebrand factor, IgE, nucleotidase, IgG subclass 4, ADAMTS13 activity and inhibitor, inhibin B (infertility), adenosine deaminase, IGFBP-2, adiponectin, intercellular adhesion molecule 1, a subunit of pituitary glycoprotein hormones, interferon interferon-☐, α-galactosidase, interferon-α, EIA, α-N-acetylglucosaminidase, interleukin-1 receptor antagonist, amyloid 13-protein, interleukin-1 soluble receptor type II, angiotensinogen, interleukin-1α, anti-Mullerian hormone (AMH), interleukin-113, 3-glucuronidase, interleukin-2, 3-N-acetylglucosaminidase, interleukin-3, calprotectin, interleukin-4, cancer antigen 72-4, interleukin-5 cholecystokinin, interleukin-6, complement C2, interleukin-7, complement C4 binding protein, interleukin-8, complement C6, interleukin-9, complement C7 level, interleukin-10, complement C8 level, interleukin-11, complement C9 level, interleukin-12, corticosteroid binding globulin (transcortin), interleukin-13, CYFRA 21-1 (soluble cytokeratin fragment), interleukin-14, dopa decarboxylase, interleukin-15, elastase, interleukin-16, eosinophil cationic protein, interleukin-17, epidermal growth factor, interleukin-18, epidermal growth factor receptor (EGFR), kallikrein, factor II, leptin, factor V, leucine aminopeptidase, factor VII, mannose-binding lectin, factor VIII, neuron-specific enolase (NSE), factor XI, neurophysin, factor XII, pancreastatin, fibroblast growth factor (FGF2), pepsinogen I, gastric inhibitory polypeptide (GIP), pepsinogen II, Glial cell-derived neurotrophic factor (GDNF), glutathione peroxidase, proteasome activity, plasma-based Leumeta, granulocyte colony-stimulating factor, S-100B protein, granulocyte-macrophage colony-stimulating factor, soluble CD30, growth hormone binding protein, squamous cell carcinoma antigen, hemoglobin, thyrotropin releasing hormone (TRH), heparin cofactor II, transforming growth factor-131, hexosaminidase A and total hexosaminidase, tumor necrosis factor receptor 1, high molecular weight kininogen, tumor necrosis factor receptor 2, human growth hormone-releasing hormone (HGH-RH), tumor necrosis factor-α, IgG subclass 1, tumor necrosis factor-13, IgG subclass 2, vascular endothelial growth factor (VEGF), IgG subclass 3, and vitamin D-binding protein.

As would be apparent, the method may also be employed to identify a microbial (e.g., bacterial or viral) pathogen in a clinical sample, e.g., a cell surface protein or secreted protein. In these embodiments, the capture agents may target proteins or other moieties from a pathogen. If circles are detected, then the subject may be diagnosed as being infected by that pathogen. Microbes that might be identified using the present methods, compositions and kits include but are not limited to: viruses, yeast, Gram (+) bacteria, Gram (−) bacteria, bacteria in the family Enterobacteriaceae, bacteria in the genus *Enterococcus*, bacteria in the genus *Staphylococcus*, and bacteria in the genus *Campylobacter, Escherichia coli (E. coli), E. coli* of various strains such as, K12-MG1655, CFT073, O157:H7 EDL933, O157:H7 VT2-Sakai, etc., *Streptococcus pneumoniae, Pseudomonas aeruginosa, Staphylococcus aureus*, coagulase-negative staphylococci, a plurality of *Candida* species including *C. albicans, C. tropicalis, C. dubliniensis, C. viswanathii, C. parapsilosis, Klebsiella pneumoniae*, a plurality of *Mycobacterium* species such as *M. tuberculosis, M. bovis, M. bovis* BCG, *M. scrofulaceum, M. kansasii, M. chelonae, M. gordonae, M. ulcerans, M. genavense, M. xenoi, M. simiae, M. fortuitum, M. malmoense, M. celatum, M. haemophilum* and *M. africanum, Listeria* species, *Chlamydia* species, *Mycoplasma* species, *Salmonella* species, *Brucella* species, *Yersinia* species, etc. Thus, the subject method enables identification of microbes to the level of the genus, species, sub-species, strain or variant of the microbe.

In some embodiments, the results of the method may be diagnostic (e.g., may provide a diagnosis of a disease or condition or the type or stage of a disease or condition, etc.), prognostic (e.g., indicating a clinical outcome, e.g., survival or death within a time frame) or theranostic (e.g., indicating which treatment would be the most effective). In some embodiments, the method may be used to analyze a group of 1, 2, 3, 4, 5, 6, 7, 8, 9 or 10 or more analytes that are independently either present at a higher concentration or lower concentration relative to a control (e.g., an internal control), where collectively the identity of the analytes and their abundance correlate with a phenotype.

The method may be used to analyze a patient sample. In this embodiment, the method may comprise: (a) quantifying, using the above-described method, one or more analytes in a sample and (b) providing a report indicating a correlation with phenotype. This embodiment may further comprise making a diagnosis, prognosis or theranosis based on the report. The report may indicate the normal range of the analyte.

In some embodiments, the method may involve creating a report as described above (an electronic form of which may have been forwarded from a remote location) and forwarding the report to a doctor or other medical professional to determine whether a patient has a phenotype (e.g., cancer, etc.) or to identify a suitable therapy for the patient. The report may be used as a diagnostic to determine whether the subject has a disease or condition, e.g., a cancer. In certain embodiments, the method may be used to determine the stage or type of cancer, to identify metastasized cells, or to monitor a patient's response to a treatment, for example.

In any embodiment, report can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information refers to transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or email transmissions and information recorded on websites and the like. In certain embodiments, the report may be analyzed by an MD or other qualified medical professional, and a report based on the results of the analysis of the image may be forwarded to the patient from which the sample was obtained.

Present Embodiments

A device for analyzing a sample comprising:
a first plate, a second plate, a surface amplification layer, and a capture agent, wherein
(e) the first and second plats are movable relative to each other into different configurations, and have, on its respective surface, a sample contact area for contacting a sample that contains a target analyte,
(f) the surface amplification layer is on one of the sample contact areas,
(g) the capture agent is immobilized on the surface amplification layer, wherein the capture agent specifically binds the target analyte,
wherein the surface amplification layer amplifies an optical signal from the target analyte or a label attached to the target analyte when they are is in proximity of the surface amplification layer much stronger than that when they are micron or more away,
wherein one of the configurations is an open configuration, in which the average spacing between the inner surfaces of the two plates is at least 200 um; and wherein another of the configurations is a close configuration, in which, at least part of the sample is between the two plates and the average spacing between the inner surfaces of the plates is less than 200 um.

A device for analyzing a sample comprising:
a first plate, a second plate, a surface amplification layer, and a capture agent, wherein
(h) the first and second plats are movable relative to each other into different configurations, and have, on its respective surface, a sample contact area for contacting a sample that contains a target analyte,
(i) the surface amplification layer is on one of the sample contact areas,
(j) the capture agent is immobilized on the surface amplification layer, wherein the capture agent specifically binds the target analyte,
wherein the surface amplification layer amplifies an optical signal from a label attached to the target analyte when it is in proximity of the surface amplification layer much stronger than that when it is micron or more away,
wherein one of the configurations is an open configuration, in which the average spacing between the inner surfaces of the two plates is at least 200 um;
wherein another of the configurations is a close configuration, in which, at least part of the sample is between the two plates and the average spacing between the inner surfaces of the plates is less than 200 um;
wherein the thickness of the sample in the closed configuration, the concentration of the labels dissolved in the sample in the closed configuration, and the amplification factor of the surface amplification layer are configured such that any the labels that are bound directly or indirectly to the capture agents are visible in the closed configuration without washing away of the unbound labels.

An apparatus comprising a device of any prior embodiment and a reader for reading the device.

A homogeneous assay method using a device of any prior embodiment, wherein the thickness of the sample in a closed configuration, the concentration of labels, and amplification factor of the amplification surface are configured to make the label(s) bound on the amplification surface visible without washing away of the unbound labels.

The method of embodiment 4, wherein the method is done by:
obtaining a device of any of any prior embodiment
depositing a sample on one or both of the plates when the plates are in an open configuration;
closing the plates to the closed configuration; and
reading the sample contact area with a reading device to produce an image of signals.

The device or method of any prior embodiment, wherein the labels bound to the amplification surface are visible in less than 60 seconds.

The device or method of any prior embodiment, wherein the method is a homogeneous assay in which the signal is read without using a wash step to remove any biological materials or labels that are not bound to the amplification surface.

The device or method of any prior embodiment, wherein the labels bound to the amplification surface are read by a pixelated reading method.

The device or method of any prior embodiment, wherein the labels bound to the amplification surface are read by a lump-sum reading method.

The device or method of any prior embodiment, wherein the assay has a detection sensitivity of 0.1 nM or less.

The device or method of any prior embodiment, wherein the method biological materials or labels that are not bound to the amplification surface are removed by a sponge prior to reading.

The device or method of any prior embodiment, wherein the signal amplification layer comprises a D2PA.

The device or method of any prior embodiment, wherein the signal amplification layer comprises a layer of metallic material.

The device or method of any prior embodiment, wherein the signal amplification layer comprises a continuous metallic film that is made of a material selected from the group consisting of gold, silver, copper, aluminum, alloys thereof, and combinations thereof.

The device or method of any prior embodiment, wherein the different metals layers either locally enhance or act as a reflector, or both, to enhance an optical signal.

The device or method of any prior embodiment, wherein the signal amplification layer comprises a layer of metallic material and a dielectric material on top of the metallic material layer, wherein the capture agent is on the dielectric material.

The device or method of any prior embodiment, wherein the metallic material layer is a uniform metallic layer, nanostructured metallic layer, or a combination.

The device or method of any prior embodiment, wherein the amplifies signals by plasmonic enhancement.

The device or method of any prior embodiment, wherein assay comprises detecting the labels by Raman scattering.

The device or method of any prior embodiment, wherein the capture agent is an antibody.

The device or method of any prior embodiment, wherein the capture agent is a polynucleotide.

The device or method of any prior embodiment, wherein the device further comprise spacers fixed on one of the plate, wherein the spacers regulate the spacing between the first plate and the second plate in the closed configuration.

The device or method of any prior embodiment, wherein the amplification factor of the surface amplification layer is adjusted to make the optical signal from a single label that is bound directly or indirectly to the capture agents visible.

The device or method of any prior embodiment, wherein the amplification factor of the surface amplification layer is adjusted to make the optical signal from a single label that is bound directly or indirectly to the capture agents visible, wherein the visible single labels bound to the capture agents are counted individually.

The device or method of any prior embodiment, wherein the spacing between the first plate and the second plate in the closed configuration is configured to make saturation binding time of the target analyte to the capture agents 300 sec or less.

The device or method of any prior embodiment, wherein the spacing between the first plate and the second plate in the closed configuration is configured to make saturation binding time of the target analyte to the capture agents 60 sec or less.

The device or method of any prior embodiment, wherein the amplification factor of the surface amplification layer is adjusted to make the optical signal from a single label visible.

The device or method of any prior embodiment, wherein the capture agent is a nucleic acid.

The device or method of any prior embodiment, wherein the capture agent is a protein.

The device or method of any prior embodiment, wherein the capture agent is an antibody.

The device or method of any prior embodiment, wherein the sample contact area of the second plate has a reagent storage site, and the storage site is approximately above the binding site on the first plate in the closed configuration.

The device or method of any prior embodiment, wherein the reagent storage site comprises a detection agent that binds to the target analyte.

The device or method of any prior embodiment, wherein the detection agent comprises the label.

The device or method of any prior embodiment, wherein the capture agent and detection agent both bind to the target analyte to form a sandwich that comprises the label.

The device or method of any prior embodiment, wherein the signal amplification layer comprises a layer of metallic material.

The device or method of any prior embodiment, wherein the signal amplification layer comprises a layer of metallic material and a dielectric material on top of the metallic material layer, wherein the capture agent is on the dielectric material.

The device or method of any prior embodiment, wherein the metallic material layer is a uniform metallic layer, nanostructured metallic layer, or a combination.

The device or method of any prior embodiment, wherein the amplification layer comprises a layer of metallic material and a dielectric material on top of the metallic material layer, wherein the capture agent is on the dielectric material, and the dielectric material layer has a thickness of 0.5 nm, 1 nm, 5 nm, 10 nm, 20 nm, 50 nm, 00 nm, 200 nm, 500 nm, 1000 nm, 2 um, 3 um, 5 um, 10 um, 20 um, 30 um, 50 um, 100 um, 200 um, 500 um, or in a range of any two values.

The device or method of any prior embodiment, wherein the method further comprises quantifying a signal in an area of the image to providing an estimate of the amount of one or more analytes in the sample.

The device or method of any prior embodiment, wherein the method comprises identifying and counting individual binding events between an analyte with the capture agent in an area of the image, thereby providing an estimate of the amount of one or more analytes in the sample.

The device or method of any prior embodiment, wherein the identifying and counting steps comprise: (1) determining the local intensity of background signal, (2) determining local signal intensity for one label, two labels, three labels, and four or more labels; and (3) determining the total number of labels in the imaged area.

The device or method of any prior embodiment, wherein the identifying and counting steps comprise: (1) determining the local spectrum of background signal, (2) determining local signal spectrum for one label, two labels, three labels, and four or more labels; and (3) determining the total number of labels in the imaged area.

The device or method of any prior embodiment, wherein the identifying and counting steps comprise: (1) determining the local Raman signature of background signal, (2) determining local signal Raman signature for one label, two labels, three labels, and four or more labels; and (3) determining the total number of labels in the imaged area.

The device or method of any prior embodiment, wherein the identifying and counting step comprises determining one or more of the local intensity, spectrum, and Raman signatures.

The device or method of any prior embodiment, wherein the method comprises quantifying a lump-sum signal in an area of the image, thereby providing an estimate of the amount of one or more analytes in the sample.

The device or method of any prior embodiment, wherein the sample contact area of the second plate has a reagent storage site, and the storage site is, in a closed configuration, approximately above the binding site on the first plate.

The device or method of any prior embodiment, wherein the method further comprises a step of labeling the target analyte with a detection agent.

The device or method of any prior embodiment, wherein the detection agent comprises a label.

The device or method of any prior embodiment, wherein the capture agent and detection agent both bind to the target analyte to form a sandwich.

The device or method of any prior embodiment, wherein the method further comprises measuring the volume of the sample in the area imaged by the reading device.

The device or method of any prior embodiment, wherein the target analyte is a protein, peptide, DNA, RNA, nucleic acid, small molecule, cell, or nanoparticle.

The device or method of any prior embodiment, wherein the image shows the position, local intensity, and local spectrum of the signals.

The device or method of any prior embodiment, wherein the signals are luminescence signals selected from the group consisting of fluorescence, electroluminescence, chemiluminescence, and electrochemiluminescence signals.

The device or method of any prior embodiment, wherein the signals are Raman scattering signals.

The device or method of any prior embodiment, wherein the signals are the forces due to local electrical, local mechanical, local biological, or local optical interaction between the plate and the reading device.

The method or device of any prior embodiment, wherein the spacers have pillar shape and nearly uniform cross-section.

The method or device of any prior embodiment, wherein the inter spacer distance (SD) is equal or less than about 120 um (micrometer).

The method or device of any prior embodiment, wherein the inter spacer distance (SD) is equal or less than about 100 um (micrometer).

The method or device of any prior embodiment, wherein the fourth power of the inter-spacer-distance (ISD) divided by the thickness (h) and the Young's modulus (E) of the flexible plate (ISD$^4$/(hE)) is 5×10$^6$ um$^3$/GPa or less.

The method or device of any prior embodiment, wherein the fourth power of the inter-spacer-distance (ISD) divided by the thickness (h) and the Young's modulus (E) of the flexible plate (ISD$^4$/(hE)) is 5×10$^5$ um$^3$/GPa or less.

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD$^4$/(hE)) is 5×10$^6$ um$^3$/GPa or less.

The method or device of any prior embodiment, wherein the ratio of the inter-spacing distance of the spacers to the average width of the spacer is 2 or larger, and the filling factor of the spacers multiplied by the Young's modulus of the spacers is 2 MPa or larger.

The method or device of any prior embodiment, wherein the analytes is proteins, peptides, nucleic acids, synthetic compounds, or inorganic compounds.

The method or device of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The method or device of any prior embodiment, wherein the spacers have a shape of pillars and a ratio of the width to the height of the pillar is equal or larger than one.

The method or device of any prior embodiment, wherein the sample that is deposited on one or both of the plates has an unknown volume.

The method or device of any prior embodiment, wherein the spacers have a shape of pillar, and the pillar has substantially uniform cross-section.

The method or device of any prior embodiment, wherein the samples is for the detection, purification and quantification of chemical compounds or biomolecules that correlates with the stage of certain diseases.

The method or device of any prior embodiment, wherein the samples is related to infectious and parasitic disease, injuries, cardiovascular disease, cancer, mental disorders, neuropsychiatric disorders, pulmonary diseases, renal diseases, and other and organic diseases.

The method or device of any prior embodiment, wherein the samples is related to the detection, purification and quantification of microorganism.

The method or device of any prior embodiment, wherein the samples is related to virus, fungus and bacteria from environment, e.g., water, soil, or biological samples.

The method or device of any prior embodiment, wherein the samples is related to the detection, quantification of chemical compounds or biological samples that pose hazard to food safety or national security, e.g. toxic waste, anthrax.

The method or device of any prior embodiment, wherein the samples is related to quantification of vital parameters in medical or physiological monitor.

The method or device of any prior embodiment, wherein the samples is related to glucose, blood, oxygen level, total blood count.

The method or device of any prior embodiment, wherein the samples is related to the detection and quantification of specific DNA or RNA from biosamples.

The method or device of any prior embodiment, wherein the samples is related to the sequencing and comparing of genetic sequences in DNA in the chromosomes and mitochondria for genome analysis.

The method or device of any prior embodiment, wherein the samples is related to detect reaction products, e.g., during synthesis or purification of pharmaceuticals.

The method or device of any prior embodiment, wherein the samples is cells, tissues, bodily fluids, and stool.

The method or device of any prior embodiment, wherein the sample is the sample in the fields of human, veterinary, agriculture, foods, environments, and drug testing.

The method or device of any prior embodiment, wherein the sample is a biological sample is selected from hair, finger nail, ear wax, breath, connective tissue, muscle tissue, nervous tissue, epithelial tissue, cartilage, cancerous sample, or bone.

The method or device of any prior embodiment, wherein the inter-spacer distance is in the range of 5 um to 120 um.

The method or device of any prior embodiment, wherein the inter-spacer distance is in the range of 120 um to 200 um.

The method or device of any prior embodiment, wherein the flexible plates have a thickness in the range of 20 um to 250 um and Young's modulus in the range 0.1 to 5 GPa.

The method or device of any prior embodiment, wherein for a flexible plate, the thickness of the flexible plate times the Young's modulus of the flexible plate is in the range 60 to 750 GPa-um.

The method or device of any prior embodiment, wherein the layer of uniform thickness sample is uniform over a lateral area that is at least 1 mm$^2$.

The method or device of any prior embodiment, wherein the layer of uniform thickness sample is uniform over a lateral area that is at least 3 mm$^2$.

The method or device of any prior embodiment, wherein the layer of uniform thickness sample is uniform over a lateral area that is at least 5 mm$^2$.

The method or device of any prior embodiment, wherein the layer of uniform thickness sample is uniform over a lateral area that is at least 10 mm$^2$.

The method or device of any prior embodiment, wherein the layer of uniform thickness sample is uniform over a lateral area that is at least 20 mm$^2$.

The method or device of any prior embodiment, wherein the layer of uniform thickness sample is uniform over a lateral area that is in a range of 20 mm$^2$ to 100 mm$^2$.

The method or device of any prior embodiment, wherein the layer of uniform thickness sample has a thickness uniformity of up to +/−5% or better.

The method or device of any prior embodiment, wherein the layer of uniform thickness sample has a thickness uniformity of up to +/−10% or better.

The method or device of any prior embodiment, wherein the layer of uniform thickness sample has a thickness uniformity of up to +/−20% or better.

The method or device of any prior embodiment, wherein the layer of uniform thickness sample has a thickness uniformity of up to +/−30% or better.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A device for analyzing a sample comprising:
a first plate, a second plate, a surface amplification layer, and a capture agent, wherein:
  (a) the first and second plates are movable relative to each other into different configurations including an open configuration and a closed configuration, and have, on their respective surface, a sample contact area for contacting the sample that contains a target analyte, (b) the surface amplification layer is on one of the sample contact areas, (c) the capture agent is immobilized on the surface amplification layer, wherein the capture agent specifically binds the target analyte, wherein the surface amplification layer amplifies an optical signal from the target analyte or a label attached to the target analyte in a proximity-dependent manner that makes the target analyte or the label attached to the target analyte closer to the surface amplification layer having a larger optical signal than that of the target analyte or the label attached to the target analyte farther away from the surface amplification layer, wherein in the open configuration, the average spacing between the inner surfaces of the two plates is at least 200 µm; and wherein in the closed configuration, at least part of the sample is between the two plates, and the average spacing between the inner surfaces of the first and second plates is less than 200 µm.

2. The device of claim 1, wherein the surface amplification layer amplifies the optical signal from the label attached to the target analyte when the label attached to the target analyte is in proximity to the surface amplification layer greater than when it is a micron or more away, and wherein the thickness of the sample in the closed configuration, the concentration of the label dissolved in the sample in the closed configuration, and an amplification factor of the surface amplification layer are configured such that the label that are bound directly or indirectly to the capture agent are visible in the closed configuration without washing away of the unbound labels.

3. An apparatus comprising the device of claim 1 and a reader for reading the device.

4. The device of claim 1, wherein the sample thickness is selected to be thin, so that the total assay time is less than 60 seconds.

5. The device of claim 1, wherein the surface amplification layer comprises a disk-coupled dots-on-pillar antenna (D2PA).

6. The device of claim 1, wherein the surface amplification layer comprises a layer of metallic material.

7. The device of claim 1, wherein the surface amplification layer comprises a continuous metallic film that is made of a material selected from the group consisting of gold, silver, copper, aluminum, an alloy thereof, and a combination thereof.

8. The device of claim 1, wherein the surface amplification layer comprises different metals layers that either locally enhance or act as a reflector, or both, to enhance the optical signal.

9. The device of claim 1, wherein the surface amplification layer comprises a layer of metallic material and a dielectric material on top of the layer of the metallic material, wherein the capture agent is on the dielectric material.

10. The device of claim 6, wherein the layer of metallic material is a uniform metallic layer, nanostructured metallic layer, or a combination.

11. The device of claim 1, wherein the surface amplification layer amplifies the optical signal by plasmonic enhancement.

12. The device of claim 1, wherein the capture agent is an antibody.

13. The device of claim 1, wherein the capture agent is a polynucleotide.

14. The device of claim 1, further comprising spacers fixed on one of the first and second plates, wherein the spacers regulate the spacing between the first plate and the second plate in the closed configuration, and wherein one of the first and second plates is flexible.

15. The device of claim 2, wherein the amplification factor of the surface amplification layer is adjusted to make the optical signal from a single label that is bound directly or indirectly to the capture agent visible.

16. The device of claim 2, wherein the amplification factor of the surface amplification layer is adjusted to make the optical signal from a single label that is bound directly or indirectly to the capture agent visible, wherein the visible single label bound to the capture agent are counted individually.

17. The device of claim 1, wherein the spacing between the first plate and the second plate in the closed configuration is configured to make saturation binding time of the target analyte to the capture agent 300 seconds or less.

18. The device of claim 1, wherein the spacing between the first plate and the second plate in the closed configuration is configured to make saturation binding time of the target analyte to the capture agent 60 seconds or less.

19. The device of claim 2, wherein the amplification factor of the surface amplification layer is adjusted to make the optical signal from a single label visible.

20. The device of claim 1, wherein the capture agent is a nucleic acid.

21. The device of claim 1, wherein the capture agent is a protein.

22. The device of claim 1, wherein the capture agent is an antibody.

23. The device of claim 1, wherein the sample contact area of the second plate has a reagent storage site, and the storage site is approximately above a binding site on the first plate in the closed configuration.

24. The device of claim 23, wherein the reagent storage site comprises a detection agent that binds to the target analyte.

25. The device of claim 24, wherein the detection agent comprises the label.

26. The device of claim 24, wherein the capture agent and detection agent both bind to the target analyte to form a sandwich that comprises the label.

27. The device of claim 2, wherein the surface amplification layer comprises a layer of metallic material.

28. The device of claim 2, wherein the surface amplification layer comprises a layer of metallic material and a dielectric material on top of the layer of the metallic material, wherein the capture agent is on the dielectric material.

29. The device of claim 2, wherein the layer of the metallic material is a uniform metallic layer, nanostructured metallic layer, or a combination.

30. The device of claim 1, wherein the amplification layer comprises a layer of metallic material and a layer of dielectric material on top of the layer of the metallic material, wherein the capture agent is on the dielectric material, and the layer of the dielectric material has a thickness of 0.5 nm, 1 nm, 5 nm, 10 nm, 20 nm, 50 nm, 100 nm, 200 nm, 500 nm, or in a range of between any two of the above thicknesses.

31. The device of claim 1, wherein the sample contact area of the second plate has a reagent storage site, and the reagent storage site is, in a closed configuration, approximately above a binding site on the first plate.

32. The device of claim 1, wherein the target analyte is a protein, peptide, DNA, RNA, nucleic acid, small molecule, cell, or nanoparticle.

33. The device of claim 1, wherein the optical signal comprises a luminescence signal selected from the group consisting of fluorescence, electroluminescence, chemiluminescence, and electrochemiluminescence signals.

34. The device of claim 1, wherein the optical signal is a Raman scattering signal.

35. The device of claim 1, wherein the optical signal the forces due to local electrical, local mechanical, local biological, or local optical interaction between the plate and a reading device.

36. The device of claim 14, wherein each of the spacers has pillar shape and nearly uniform cross-section.

37. The device of claim 14, wherein the inter spacer distance (ISD) is equal or less than about 120 μm (micrometer).

38. The device of claim 14, wherein the spacers have an inter-spacer distance (ISD) equal or less than about 100 μm (micrometer).

39. The device of claim 14, wherein the fourth power of an inter-spacer-distance (ISD) of the spacers divided by the thickness (h) and the Young's modulus (E) of the flexible plate (ISD$^4$/(hE)) is 5×10$^6$ μm$^3$/GPa or less, and the thickness of the flexible plate times the Young's modulus of the flexible plate is in the range 60 to 750 GPa-μm.

40. The device of claim 14, wherein the fourth power of an inter-spacer-distance (ISD) of the spacers divided by the thickness (h) and the Young's modulus (E) of the flexible plate (ISD$^4$/(hE)) is 5×10$^5$ μm$^3$/GPa or less, and the thickness of the flexible plate times the Young's modulus of the flexible plate is in the range 60 to 750 GPa-μm.

41. The device of claim 14, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

42. The device of claim 14, wherein the spacers have pillar shape, a predetermined substantially uniform height, and a predetermined constant inter-spacer distance, wherein the Young's modulus of the spacers times the filling factor of the spacers is equal or larger than 20 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the plate (ISD$^4$/(hE)) is 5×10$^5$ μm$^3$/GPa or less, and wherein the thickness of a plate times the Young's modulus of the plate is in the range 60 to 750 GPa-μm.

43. The device of claim 14, wherein the ratio of the inter-spacer distance of the spacers to the average width of the spacer is 2 or larger, and the filling factor of the spacers multiplied by the Young's modulus of the spacers is 2 MPa or larger.

44. The device of claim 1, wherein the analyte is a protein, peptide, nucleic acid, synthetic compound, or inorganic compound.

45. The device of claim 1, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

46. The device of claim 1, wherein the spacers are pillars and a ratio of the width to the height of each pillar is equal or larger than one.

47. The device of claim 14, wherein the spacers have a shape of pillar, and the pillar has substantially uniform cross-section.

48. The device of claim 1, wherein the sample is for the detection, purification and quantification of chemical compounds or biomolecules that correlates with the stage of certain diseases.

49. The device of claim 1, wherein the sample is cells, tissues, bodily fluids, and stool.

50. The device of claim 1, wherein the sample is a biological sample is selected from hair, finger nail, ear wax, breath, connective tissue, muscle tissue, nervous tissue, epithelial tissue, cartilage, cancerous sample, or bone.

51. The device of claim 41, wherein the inter-spacer distance is in the range of 5 μm to 120 μm.

52. The device of claim 41, wherein the inter-spacer distance is in the range of 120 μm to 200 μm.

53. The device of claim 1, wherein the first and second plates have a thickness in the range of 20 μm to 250 μm and Young's modulus in the range 0.1 to 5 GPa.

54. The device of claim 1, wherein the thickness of one of the first or second plate times the Young's modulus of the one of the first or second plate is in the range 60 to 750 GPa-μm.

55. The device of claim 2, wherein the sample in the closed configuration is a layer of uniform thickness sample that is uniform over a lateral area that is at least 1 mm$^2$.

56. The device of claim 2, wherein the sample in the closed configuration is a layer of uniform thickness sample that is uniform over a lateral area that is at least 3 mm$^2$.

57. The device of claim 2, wherein the sample in the closed configuration is a layer of uniform thickness sample that is uniform over a lateral area that is at least 5 mm$^2$.

58. The device of claim 2, wherein the sample in the closed configuration is a layer of uniform thickness sample that is uniform over a lateral area that is at least 10 mm$^2$.

59. The device of claim 2, wherein the sample in the closed configuration is a layer of uniform thickness sample that is uniform over a lateral area that is at least 20 mm$^2$.

60. The device of claim 2, wherein the sample in the closed configuration is a layer of uniform thickness sample that is uniform over a lateral area that is in a range of 20 mm$^2$ to 100 mm$^2$.

61. The device of claim 2, wherein the thickness of the sample in the closed configuration is has a thickness uniformity of up to +/−5%.

62. The device of claim 2, wherein the thickness of the sample in the closed configuration has a thickness uniformity of up to +/−10%.

63. The device of claim 2, wherein the thickness of the sample in the closed configuration has a thickness uniformity of up to +/−20%.

64. The device of claim 2, wherein the thickness of the sample in the closed configuration has a thickness uniformity of up to +/−30%.

65. The device of claim 1, wherein the label comprises a particle or bead.

66. The device of claim 65, wherein the particle or bead is a gold nanoparticle, silver nanoparticle, silicon quantum dot, CdSe quantum dot, silicon nanowire, melamine resin particle, fluorescently labeled microparticle, carboxylate-modified melamine microparticle, fluorescent nanobead, polyacrylnitrile (pan) nanoparticle, fluorescent polystyrene bead, latex particle, or a combination thereof.

67. The device of claim 66, wherein the particle or bead has an average size of 1 nm to 2 μm.

68. The device of claim 1, wherein the label is within 1 nm to 200 μm distance from a surface of the surface amplification layer.

69. The device of claim 1, wherein the label comprises a bead containing a color bar-code.

70. The apparatus of claim 3, wherein the reader comprises a camera that images the analyte or the label.

71. The device of claim 1, wherein the label comprises beads, and each of the beads has a color bar-code and contains a reagent that has an affinity for an analyte.

72. The device of claim 1, wherein the label comprises beads with different geometric shapes.

73. The device of claim 1, wherein the surface amplification layer comprises a bead.

74. The device of claim 73, wherein the bead is a fluorescence bead or a streptavidin bead.

75. The device of claim 1, wherein the surface amplification layer comprises beads, the beads have different geometric sizes, and each of the beads contains a capture agent for different analytes.

76. The device of claim 1, wherein one of the first and second plates further comprises a plurality of microwells.

77. The device of claim 1, wherein one of the first and second plates further comprises microwells that have different geometric shapes, each one of geometric shapes accommodates one geometric shape of beads.

78. The apparatus of claim 3, wherein the reader comprises a smartphone, and wherein the camera of the smartphone images the analyte or the label.

79. The device of claim 1, wherein the label is a fluorescent bead, and the amplification surface amplifies the optical signal by plasmonic enhancement.

80. The device of claim 1, wherein the label is a fluorescent bead, and the amplification surface is a gold layer.

81. The device of claim 1, wherein the label comprises beads that are magnetic.

82. The device of claim 1, wherein the amplification layer comprises a layer of metallic material and a dielectric material on top of the metallic material layer, wherein the capture agent is on the dielectric material, and the dielectric material layer has a thickness of 1000 nm, 2 μm, 3 μm, 5 μm, 10 μm, 20 μm, 30 μm, 50 μm, 100 μm, 200 μm, 500 μm, or in a range of any two of the above thicknesses.

83. The device of claim 14, further comprising comprises (a) a reading device for producing an image of signals emanating from the device that represent individual targeted analyte binding events; and (b) a computer comprising a program for identifying and counting individual binding events in an area of the image.

84. The device of claim 83, wherein a program for identifying and counting individual binding events in an area of the image uses a pixelated reading method.

85. The device of claim 83, wherein the reading device images the sample without washing away of the unbound labels.

86. The device of claim 83, wherein the reading device is a camera.

87. The device of claim 83, wherein the reading device is a highly sensitive electron multiplying charge coupled device.

88. The device of claim 14, wherein the spacers have a periodic inter-spacer distance.

89. The device of claim 14, wherein the spacers have a periodic inter-space distance (ISD), and wherein a fourth power of the ISD divided by a thickness (h) and a Young's modulus (E) of the flexible plate (ISD$^4$/(hE)) is 5×10$^6$ μm$^3$/GPa or less, and the thickness of the flexible plate times the Young's modulus of the flexible plate is in a range of 60 to 750 GPa-μm.

* * * * *